US012253514B2

(12) United States Patent
Kern et al.

(10) Patent No.: US 12,253,514 B2
(45) Date of Patent: Mar. 18, 2025

(54) COMPOSITIONS AND METHODS FOR MODULATING KINASE ACTIVITY

(71) Applicant: Brandeis University, Waltham, MA (US)

(72) Inventors: Dorothee Kern, Waltham, MA (US); Adelajda Zorba, Waltham, MA (US)

(73) Assignee: Brandeis University, Waltham, MA (US)

( * ) Notice: Subject to any disclaimer, the term of this patent is extended or adjusted under 35 U.S.C. 154(b) by 825 days.

(21) Appl. No.: 17/380,704

(22) Filed: Jul. 20, 2021

(65) Prior Publication Data

US 2023/0050231 A1  Feb. 16, 2023

Related U.S. Application Data

(62) Division of application No. 15/774,747, filed as application No. PCT/US2016/015171 on Jan. 27, 2016, now Pat. No. 11,104,741.

(60) Provisional application No. 62/254,974, filed on Nov. 13, 2015.

(51) Int. Cl.
*G01N 33/50* (2006.01)

(52) U.S. Cl.
CPC ..... *G01N 33/5008* (2013.01); *G01N 2333/47* (2013.01); *G01N 2333/91205* (2013.01); *G01N 2500/04* (2013.01)

(58) Field of Classification Search
CPC ........... G01N 33/5008; G01N 2333/47; G01N 2333/91205; G01N 2500/04; C12Q 1/485; C40B 30/04
See application file for complete search history.

(56) References Cited

U.S. PATENT DOCUMENTS

| 7,214,518 | B2 | 5/2007 | Anderson et al. |
| 2006/0078975 | A1 | 4/2006 | Anderson et al. |
| 2008/0051327 | A1 | 2/2008 | Conti et al. |
| 2011/0143963 | A1 | 6/2011 | Koide et al. |
| 2012/0046307 | A1 | 2/2012 | Engel et al. |

FOREIGN PATENT DOCUMENTS

EP 1522580 A1 4/2005

OTHER PUBLICATIONS

Burgess et al., Open Biology, 6:160089, (Year: 2016).*
Streltsov et al., Protein Science, 14:2901-2909, (Year: 2005).*
Gustafson et al., Cancer Cell, 26(3): 414-427, Sep. 8, 2014.*
Levinson NM, Biochemical Journal 475:2025-2042, (Year: 2018).*
Clark et al., Nature Chemical Biol., 5:647-654, (Year: 2009).*
Burgess, et al.; "Allosteric inhibition of Aurora-A kinase by a synthetic vNAR domain"; Open Biology, vol. 6, Issue No. 7; 2016; pp. 1-10.
International Search Report and Written Opinion for International Application PCT/US2016/015171; International Filing Date: Jan. 27, 2016; Date of Mailing: Jul. 11, 2016; 15 pages.
International Search Report and Written Opinion for International Application PCT/US2017/016923; International Filing Date: Feb. 8, 2017; Date of Mailing: Apr. 21, 2017; 15 pages.
Janeček, et al.; "Allosteric modulation of AURKA kinase activity by a small molecule inhibitor of its protein-protein interaction with TPX2"; Scientific Reports, vol. 6, Issue No. 28528; 2016; pp. 1-12.
Oelschlaeger, et al.; "Fluorophor-linked immunosorbent assay: a time- and cost-saving method for the characterization of antibody fragments using a fusion protein of a single-chain antibody fragment and enhanced green fluorescent protein"; Analytical Biochemistry, vol. 309, Issue No. 1; 2002; pp. 27-34.
Ohashi, et al.; "Phospho-regulation of human protein kinase Aurora-A: analysis using anti-phospho-Thr288 monoclonal antibodies"; Oncogene, vol. 25, Issue No. 59; 2006; pp. 7691-7702.
Wojcik, et al.; "A potent and highly specific FN3 monobody inhibitor of the Abl SH2 domain"; Nature Structual and Molecular Biology, vol. 17, Issue No. 4; 2010; pp. 519-527.
Woldring, et al.; "High-Throughput Ligand Discovery Reveals a Sitewise Gradient of Diversity in Broadly Evolved Hydrophilic Fibronectin Domains" PLoS One, vol. 10, Issue No. 9; 2015; DOI: https://doi.org/10.1371/journal.pone.0138956.
Almargo, J. et al.; "Humanization of antibodies"; Frontiers in Bioscience, vol. 13; 2008; pp. 1619-1633.
Berglund, L. et al.; "The epitope space of the human proteome"; Protein Science, vol. 17, Issue No. 4; 2008; pp. 606-613.
Corada, M. et al.; "Monoclonal antibodies directed to different regions of vascular endothelial cadherin extracellular domain affect adhesion and clustering of the protein and modulate endothelial permeability"; Blood, vol. 97, Issue No. 6; 2001; pp. 1679-1684.
Kulkarni-Kale, U. et al.; "CEP: a conformational epitope prediction server"; Nucleic Acids Research, vol. 33, Issue Supplement 2; 2005; pp. W168-W171; DOI: https://doi.org/10.1093/nar/gki460.
Meulenbeld, H. et al.; "Danusertib, an aurora kinase inhibitor"; Expert Opinion on Investigational Drugs, vol. 21, Issue No. 3; 2021; pp. 383-393.
Padlan, E.; "X-Ray Crystallography of Antibodies"; Advances in Protein Chemistry, vol. 49; 1996; pp. 57-133.
Yu, Xiaowen et al. Beyond Antibodies as Binding Partners: The Role of Antibody Mimetics in Bioanalysis, Annu Rev Anal Chem (Palo Alto Calif). Jun. 12, 2017; 10(1): 293-320.

* cited by examiner

*Primary Examiner* — Kimberly Ballard
*Assistant Examiner* — Stacey N Macfarlane
(74) *Attorney, Agent, or Firm* — Karen A. LeCuyer; DeWitt LLP

(57) ABSTRACT

The present invention features an antibody mimetic, or an antigen binding fragment thereof, that specifically binds to an allosteric site of Aurora A kinase, therapeutic compositions comprising this antibody mimetic, and the use of the monobody to modulate Aurora A kinase for the treatment of cancer.

10 Claims, 30 Drawing Sheets

Specification includes a Sequence Listing.

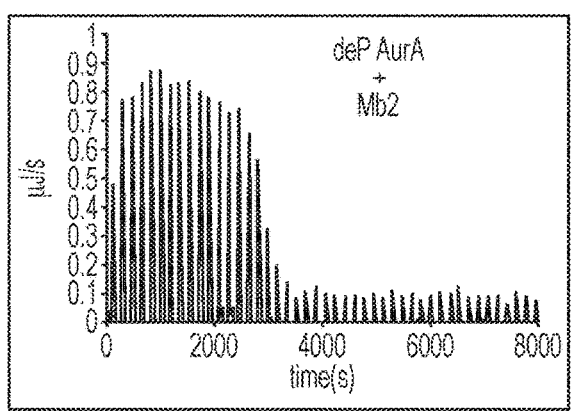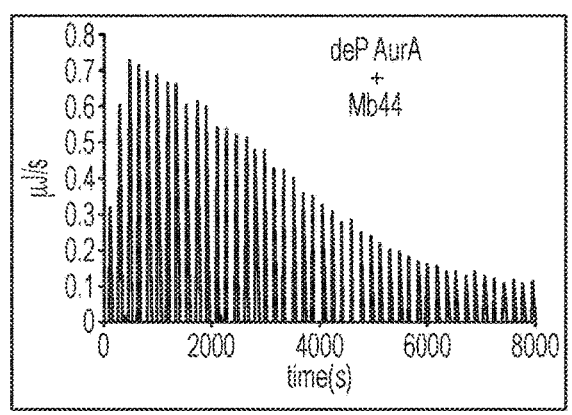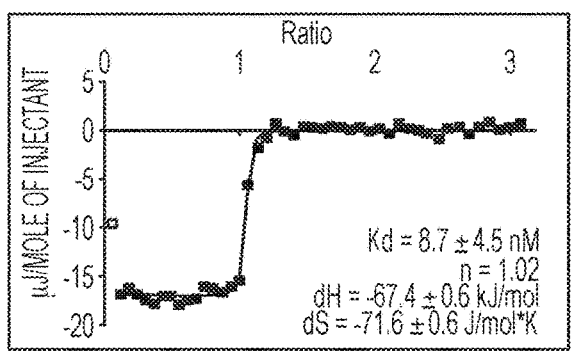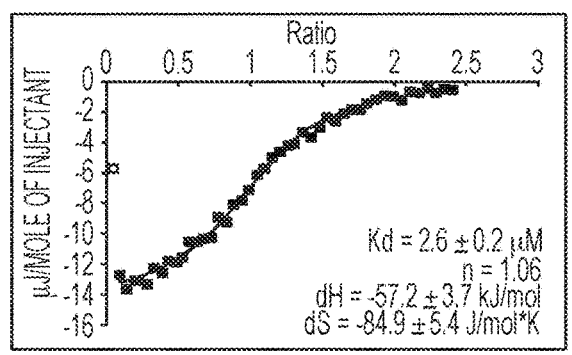
FIG. 2A          FIG. 2B

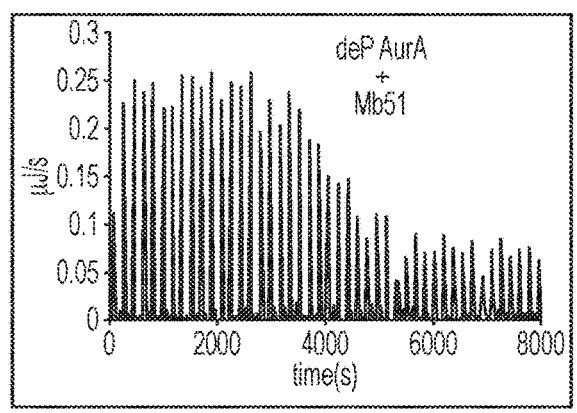
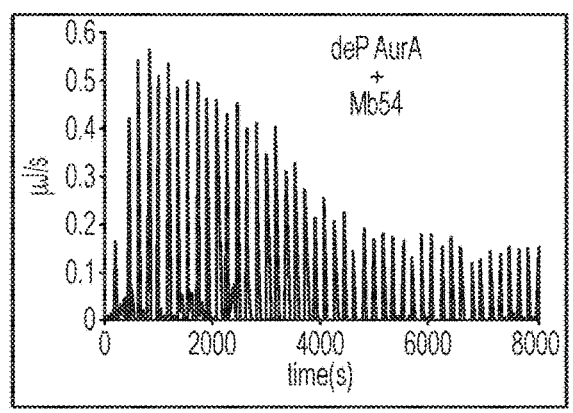
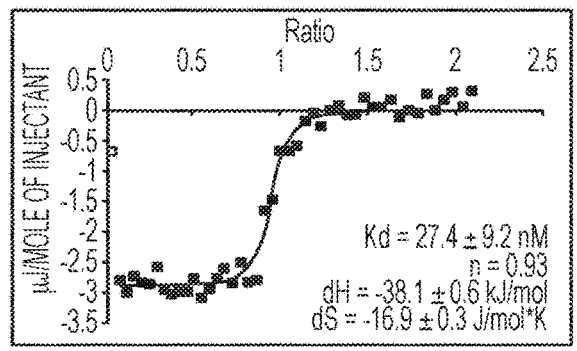
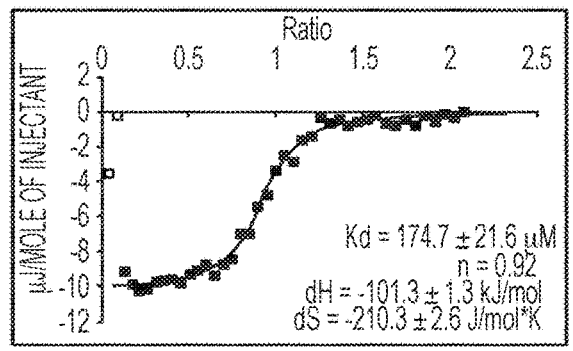
FIG. 2C  FIG. 2D

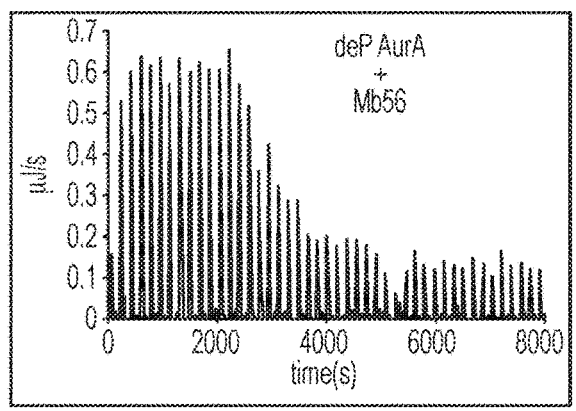
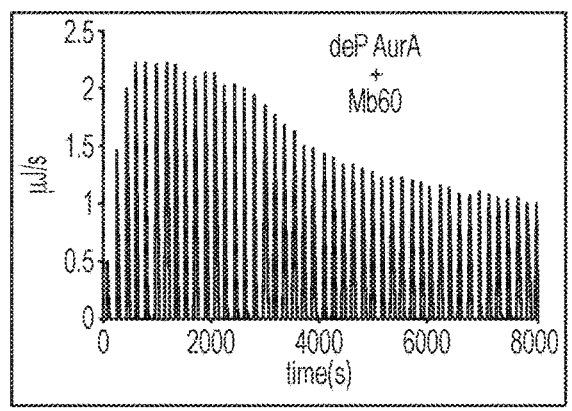
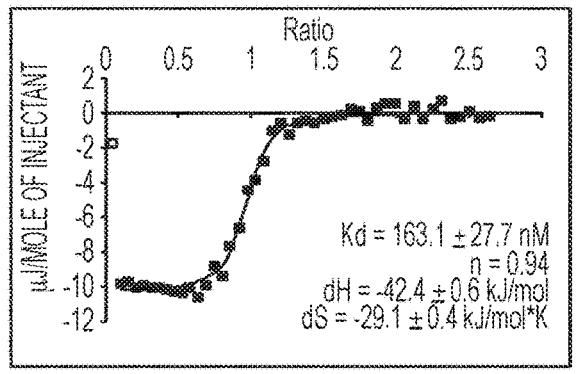
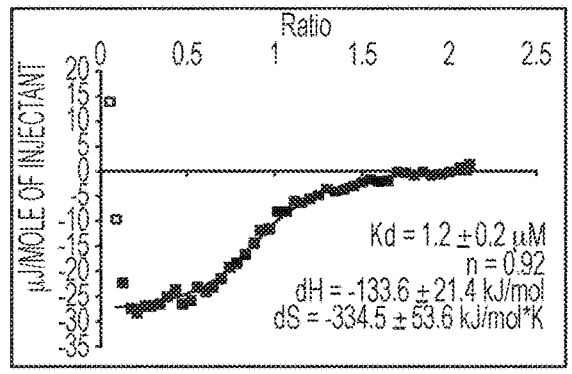
FIG. 2E                              FIG. 2F

COMPOSITIONS AND METHODS FOR MODULATING KINASE ACTIVITY

CROSS REFERENCE TO RELATED APPLICATIONS

This application is a divisional of U.S. application Ser. No. 15/774,747 filed on May 9, 2018, which is a § 371 of PCT/US16/15171, filed on Jan. 27, 2016, which claims the benefit of U.S. Provisional Application Ser. No. 62/254,974, filed on Nov. 13, 2015, the contents of which are incorporated herein by reference in their entirety.

STATEMENT OF RIGHTS TO INVENTIONS MADE UNDER FEDERALLY SPONSORED RESEARCH

This invention was made with government support under Grant No. DE-FG02-05ER15699 awarded by the U.S. Department of Energy and Grant Nos. GM100966-01 and GM096053 awarded by the National Institutes of Health. The government has certain rightsin the invention.

BACKGROUND OF THE INVENTION

Deregulation of protein kinases can lead to aberrant signaling and abnormal events in cells that may contribute to the formation or growth of a cancer. An example of such a protein kinase is Aurora A kinase, an oncoprotein that is overexpressed in a multitude of cancers. As such, ways to inhibit kinases such as Aurora A kinase via small molecule drugs have been actively pursued. Typically, small molecule kinase inhibitors are developed to target the ATP binding pocket of the kinase. However, drugs developed to target the ATP binding site of a kinase are not usually specific for the particular kinase, which may lead to side effects from the drug. Thus, new methods of modulating kinase activity, particularly methods for specifically modulating activity of selected kinases in a cancer, are urgently required.

SUMMARY OF THE INVENTION

The present invention features an antibody mimetic that specifically binds to an allosteric site of Aurora A kinase, therapeutic compositions comprising this antibody mimetic, and the use of the antibody mimetic to modulate the Aurora A kinase for the treatment of cancer.

In one aspect, the present invention provides an antibody mimetic, or an antigen binding fragment thereof, that specifically binds to an allosteric site of Aurora A kinase.

In another aspect, the present invention provides a fusion polypeptide comprising a first polypeptide and a second polypeptide fused to the first polypeptide, wherein the first polypeptide is an antibody mimetic, or an antigen binding fragment thereof, that specifically binds to an allosteric site of Aurora A kinase, and the second polypeptide comprises at least one of the following: (i) a fragment sufficient to mediate intracellular delivery of the antibody mimetic, (ii) an epitope tag, and (iii) a detectable moiety.

In various embodiments of any one of the aspects delineated herein, the antibody mimetic is a monobody. In various embodiments, the antibody mimetic comprises any one of the following sequences:

```
AuroraA 2 (Mb2)
                                    (SEQ ID NO: 1)
SVSSVPTK LEVVAATPTS LLISWDAFGH QYEPVYYYRI

TYGETGGNSP VQEFTVPGYY STATISGLKP GVDYTITVYA

WYVDGSYSSP ISINYRT

AuroraA 44 (Mb44)
                                    (SEQ ID NO: 2)
SVSSVPTK LEVVAATPTS LLISWDAPAV TVDFYVITYG

ETGGYSYPWQ EFEVPGSKST ATISGLKPGV DYTITVYADY

GQYFYSPISI NYRT

AuroraA 51 (Mb51)
                                    (SEQ ID NO: 3)
SVSSVPTK LEVVAATPTS LLISWDAKPM SYEPVYYYRI

TYGETGGNSP VQEFTVPGYY STATISGLKP GVDYTITVYA

DSMSSYYYSP ISINYRT

AuroraA 54 (Mb54)
                                    (SEQ ID NO: 4)
SVSSVPTK LEVVAATPTS LLISWDAQTY QMYDYVSYYR

ITYGETGGNS PVQEFTVPGY YSTATISGLK PGVDYTITVY

AEGYYSSYSP ISINYRT

AuroraA 56 (Mb56)
                                    (SEQ ID NO: 5)
SVSSVPTK LEVVAATPTS LLISWDAMSD WYYWVDYYRI

TYGETGGNSP VQEFTVPGSY STATISGLKP GVDYTITVYA

SDDVWGDYSP ISINYRT

AuroraA 60 (Mb60)
                                    (SEQ ID NO: 6)
SVSSVPTK LEVVAATPTS LLISWDAPAV TVVHYVITYG

ETGGNSPVQE FTVPGSKSTA TISGLKPGVD YTITVYAIDF

YWGSYSPISI NYRT
```

In various embodiments of any one of the aspects delineated herein, the antibody mimetic or fusion polypeptide binds to the allosteric site with affinity of at least about 1 nM, at least about 10 nM, at least about 100 nM, or at least about 1 µM. In various embodiments, the allosteric site is a PIF pocket. In some embodiments, binding of the antibody mimetic or fusion polypeptide to the allosteric site alters an activity of Aurora A kinase. In some other embodiments, the antibody mimetic or fusion polypeptide binding decreases kinase activity of Aurora A kinase. In still other embodiments, the antibody mimetic or fusion polypeptide binding disrupts binding of TPX2 to Aurora A kinase. In some embodiments, the fragment is a supercharged polypeptide. In some other embodiments, the supercharged polypeptide is supercharged green fluorescent protein (GFP).

In another aspect, the present invention provides an isolated polynucleotide encoding an antibody mimetic or fusion polypeptide of any one of the aspects delineated herein.

In yet another aspect, the present invention provides an expression vector comprising a polynucleotide encoding an antibody mimetic, or an antigen binding fragment thereof, that specifically binds to an allosteric site of Aurora A kinase. In various embodiments, the polynucleotide is the polynucleotide of any one of the aspects delineated herein. In some embodiments, the polynucleotide encodes an amino acid sequence of at least one monobody selected from the group consisting of: Mb2, Mb44, Mb51, Mb56, Mb54, and Mb60.

In still another aspect, the present invention provides a cell comprising the expression vector of any one of the aspects delineated herein. In various embodiments, the cell is a prokaryote or eukaryote.

In another aspect, the present invention provides a method of producing a polypeptide comprising an antibody mimetic, or an antigen binding fragment thereof, that specifically binds to an allosteric site of Aurora A kinase, the method comprising (a) heterologously expressing an expression vector comprising a polynucleotide encoding the polypeptide in a host cell; (b) isolating the polypeptide from the host cell. In various embodiments, the polypeptide is the antibody mimetic or fusion polypeptide of any one of the aspects delineated herein. In some embodiments, the expression vector is the expression vector of any one of the aspects delineated herein. In some other embodiments, the host cell is the cell of any one of the aspects delineated herein.

In yet another aspect, the present invention provides a pharmaceutical composition comprising an effective amount of an antibody mimetic, polypeptide, or polynucleotide of any one of the aspects delineated herein. In some embodiments, the composition further comprises a liposome. In some other embodiments, the composition further comprises a pharmaceutically acceptable excipient. In still other embodiments, the composition is formulated for intravenous delivery.

In another aspect, the present invention provides a method of identifying an antibody mimetic that specifically binds to an allosteric site of Aurora A kinase, the method comprising (a) contacting a candidate antibody mimetic with an Aurora A kinase having an unbound allosteric site, (b) contacting the candidate antibody mimetic with an Aurora A kinase having a bound allosteric site or an Aurora A kinase having a mutation in the allosteric site, and (c) measuring binding of the candidate antibody mimetic with Aurora A kinase in step (a) and in step (b), wherein a candidate antibody mimetic having an increased binding to Aurora A kinase in step (a) relative to step (b) is identified as an antibody mimetic that specifically binds to an allosteric site of Aurora A kinase. In some embodiments, the antibody mimetic is a monobody. In some other embodiments, the allosteric site is a PIF pocket. In some other embodiments, the Aurora A kinase having a bound allosteric site is Aurora A kinase bound with TPX2.

In another aspect, the present invention provides a method of modulating activity of an Aurora A kinase, the method comprising contacting the Aurora A kinase with a polypeptide comprising an antibody mimetic, or antigen binding fragment thereof, that specifically binds to an allosteric site of Aurora A kinase, thereby modulating the activity of the Aurora A kinase.

In yet another aspect, the present invention provides a method of inhibiting proliferation and/or reducing survival of a cell, the method comprising contacting an Aurora A kinase in the cell with a polypeptide comprising an antibody mimetic, or antigen binding fragment thereof, that specifically binds to an allosteric site of Aurora A kinase, thereby inhibiting proliferation and/or reducing survival of the cell.

In still another aspect, the present invention provides a method of treating a cancer in a subject, the method comprising administering to the subject an effective amount of a composition comprising a polypeptide comprising an antibody mimetic, or antigen binding fragment thereof, that specifically binds to an allosteric site of Aurora A kinase, thereby treating the cancer in the subject.

In various embodiments of any one of the aspects delineated herein, the antibody mimetic is a monobody. In some embodiments, the polypeptide is the antibody mimetic or fusion polypeptide of any one of the aspects delineated herein. In some other embodiments, the polypeptide is produced according to the method of any one of the aspects delineated herein. In still other embodiments, the polypeptide binds to the allosteric site with affinity of at least about 1 nM, at least about 10 nM, at least about 100 nM, or at least about 1 µM. In various embodiments, the allosteric site is a PIF pocket.

In some embodiments, binding of the polypeptide to the allosteric site alters an activity of Aurora A kinase. In various embodiments, the polypeptide binding decreases kinase activity of Aurora A kinase. In some other embodiments, the polypeptide binding disrupts binding of TPX2 to Aurora A kinase. In still other embodiments, the polypeptide contacts Aurora A kinase in vitro or in a cell.

In various embodiments of any one of the aspects delineated herein, the polypeptide is delivered to the cell by contacting the cell with a composition comprising the polypeptide or by heterologously expressing the polypeptide in the cell. In some embodiments, the composition further comprises a liposome. In various embodiments, the cell is a cancer cell. In various embodiments of any one of the aspects delineated herein, the subject is human.

Compositions and articles defined by the invention were isolated or otherwise manufactured in connection with the examples provided below. Other features and advantages of the invention will be apparent from the detailed description, and from the claims.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

As used herein, "activity" or "biological activity" of a polypeptide refers to any biological function or any biological interaction of a polypeptide. Activity of a polypeptide may refer to the polypeptide's enzymatic or catalytic activity (e.g., kinase activity). For example, "kinase activity" of Aurora A kinase refers to Aurora A kinase's phosphorylation of a serine or threonine residue on a substrate polypeptide. Activity of a polypeptide may also refer to the polypeptide's binding with another polypeptide, a polynucleotide, or other agentsin a cell. For example, Aurora A kinase's binding to TPX2 is an activity of Aurora A kinase.

The term "antibody," as used herein, refers to an immunoglobulin molecule which specifically binds with an antigen. Methods of preparing antibodies are well known to those of ordinary skill in the science of immunology. Antibodies can be intact immunoglobulins derived from natural sources or from recombinant sources and can be immunoreactive portions of intact immunoglobulins. Antibodies are typically tetramers of immunoglobulin molecules. Tetramers may be naturally occurring or reconstructed from single chain antibodies or antibody fragments. Antibodies also include dimers that may be naturally occurring or constructed from single chain antibodies or antibody fragments. The antibodies in the present invention may exist in a variety of forms including, for example, polyclonal antibodies, monoclonal antibodies, Fv, Fab and F(ab')2, as well as single chain antibodies (scFv), humanized antibodies, and human antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab') 2, and Fv fragments, linear antibodies, scFv antibodies, single-domain antibodies, such as camelid antibodies (Riechmann, 1999, Journal of Immunological Methods 231:25-38), composed of either a VL or a VH domain which exhibit sufficient affinity for the target, and multispecific antibodies formed from antibody fragments. The antibody fragment also includes a human antibody or a humanized antibody or a portion of a human antibody or a humanized antibody.

Antibodies can be made by any of the methods known in the art utilizing a polypeptide of the invention (e.g., Aurora A kinase), or immunogenic fragments thereof, as an immunogen. One method of obtaining antibodies is to immunize suitable host animals with an immunogen and to follow standard procedures for polyclonal or monoclonal antibody production. The immunogen will facilitate presentation of the immunogen on the cell surface. Immunization of a suitable host can be carried out in a number of ways. Nucleic acid sequences encoding a polypeptide of the invention or immunogenic fragments thereof, can be provided to the host in a delivery vehicle that is taken up by immune cells of the host.

The cells will in turn express the receptor on the cell surface generating an immunogenic response in the host. Alternatively, nucleic acid sequences encoding the polypeptide, or immunogenic fragments thereof, can be expressed in cells in vitro, followed by isolation of the polypeptide and administration of the polypeptide to a suitable host in which antibodies are raised.

Alternatively, antibodies against the polypeptide may, if desired, be derived from an antibody phage display library. A bacteriophage is capable of infecting and reproducing within bacteria, which can be engineered, when combined with human antibody genes, to display human antibody proteins. Phage display is the process by which the phage is made to 'display' the human antibody proteins on its surface. Genes from the human antibody gene libraries are inserted into a population of phage. Each phage carries the genes for a different antibody and thus displays a different antibody on its surface.

Antibodies made by any method known in the art can then be purified from the host.

Antibody purification methods may include salt precipitation (for example, with ammonium sulfate), ion exchange chromatography (for example, on a cationic or anionic exchange column preferably run at neutral pH and eluted with step gradients of increasing ionic strength), gel filtration chromatography (including gel filtration HPLC), and chromatography on affinity resins such as protein A, protein G, hydroxyapatite, and anti-immunoglobulin.

Antibodies can be conveniently produced from hybridoma cells engineered to express the antibody. Methods of making hybridomas are well known in the art. The hybridoma cells can be cultured in a suitable medium, and spent medium can be used as an antibody source. Polynucleotides encoding the antibody of interest can in turn be obtained from the hybridoma that produces the antibody, and then the antibody may be produced synthetically or recombinantly from these DNA sequences. For the production of large amounts of antibody, it is generally more convenient to obtain an ascites fluid. The method of raising ascites generally comprises injecting hybridoma cells into an immunologically naive histocompatible or immunotolerant mammal, especially a mouse. The mammal may be primed for ascites production by prior administration of a suitable composition (e.g., Pristane).

By "antibody mimetic" or "antibody mimic" is meant a molecule which specifically binds an antigen, but is not structurally related to antibodies. Typically, antibody mimetics specifically binding to a target are produced by screening libraries of mutagenized molecular scaffolds. Examples of molecular scaffolds include, without limitation, a fibronectin III (FN3) domain. The molecular scaffold is typically a smaller molecule than an antibody (e.g., about 50-200 residues). Examples of antibody mimetics include, without limitation, affibodies, affilins, affitins, anticalins, avimers, DARPins, Kunitz domain derived peptides, knottins and monobodies. In particular embodiments, an antibody mimetic of the invention is a monobody specifically binding to the PIF pocket of Aurora A kinase.

As used herein, "affinity" or "binding affinity" refers to the strength of binding of an agent to another agent (in particular, binding of a polypeptide to another polypeptide). An exemplary quantitative measure of affinity is the dissociation constant, Kct. The Kct is a measure relating concentrations of unbound agents with concentrations of bound agents at equilibrium. For example, in an exemplary binding reaction, an agent (A) binds to another agent (B) to form a complex (AB). The dissociation constant, Kt, for the binding between A and Bis Kct=[A][B]/[AB], where [A] is the concentration of unbound A at equilibrium, [B] is the concentration of unbound B at equilibrium, and [AB] is the concentration of A and B bound together (i.e., concentration of bound A or bound B) at equilibrium. A high affinity of A to Bis reflected in low concentrations of unbound A and unbound B and high concentrations of A bound to B at equilibrium. Low concentrations of unbound A and unbound B and high concentrations of A bound to B at equilibrium yield a low Kt value.

Thus, the Kt is inversely related to affinity; a lower value of Kt indicates a higher affinity.

By "agent" is meant any small molecule chemical compound, antibody, nucleic acid molecule, or polypeptide, or fragments thereof.

By "allosteric regulation," "allosteric control," or "allosteric modulation" of polypeptide activity is meant modulation of activity of the polypeptide via binding of an effector molecule to a site other than the polypeptide's active site. Binding of the effector molecule to this site (i.e., the "allosteric site") may induce conformational changes in the polypeptide that alters the active site, thereby altering the polypeptide's activity. The TPX2 polypeptide is an exemplary allosteric regulator of kinase activity of a polypeptide. TPX2 polypeptide binds to the PIF pocket of Aurora A kinase, an allosteric site on Aurora A kinase. TPX2 polypeptide does not bind to the Aurora A kinase ATP-binding site, the active site of Aurora A kinase. Binding of TPX2 polypeptide to the PIF pocket of Aurora A kinase activates kinase activity of Aurora A kinase. In some embodiments, a monobody of the invention is an allosteric regulator of kinase activity of Aurora A kinase. In particular embodiments, a monobody of the invention binds to the allosteric site (i.e., PIF pocket) of Aurora A kinase. In particular embodiments, binding of a monobody of the invention to the allosteric site inhibits or activates kinase activity of Aurora A kinase.

By "ameliorate" is meant decrease, suppress, attenuate, diminish, arrest, or stabilize the development or progression of a disease. Diseases include cancers characterized by an increase in Aurora A kinase activity.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels. In one embodiment, a monobody of the invention alters Aurora A kinase activity by at least about 5%, 10%, 15%, 20%, 25% or more.

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid. By "Aurora A," "Aurora A kinase," or "Aurora A polypeptide" is meant a polypeptide or fragment thereof having at least about 85% or greater amino acid identity to the amino acid sequence provided at NCBI Accession No. NP 940839 and having serine/threonine kinase activity. An exemplary polypeptide sequence of Aurora A kinase is provided below (SEQ ID NO: 7):

```
  1 mdrskencis gpvkatapvg gpkrvlvtqq fpcqnplpvn sgqaqrvlcp snssqriplq
 61 aqklvsshkp vqnqkqkqlq atsvphpvsr plnntqkskq plpsapennp eeelaskqkn
121 eeskkrqwal edfeigrplg kgkfgnvyla rekqskfila lkvlfkaqle kagvehqlrr
181 eveiqshlrh pnilrlygyf hdatrvylil eyaplgtvyr elqklskfde qrtatyitel
241 analsychsk rvihrdikpe nlllgsagel kiadfgwsvh apssrrttlc gtldylppem
301 iegrmhdekv dlwslgvlcy eflvgkppfe antyqetykr isrveftfpd fvtegardli
361 srllkhnpsq rpmlrevleh pwitansskp sncqnkesas kqs
```

By "Aurora A polynucleotide" is meant a polynucleotide encoding an Aurora A polypeptide. An exemplary Aurora A polynucleotide sequence is provided at NCBI Accession No. NM_198437. The sequence is provided below (SEQ ID NO: 8):

```
  1 acaaggcagc ctcgctcgag cgcaggccaa tcggctttct agctagaggg tttaactcct
 61 atttaaaaag aagaaccttt gaattctaac ggctgagctc ttggaagact tgggtccttg
121 ggtcgcaggc atcatggacc gatctaaaga aaactgcatt tcaggacctg ttaaggctac
181 agctccagtt ggaggtccaa aacgtgttct cgtgactcag caatttcctt gtcagaatcc
241 attacctgta aatagtggcc aggctcagcg ggtcttgtgt ccttcaaatt cttcccagcg
301 cattcctttg caagcacaaa agcttgtctc cagtcacaag ccggttcaga atcagaagca
361 gaagcaattg caggcaacca gtgtacctca tcctgtctcc aggccactga ataacaccca
421 aaagagcaag cagcccctgc catcggcacc tgaaaataat cctgaggagg aactggcatc
481 aaaacagaaa aatgaagaat caaaaaagag gcagtgggct tggaagact ttgaaattgg
541 tcgccctctg ggtaaggaa agtttggtaa tgtttatttg gcaagagaaa agcaaagcaa
601 gtttattctg gctcttaaag tgttatttaa agctcagctg gagaaagccg gagtggagca
661 tcagctcaga agagaagtag aaatacagtc ccaccttcgg catcctaata ttcttagact
721 gtatggttat ttccatgatg ctaccagagt ctacctaatt ctggaatatg caccacttgg
781 aacagtttat agagaacttc agaaacttc aaagtttgat gagcagagaa ctgctactta
841 tataacagaa ttggcaaatg ccctgtctta ctgtcattcg aagagagtta tcatagaga
901 cattaagcca gagaacttac ttcttggatc agctggagag cttaaaattg cagattttgg
961 gtggtcagta catgctccat cttccaggag gaccactctc tgtggcaccc tggactacct
```

```
-continued
1021    gccccctgaa atgattgaag gtcggatgca tgatgagaag gtggatctct ggagccttgg 1081    agttctttgc tatgaatttt tagttgggaa gcctcctttt gaggcaaaca cataccaaga 1141    gacctacaaa agaatatcac gggttgaatt cacattccct gactttgtaa cagagggagc 1201    cagggacctc atttcaagac tgttgaagca taatcccagc cagaggccaa tgctcagaga 1261    agtacttgaa caccctgga tcacagcaaa ttcatcaaaa ccatcaaatt gccaaaacaa 1321    agaatcagct agcaaacagt cttaggaatc gtgcaggggg agaaatcctt gagccagggc 1381    tgccatataa cctgacagga acatgctact gaagtttatt ttaccattga ctgctgccct 1441    caatctagaa cgctacacaa gaaatatttg ttttactcag caggtgtgcc ttaacctccc 1501    tattcagaaa gctccacatc aataaacatg acactctgaa gtgaaagtag ccacgagaat 1561    tgtgctactt atactggttc ataatctgga ggcaaggttc gactgcagcc gccccgtcag 1621    cctgtgctag gcatggtgtc ttcacaggag gcaaatccag agcctggctg tggggaaagt 1681    gaccactctg ccctgacccc gatcagttaa ggagctgtgc aataaccttc ctagtacctg 1741    agtgagtgtg taacttattg ggttggcgaa gcctggtaaa gctgttggaa tgagtatgtg 1801    attctttta agtatgaaaa taaagatata tgtacagact tgtattttt ctctggtggc 1861    attccttag gaatgctgtg tgtctgtccg gcaccccggt aggcctgatt gggtttctag 1921    tcctccttaa ccacttatct cccatatgag agtgtgaaaa ataggaacac gtgctctacc 1981    tccatttagg gatttgcttg ggatacagaa gaggccatgt gtctcagagc tgttaagggc 2041    ttatttttt aaaacattgg agtcatagca tgtgtgtaaa ctttaaatat gcaaataaat 2101    aagtatctat gtctaaaaaa a
```

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

The terms "binding," "bind," "bound" refer to an interaction between two molecules. The interaction may include a covalent or non-covalent bond. The interaction may also be reversible or irreversible depending on the type of interaction, such as covalent bond formation.

"Detect" refers to identifying the presence, absence or amount of the analyte to be detected.

By "detectable label," "detectable moiety," or "detectable tag" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "disease" is meant any condition or disorder that damages or interferes with the normal function of a cell, tissue, or organ. Examples of diseases include cancers characterized by an increase in an Aurora kinase.

By "effective amount" is meant the amount of a required to ameliorate the symptoms of a disease relative to an untreated patient. The effective amount of active agent(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "epitope tag" is meant a peptide sequence having immunoreactivity. Exemplary epitope tags include, but are not limited to V5-tag, Myc-tag, and HA-tag.

The invention provides a number of targets that are useful for the development of highly specific drugs to treat or a disorder characterized by the methods delineated herein. In addition, the methods of the invention provide a facile means to identify therapies that are safe for use in subjects.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100,200,300, 400, 500, 600, 700, 800, 900, or 1000 nucleotides or amino acids.

By "fusion protein" or "fusion polypeptide" is meant a polypeptide or fragment thereof that combines at least two amino acid sequences that are not naturally contiguous. In some embodiments, a fusion polypeptide comprises an amino acid sequence encoding a monobody of the invention fused to an amino acid sequence encoding a supercharged polypeptide (e.g., a supercharged green fluorescent protein (GFP)). In other embodiments, the fusion polypeptide comprises an amino acid sequence encoding a monobody of the invention fused to an amino acid sequence encoding an epitope tag or a detectable tag.

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence. "Polynucleotide" and "nucleic acid molecule" are used interchangeably herein.

Unless otherwise specified, a "polynucleotide encoding an amino acid sequence," a "polynucleotide encoding a polypeptide," or a "nucleotide sequence encoding an amino acid sequence," includes all nucleotide sequences that are degenerate versions of each other and that encode the same amino acid sequence. The phrase nucleotide sequence that encodes a polypeptide or an RNA may also include introns to the extent that the nucleotide sequence encoding the polypeptide may in some version contain an intron(s).

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "monobody" is meant an antibody mimetic comprising a fibronectin type III domain (FN3) as a molecular scaffold. Monobodies are produced from combinatorial libraries in which portions of the FN3 scaffold are diversified using highly tailored mixtures of amino acids by utilizing phage display and yeast surface display techniques. These techniques have successfully generated a large number of monobodies that have high affinity and high specificity to their respective targets. Monobodies and methods of generating monobodies are further described in, for example, PCT/US2007/078039, U.S. Pat. No. 6,673,901, and PCT/US2011/046160, which are incorporated herein in its entirety.

By "monobody Mb2" is meant a monobody or fragment thereof that binds an allosteric site on Aurora A kinase, increases Aurora A kinase activity, and has at least about 85% amino acid sequence identity to the following amino acid sequence:

```
AuroraA 2 (Mb2)
                                     (SEQ ID NO: 1)
SVSSVPTK LEVVAATPTS LLISWDAFGH QYEPVYYYRI

TYGETGGNSP VQEFTVPGYYSTATISGLKP GVDYTITVYA

WYVDGSYSSP ISINYRT
```

By "monobody Mb44" is meant a monobody or fragment thereof that binds an allosteric site on Aurora A kinase, reduces Aurora A kinase, and that has at least about 85% amino acid sequence identity to the following amino acid sequence:

```
AuroraA 44 (Mb44)
                                     (SEQ ID NO: 2)
SVSSVPTK LEVVAATPTS LLISWDAPAV TVDFYVITYG

ETGGYSYPWQ EFEVPGSKST ATISGLKPGV DYTITVYADY

GQYFYSPISI NYRT
```

By "monobody Mb51" is meant a monobody or fragment thereof that binds an allosteric site on Aurora A kinase and has at least about 85% amino acid sequence identity to the following amino acid sequence:

```
AuroraA 51 (Mb51)
                                     (SEQ ID NO: 3)
SVSSVPTK LEVVAATPTS LLISWDAKPM SYEPVYYYRI

TYGETGGNSP VQEFTVPGYY STATISGLKP GVDYTITVYA

DSMSSYYYSP ISINYRT
```

By "monobody Mb54" is meant a monobody that binds an allosteric site on Aurora A kinase, increases Aurora A kinase activity, and has at least about 85% amino acid sequence identity to the following amino acid sequence:

```
AuroraA 54 (Mb54)
                                     (SEQ ID NO: 4)
SVSSVPTK LEVVAATPTS LLISWDAQTY QMYDYVSYYR

ITYGETGGNS PVQEFTVPGYYSTATISGLK PGVDYTITVY

AEGYYSSYSP ISINYRT
```

By "monobody Mb56" is meant a monobody that binds an allosteric site on Aurora A kinase, decreases Aurora A kinase activity, and has at least 85% amino acid sequence identity to the following amino acid sequence:

```
AuroraA 56 (Mb56)
                                         (SEQ ID NO: 5)
SVSSVPTK LEVVAATPTS LLISWDAMSD WYYWVDYYRI

TYGETGGNSP VQEFTVPGSYSTATISGLKP GVDYTITVYA

SDDVWGDYSP ISINYRT
```

By "monobody Mb60" is meant a monobody that binds an allosteric site on Aurora A kinase, decreases Aurora A kinase activity, and has at least 85% amino acid sequence identity to the following amino acid sequence:

```
AuroraA 60 (Mb60)
                                         (SEQ ID NO: 6)
SVSSVPTK LEVVAATPTS LLISWDAPAV TVVHYVITYG

ETGGNSPVQE FTVPGSKSTATISGLKPGVD YTITVYAIDF

YWGSYSPISI NYRT
```

By "marker" is meant any protein or polynucleotide having an alteration in expression level or activity that is associated with a disease or disorder.

By "mutation" is meant a change in a polypeptide or polynucleotide sequence relative to a wild-type reference sequence. Exemplary mutations include point mutations, missense mutations, amino acid substitutions, and frameshift mutations.

As used herein, "obtaining" as in "obtaining an agent" includes synthesizing, purchasing, or otherwise acquiring the agent.

By "phosphorylation rate" or "rate of phosphorylation" is meant the kinetic rate of a phosphorylation reaction catalyzed by a kinase. An exemplary measure of the rate is the value of a rate constant, k. The rate constant may be determined by plotting the concentrations of phosphorylated substrate against time, and fitting a curve or line to the concentration vs. time data. In some embodiments, the rate constant is determined by determining the slope of a line fit to concentrations of phosphorylated kemptide (substrate of Aurora A kinase) over time. The rate of phosphorylation may be dependent on assay conditions, such as temperature. Thus, an exemplary method of comparing effects of a modulator of Aurora A kinase (e.g., a monobody binding to an allosteric site of Aurora A) on Aurora A's phosphorylation rate is to compare the rates of phosphorylation of Aurora A kinase contacted and not contacted with the modulator under identical or nearly identical assay conditions (e.g., same temperature).

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity.

Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "specifically binds" is meant an agent (e.g., an antibody mimetic or monobody) that recognizes and binds a polypeptide (or fragment thereof) of the invention, but which does not substantially recognize and bind other molecules in a sample, for example, a biological sample, which naturally includes a polypeptide of the invention. An agent may also "specifically bind" to a particular site on a polypeptide, and not bind to other sites of the polypeptide. In some embodiments, an antibody mimetic or monobody specifically binds to an allosteric site (PIF pocket) of Aurora A kinase.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "subject" is meant a mammal, including, but not limited to, a human or non-human mammal, such as a bovine, equine, canine, ovine, or feline.

By "supercharged polypeptide" or "supercharged fragment" is meant a polypeptide or fragment thereof, either engineered or naturally existing, with unusually high positive or net negative net theoretical charge (typically >1 net charge unit per kD of molecular weight). A polypeptide may be engineered to be "supercharged" by substituting residues on the polypeptide for residues having a charge. A polypeptide may also be "supercharged" by fusion to a supercharged polypeptide. In some embodiments, a monobody of the invention is supercharged by fusing the monobody to a supercharged green fluorescent protein (GFP).

Supercharged polypeptides having a negative net theoretical charge are "supernegatively" charged; conversely, supercharged polypeptides having a positive net theoretical charge are "superpositively" charged. Supercharged polypeptides typically exhibit resistance to thermally or chemically induced aggregation. Supercharged polypeptides may also be able to bind and penetrate cells (particularly, mammalian cells), and can therefore deliver nucleic acid or protein cargoes into cells. In some embodiments, a supercharged monobody of the invention (e.g., a monobody fused to a supercharged polypeptide such as supercharged GFP) is delivered to a cell. In some other embodiments, the supercharged monobody is delivered to a cell by cationic liposome mediated delivery.

Methods for engineering supercharged polypeptides for intracellular delivery of proteins into cells and for delivering supercharged polypeptides into a cell are described in, for example, Zuris et al. (2015), Nat. Biotechnol. 33, 73-80 and Liu et al. (2012), Methods Enzymol. 503: 293-319. By "TPX2 polypeptide" is meant a polypeptide or fragment thereof having at least about 85% or greater amino acid identity to the amino acid sequence provided at GenBank Accession Nos. EAW76422. 1, EAW76421. 1, and EAW76420. 1 (various isoforms) and having TPX2 biological activity. Exemplary biological activities of TPX2 include, without limitation, binding to Aurora A kinase and mediating localization of Aurora A kinase to the spindles. The exemplary TPX2 polypeptide sequence at GenBank Accession No. EAW76422.1 is provided below (SEQ ID NO: 9):

```
  1  msqvkssysy dapsdfinfs slddegdtqn idswfeekan lenkllgkng tgglfqgktp 61  lrkanlqqai vtplkpvdnt yykeaekenl veqsipsnac ssleveaais rktpaqpqrr 121  slrlsaqkdl eqkekhhvkm kakrcatpvi ideilpskkm kvsnnkkkpe eegsahqdta 181  eknasspeka kgrhtvpcmp pakqkflkst eeqeleksmk mqqevvemrk kneefkklal 241  agigqpvkks vsqvtksvdf hfrtderikq hpknqeeyke vnftselrkh pssparvtkg 301  ctivkpfnls qgkkrtfdet vstyvplaqq vedfhkrtpn ryhlrskkdd iktgscsvtq 361  agvqwrdhgs lqcptpglkq ssclslpnll pskssvtkic rdpqtpvlqt khraravtck 421  staeleaeel eklqqykfka reldprileg gpilpkkppv kpptepigfd leiekriqer 481  eskkktedeh fefhsrpcpt kiledvvgvp ekkvlpitvp kspafalknr irmptkedee 541  edepvvikaq pvphygvpfk pqipeartve icpfsfdsrd kerqlqkekk ikelqkgevp 601  kfkalplphf dtinlpekkv knvtqiepfc letdrrgalk aqtwkhqlee elrqqkeaac
```

```
661  fkarpntvis qepfvpkkek ksvaeglsgs lvqepfqlat ekrakerqel ekrmaeveaq 721  kaqqleearl qeeeqkkeel arlrrelvhk anpirkyqgl eikssdqplt vpvspkfstr 781  fhc
```

By "TPX2 polynucleotide" is meant a polynucleotide encoding a TPX2 polypeptide.

An exemplary TPX2 polynucleotide sequence is provided at NCBI Accession No. NM_012112. The sequence is provided below (SEQ ID NO: 10):

```
   1  agtggactca cgcaggcgca ggagactaca cttcccagga actccgggcc gcgttgttcg 61  ctggtacctc cttctgactt ccggtattgc tgcggtctgt agggccaatc gggagcctgg 121  aattgctttc ccggcgctct gattggtgca ttcgactagg ctgcctgggt tcaaaatttc 181  aacgatactg aatgagtccc gcggcgggtt ggctcgcgct tcgttgtcag atctgaggcg 241  aggctaggtg agccgtggga agaaaagagg gagcagctag ggcgcgggtc tccctcctcc 301  cggagtttgg aacggctgaa gttcaccttc cagcccctag cgccgttcgc gccgctaggc 361  ctggcttctg aggcggttgc ggtgctcggt cgccgcctag gcggggcagg gtgcgagcag 421  gggcttcggg ccacgcttct cttggcgaca ggattttgct gtgaagtccg tccgggaaac 481  ggaggaaaaa aagagttgcg ggaggctgtc ggctaataac ggttcttgat acatatttgc 541  cagacttcaa gatttcagaa aagggggtgaa agagaagatt gcaactttga gtcagacctg 601  taggcctgat agactgatta accacagaa ggtgacctgc tgagaaaagt ggtacaaata 661  ctgggaaaaa cctgctcttc tgcgttaagt gggagacaat gtcacaagtt aaaagctctt 721  attcctatga tgcccctcg gatttcatca atttttcatc cttggatgat gaaggagata 781  ctcaaaacat agattcatgg tttgaggaga aggccaattt ggagaataag ttactgggga 841  agaatggaac tggagggctt tttcagggca aaactccttt gagaaaggct aatcttcagc 901  aagctattgt cacacctttg aaaccagttg acaacactta ctacaaagag gcagaaaaag 961  aaaatcttgt ggaacaatcc attccgtcaa atgcttgttc ttccctggaa gttgaggcag 1021  ccatatcaag aaaaactcca gcccagcctc agagaagatc tcttaggctt tctgctcaga 1081  aggatttgga acagaaagaa aagcatcatg taaaaatgaa agccaagaga tgtgccactc 1141  ctgtaatcat cgatgaaatt ctaccctcta gaaaatgaa agtttctaac aacaaaaaga 1201  agccagagga agaaggcagt gctcatcaag atactgctga aaagaatgca tcttccccag 1261  agaaagccaa gggtagacat actgtgcctt gtatgccacc tgcaaagcag aagtttctaa 1321  aaagtactga ggagcaagag ctggagaaga gtatgaaaat gcagcaagag gtggtggaga 1381  tgcggaaaaa gaatgaagaa ttcaagaaac ttgctctggc tggaataggg caacctgtga 1441  agaaatcagt gagccaggtc accaaatcag ttgacttcca cttccgcaca gatgagcgaa 1501  tcaaacaaca tcctaagaac caggaggaat ataaggaagt gaactttaca tctgaactac 1561  gaaagcatcc ttcatctcct gcccgagtga ctaagggatg taccattgtt aagcctttca 1621  acctgtccca aggaaagaaa agaacatttg atgaaacagt ttctacatat gtgccccttg 1681  cacagcaagt tgaagacttc cataaacgaa cccctaacag atatcatttg aggagcaaga 1741  aggatgatat taacctgtta ccctccaaat cttctgtgac caagatttgc agagacccac 1801  agactcctgt actgcaaacc aaacaccgtg cacgggctgt gacctgcaaa agtacagcag 1861  agctggaggc tgaggagctc gagaaattgc aacaatacaa attcaaagca cgtgaacttg 1921  atcccagaat acttgaaggt gggcccatct tgcccaagaa accacctgtg aaaccaccca
```

-continued

```
1981  ccgagcctat tggctttgat ttggaaattg agaaaagaat ccaggagcga gaatcaaaga
2041  agaaaacaga ggatgaacac tttgaatttc attccagacc ttgccctact aagattttgg
2101  aagatgttgt gggtgttcct gaaaagaagg tacttccaat caccgtcccc aagtcaccag
2161  cctttgcatt gaagaacaga attcgaatgc ccaccaaaga agatgaggaa gaggacgaac
2221  cggtagtgat aaaagctcaa cctgtgccac attatggggt gcctttttaag ccccaaatcc
2281  cagaggcaag aactgtggaa atatgccctt tctcgtttga ttctcgagac aaagaacgtc
2341  agttacagaa ggagaagaaa ataaaagaac tgcagaaagg ggaggtgccc aagttcaagg
2401  cacttccctt gcctcatttt gacaccatta acctgccaga gaagaaggta aagaatgtga
2461  cccagattga acctttctgc ttggagactg acagaagagg tgctctgaag gcacagactt
2521  ggaagcacca gctggaagaa gaactgagac agcagaaaga agcagcttgt ttcaaggctc
2581  gtccaaacac cgtcatctct caggagccct ttgttcccaa gaaagagaag aaatcagttg
2641  ctgagggcct ttctggttct ctagttcagg aaccttttca gctggctact gagaagagag
2701  ccaaagagcg gcaggagctg gagaagagaa tggctgaggt agaagcccag aaagcccagc
2761  agttggagga ggccagacta caggaggaag agcagaaaaa agaggagctg gccaggctac
2821  ggagagaact ggtgcataag gcaaatccaa tacgcaagta ccagggtctg gagataaagt
2881  caagtgacca gcctctgact gtgcctgtat ctcccaaatt ctccactcga ttccactgct
2941  aaactcagct gtgagctgcg gataccgccc ggcaatggga cctgctctta acctcaaacc
3001  taggaccgtc ttgctttgtc attgggcatg gagagaaccc atttctccag acttttacct
3061  acccgtgcct gagaaagcat acttgacaac tgtggactcc agttttgttg agaattgttt
3121  tcttacatta ctaaggctaa taatgagatg taactcatga atgtctcgat tagactccat
3181  gtagttactt cctttaaacc atcagccggc cttttatatg ggtcttcact ctgactagaa
3241  tttagtctct gtgtcagcac agtgtaatct ctattgctat tgcccttac gactctcacc
3301  ctctccccac ttttttttaaa aattttaacc agaaaataaa gatagttaaa tcctaagata
3361  gagattaagt catggtttaa atgaggaaca atcagtaaat cagattctgt cctcttctct
3421  gcataccgtg aatttatagt taaggatccc tttgctgtga gggtagaaaa cctcaccaac
3481  tgcaccagtg aggaagaaga ctgcgtggat tcatggggag cctcacagca gccacgcagc
3541  aggctctggg tggggctgcc gttaaggcac gttctttcct tactggtgct gataacaaca
3601  gggaaccgtg cagtgtgcat tttaagacct ggcctggaat aaatacgttt tgtctttccc
3661  tcaaaaaaa aaaaaaaaa aaaaa
```

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 1A is a set of plots showing enrichment of pools of monobodies that bind more strongly to Aurora A than Aurora A-TPX2 chimera. Dark grey dots represent 50 nM Aurora A. Light grey dots represent 50 nM AuroraA-TPX2. FIG. 1B is a set of plots showing further refinement of selection by using Y199H and Y199K Aurora A hotspot mutants in negative selection rounds of current monobody pools. FIG. 1C is a set of plots showing binding of isolated monobody clones to Aurora A wild type, Y199H mutant Aurora A, or Y199K mutant Aurora A in a yeast display format. The dissociation constant (Kt) shown in each plot is the Kt for binding to wild type Aurora A FIGS. 2A-2F are plots showing that monobodies in the study described herein (Mb2, Mb44, Mb51, Mb56, Mb54, and Mb60) bind to Aurora A kinase with nanomolar (nM) to low micromolar (μM) affinity. The plots show results of isothermal titration calorimetry experiments to measure the thermodynamics of the binding of monobodies Mb2 (FIG. 2A), Mb44 (FIG. 2B), Mb51 (FIG. 2C), Mb54 (FIG. 2D), Mb56 (FIG. 2E) and Mb60 (FIG. 2F) to dephosphorylated Aurora A ("deP AurA"). The dissociation constant (Kt), heat of enthalpy (MI), and heat of entropy (L1S) of each of the binding reactions are indicated in the respective figures.

FIG. 4A shows the inhibitory WY-motif of the monobody Mb60 (inhibitor of Aurora A kinase) "locks" an aC-helix of Aurora A in an inactive conformation (FIG. 4A). FIG. 4B is a magnified view of the structures depicted in FIG. 4A, showing contact between Mb60 and Aurora A kinase.

FIG. 4C shows that activating anchor points of the monobody Mb54 (activator of Aurora A kinase) push on the aC-helix and coordinate Aurora A's activation loop to keep the kinase in an active conformation. FIG. 4D shows a magnified view of the anchor points of Mb54.

FIG. 4E shows how monobodies Mb60 (inhibitor) and Mb54 (activator) shift equilibria between active and inactive Aurora A kinase.

FIG. 6A is a plot showing Aurora A kinase activity when Aurora A kinase is incubated with monobody Mb60 ("Mb60"), monobody Mb60 fused to supercharged GFP ("sGFP Mb60"), and no monobody ("no Mb"). FIG. 6A shows that Mb60 and sGFP-Mb60 both inhibit Aurora A kinase activity, but Mb60 more strongly inhibits Aurora A kinase than sGFP-Mb60. FIG. 6B is a set of plots depicting measurement of the thermodynamics of binding of Mb60 fused to supercharged GFP to Aurora A kinase (FIG. 6B) and binding of Mb60 to Aurora A kinase (FIG. 6C) using isothermal titration calorimetry. The dissociation constant (Kt) of the binding reaction is indicated in the respective plots.

FIG. 7A depicts the optimization of delivery of sGFP-Mb60 ("sGFP_Mb60") to cells. To optimize delivery, various concentrations (1 nM, 25 nM, 50 nM, and 500 nM) of sGFP-Mb60 were incubated with various amounts of cationic liposomes (2 μl, 3 μl, and 4 μl), and delivery of sGFP-Mb60 was assayed by live cell imaging. Optimaa delivery was achieved at a combination of 50 nM sGFP-Mb60 and 4 μl cationic liposomes (FIG. 7B). FIG. 7C shows monitored delivery of sGFP-Mb60 to cells, at various incubation time points (0 hr, 1 hr, 7 hr, and 24 hr).

FIG. 8B is a set of micrographs depicting high magnification views of subsets of micrographs in FIG. SA The micrographs show DNA, Aurora A kinase ("AurA"), and sGFP-Mb60 in a cell during interphase (left column), prophase (middle column), and metaphase (right column). FIGS. 8C-8E are sets of micrographs further showing co-localization of sGFP-Mb60 with Aurora Akinase during metaphase. In each of FIGS. 8C-8E, the set of micrographs on the left show high magnification views of DNA, Aurora A kinase ("AurA"), and sGFP-Mb60 in a cell. The micrograph on the right of each of FIGS. 8C-8E is a low magnification view of the micrographs in the left, showing DNA (FIG. SC), Aurora A kinase (FIG. SD), and sGFP-Mb60 (FIG. SE). FIG. SF is a set of micrographs showing a low magnification view of micrographs in FIG. SA showing DNA, Aurora A kinase, and sGFP-Mb60 in a cell in prometaphase. FIG. 8G is a set of micrographs showing a low magnification view of micrographs in FIG. SA showing DNA, Aurora A kinase, and sGFP-Mb60 in a cell in interphase.

FIG. 10 shows a 12-well plate containing samples of human embryonic kidney (HEK) cells with sGFP-Mb60 delivered via liposomes and appropriate control cells. Cell death in cell samples treated with sGFP-Mb60 (inhibitor of Aurora A kinase activity) was observed.

DETAILED DESCRIPTION OF THE INVENTION

Figure 1A:
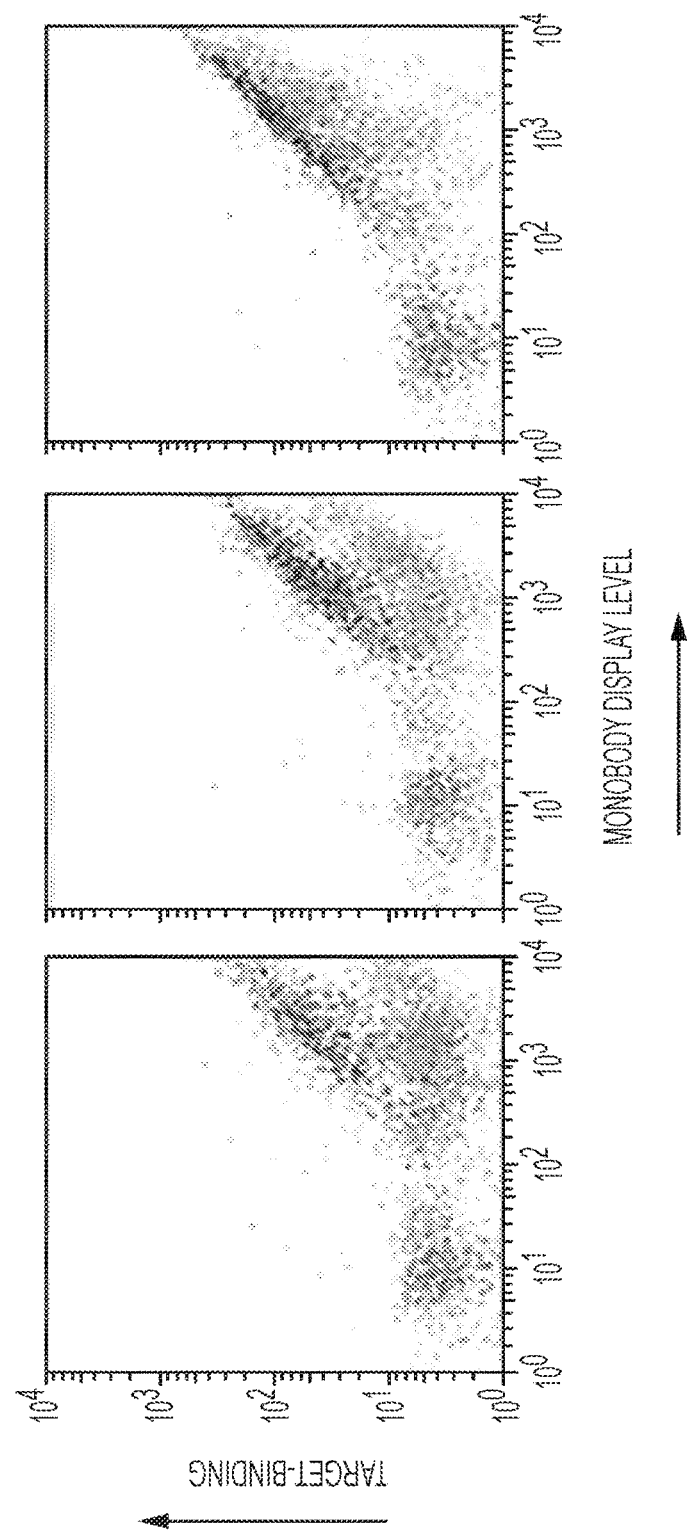
FIGS. 1A-1C are sets of exemplary plots depicting the monobody selection strategy used to generate monobodies in a study described herein.

The invention features compositions and methods that are useful for modulating kinase activity in a cell. The invention is based, at least in part, on the discovery that monobodies generated to specifically bind to a PIF pocket in Aurora A kinase differentially modulated Aurora A's kinase activity.

The monobodies were found to activate or inhibit kinase activity of Aurora A, with varying strengths of activation or inhibition. Treatment of cells with monobodies inhibiting Aurora A activity was found to disrupt TPX2 binding to Aurora A, disrupt Aurora A localization to the spindles, and trigger cell death.

Antibody mimetics targeting an allosteric site (PIF pocket) of Aurora A kinase Aurora A is an oncoprotein that is overexpressed in a multitude of cancers. Aurora A kinase is implicated in the regulation of mitotic entry and progression, spindle assembly, and spindle stability. Deregulation of Aurora A's kinase activity can result in defects in spindle assembly, chromosome alignment, and cytokinesis. Without intending to be bound by theory, overexpression of Aurora A kinase is believed to contribute to tumor formation, growth, and proliferation.

Thus, ways to inhibit Aurora A via small molecules have been actively pursued by researchers in both academia and industry. In particular, efforts to develop small molecule inhibitors of Aurora A's kinase activity have focused primarily on targeting Aurora A's ATP-binding site. However, these efforts generally have not focused on targeting the PIF pocket of Aurora A, an allosteric site on Aurora A The allosteric site of Aurora A is bound by TPX2. In order to localize to the spindle microtubules and allow for proper progression of mitosis, Aurora A must bind to TPX2, and must be allosterically activated by TPX2. Binding of TPX2 to the PIF pocket of Aurora A allosterically activates Aurora A. Inhibitors of kinase activity of Aurora A that bind to the PIF pocket in Aurora A are not previously known.

Targeting the allosteric site (i.e., PIF pocket) of Aurora A kinase offers a more attractive strategy for inhibiting Aurora A's kinase activity. Unlike the ATP-binding pocket (the major target to date for kinase inhibitors as cancer drugs), which is highly conserved across kinases, the allosteric PIF pocket of human protein kinases is variable among different kinases, thereby offering the potential of developing much more specific kinase inhibitors. Using a highly specific kinase inhibitor is less likely to result in side effects.

Accordingly, the present invention features antibody mimetics, such as monobodies, that specifically bind to an allosteric site of Aurora A kinase. Monobodies are not routinely explored in the kinase field. Not many monobodies are known to bind kinases, although few examples are known (e.g., monobodies that bind to Abl).

In some embodiments, the antibody mimetic or monobody specifically binds to the PIF pocket of Aurora A kinase. In some other embodiments, binding of the antibody mimetic or monobody disrupts binding of TPX2 to Aurora A kinase The PIF pocket is a highly malleable interface that is ideal for drug discovery. Because the interaction surface between Aurora A and TPX2 is extensive and lacks the classic, small, confined, binding pocket that is preferred when designing small molecule inhibitors, an antibody mimetic such as a monobody could mimic best the TPX2 interaction and thus displace this protein. Further, due to phage display selection, antibody mimetics or monobodies having high selectivity and high affinity to the activation pocket (PIF pocket) of Aurora A could be generated. Also, using a small protein (such as a monobody) with high specificity for Aurora A instead of a small molecule compound (which tend to have low specificity) to inhibit Aurora A's kinase activity poses a lower risk of side effects.

Antibody mimetics or monobodies of the invention are highly specific to Aurora A kinase and have high affinity to Aurora A kinase. In some embodiments, antibody mimetics or monobodies of the invention bind Aurora A with affinities of at least about 1 nM, least about 5 nM, at least about 10 nM, least about 50 nM, least about 100 nM, least about 500 nM, least about 1 µM, at least about 5 µM, or at least about 10 µM.

Antibody mimetics or monobodies of the invention are also capable of differentially modulating the kinase activity of Aurora A kinase. In some embodiments, binding of the antibody mimetic or monobody to the allosteric site alters an activity of Aurora A kinase. In some embodiments, the antibody mimetic or monobody modulates Aurora A's activity such that the rate of phosphorylation of a substrate by Aurora A kinase is increased by at least about 1.1. fold, at least about 1.2 fold, at least about 1.3 fold, at least about 1.4 fold, at least about 1.5 fold, at least about 1.6 fold, at least about 1.7 fold, at least about 1.8 fold, at least about 1.9 fold, at least about 2 fold, at least about 3 fold, at least about 4 fold, at least about 5 fold, at least about 6 fold, at least about 7 fold, at least about 8 fold, at least about 9 fold, at least about 10 fold, at least about 15 fold, and at least about 20 fold relative to a reference rate. In some other embodiments, the antibody mimetic or monobody modulates Aurora A's activity such that the rate of phosphorylation of a substrate by Aurora A kinase is decreased by at least about 1.1 fold, at least about 1.2 fold, at least about 1.3 fold, at least about 1.4 fold, at least about 1.5 fold, at least about 1.6 fold, at least about 1.7 fold, at least about 1.8 fold, at least about 1.9 fold, at least about 2 fold, at least about 3 fold, at least about 4 fold, at least about 5 fold, at least about 6 fold, at least about 7 fold, at least about 8 fold, at least about 9 fold, or at least about 10 fold relative to a reference rate. The reference rate may be, for example, the rate of phosphorylation of unbound Aurora A kinase (e.g. Aurora A kinase that is not contacted with any agent, such as TPX2) measured under substantially identical conditions (e.g., same temperature).

In particular embodiments, the antibody mimetic or monobody binds to the PIF pocket of Aurora A and inhibits or decreases Aurora A's kinase activity. In some embodiments, when an inhibitory antibody mimetic or monobody is added to an Aurora A-catalyzed reaction, the rate of Aurora A's phosphorylation of a substrate is decreased by at least about 1.1 fold, at least about 1.2 fold, at least about 1.3 fold, at least about 1.4 fold, at least about 1.5 fold, at least about 1.6 fold, at least about 1.7 fold, at least about 1.8 fold, at least about 1.9 fold, at least about 2 fold, at least about 3 fold, at least about 4 fold, at least about 5 fold, at least about 6 fold, at least about 7 fold, at least about 8 fold, at least about 9 fold, or at least about 10 fold. In other embodiments, the antibody or monobody binds to the PIF pocket of Aurora A and activates Aurora A's kinase activity. In particular embodiments, when an activating antibody mimetic or monobody is added to an Aurora A-catalyzed reaction, the rate of Aurora A's phosphorylation of a substrate is increased by at least about 1.1. fold, at least about 1.2 fold, at least about 1.3 fold, at least about 1.4 fold, at least about 1.5 fold, at least about 1.6 fold, at least about 1.7 fold, at least about 1.8 fold, at least about 1.9 fold, at least about 2 fold, at least about 3 fold, at least about 4 fold, at least about 5 fold, at least about 6 fold, at least about 7 fold, at least about 8 fold, at least about 9 fold, at least about 10 fold, at least about 15 fold, and at least about 20 fold.

Antibody mimetics or monobodies of the invention were generated using a novel screening assay. The screening assay comprised (a) contacting a candidate antibody mimetic with an Aurora A kinase having an unbound allosteric site, (b) contacting the candidate antibody mimetic with an Aurora A kinase having a bound allosteric site or an Aurora A kinase mutant that has a mutation within an allosteric site, and (c) measuring binding of the candidate antibody mimetic with Aurora A kinase in step (a) and in step (b). A candidate antibody mimetic having an increased binding to Aurora A kinase in step (a) relative to step (b) was then identified as a potential antibody mimetic that specifically bound to an allosteric site (PIF pocket) of Aurora A kinase.

The screening assay for generating antibody mimetics or monobodies of the invention overcomes problems associated with generation of monobodies binding to other sites of Aurora A (e.g., Aurora A's ATP binding site). As described elsewhere herein, antibody mimetics or monobodies specifically binding a target are typically generated by sorting libraries of antibody mimetics for those that bind the desired target (e.g., Aurora A). However, merely selecting antibody mimetics or monobodies for those binding to Aurora A generates monobodies that potentially bind to any site on Aurora A, rather than monobodies that bind specifically to the allosteric site (PIF pocket) of Aurora A Thus, to select only those antibody mimetics or monobodies that specifically bound the allosteric site (PIF pocket) of Aurora A, in addition to performing a first round of selection for antibody mimetics or monobodies binding to Aurora A, a second round of selection for antibody mimetics or monobodies that did not bind to an Aurora A-TPX2 chimeric construct (i.e., Aurora A kinase having a bound PIF pocket or allosteric site) or an Aurora A kinase mutant that has a mutation within an allosteric site was performed. The second round of negative selection for monobodies using the mutant Aurora A ensured that monobodies binding to other portions of Aurora A (e.g., ATP-binding site) were eliminated from the screen, thus enriching the pool of monobodies with only those binding to the allosteric site (PIF pocket) of Aurora A kinase.

The structure of the antibody mimetics or monobodies of the present invention are advantageous for multiple applications because they (1) lack disulfide bonds, rendering them resistant against reducing agents; (2) are very stable even at high temperature; and (3) can be produced in a bacterial expression system with yields of up to 50-100 mg per liter of culture. Moreover, because they are derived from the endogenous human protein fibronectin, which is non-immunogenic, it is believed that the antibody mimetics or monobodies will not elicit an immune response. As a small, single-chain molecule, DNA encoding the antibody mimetics or monobodies can be incorporated into gene delivery vectors (e.g. viral vectors, liposomes) for cell or tissue-specific gene expression. As a result of these properties, the antibody mimetics or monobodies of the present invention can be used to treat or prevent a number of cancers or Aurora A-associated diseases or disorders as well as for diagnostic imaging of Aurora A-expressing tissues (e.g., tumors or cancers overexpressing Aurora A). Accordingly, the invention provides methods of producing recombinant polypeptides comprising antibody mimetics or monobodies specifically binding to Aurora A's PIF pocket and methods of using these polypeptides to treat a cancer or an Aurora A-associated disease.

Recombinant Polypeptide Expression

The invention provides recombinant antibody mimetics (in particular, monobodies) and fusion polypeptides comprising the antibody mimetics, which are useful for treating a cancer or inhibiting growth and/or proliferation of a cancer in a subject. When delivered to a cell (particularly a cancer cell), the polypeptides of the invention modulate or inhibit Aurora A's kinase activity in a cell, disrupt TPX2 binding to Aurora A kinase, and/or disrupt Aurora A's localization to the spindles. Inhibition of Aurora A's kinase activity and/or disruption of any of Aurora A's other activities (e.g., binding with TPX2 or localization to the spindles) causes cell death.

Recombinant polypeptides of the invention are produced using virtually any method known to the skilled artisan. Typically, recombinant polypeptides are produced by transformation of a suitable host cell with all or part of a polypeptide-encoding nucleic acid molecule or fragment thereof in a suitable expression vehicle. Accordingly, the invention provides methods of producing a polypeptide of the invention, the method comprising (a) heterologously expressing an expression vector comprising a polynucleotide encoding the polypeptide in a host cell; and (b) isolating the polypeptide from the host cell.

Those skilled in the field of molecular biology will understand that any of a wide variety of expression systems may be used to provide the recombinant protein. The precise host cell used is not critical to the invention. A polypeptide of the invention may be produced in a prokaryotic host (e.g., *E. coli*) or in a eukaryotic host (e.g., *Saccharomyces cerevisiae*, insect cells, e.g., Sf21 cells, or mammalian cells, e.g., NIH 3T3, HeLa, COS cells). Such cells are available from a wide range of sources (e.g., the American Type Culture Collection, Rockland, Md.; also, see, e.g., Ausubel et al., Current Protocol in Molecular Biology, New York: John Wiley and Sons, 1997). The method of transformation or transfection and the choice of expression vehicle will depend on the host system selected. Transformation and transfection methods are described, e.g., in Ausubel et al. (supra); expression vehicles may be chosen from those provided, e.g., in Cloning Vectors: A Laboratory Manual (P. H. Pouwels et al., 1985, Supp. 1987).

A variety of expression systems exist for the production of the polypeptides of the invention. Expression vectors useful for producing such polypeptides include, without limitation, chromosomal, episomal, and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof.

In some embodiments, the polypeptides of the invention are produced in a bacterial expression system with yields of up to 50-100 mg per liter of culture. One particular bacterial expression system for polypeptide production is the *E. coli* pET expression system (e.g., pET-28) (Novagen, Inc., Madison, Wis.). According to this expression system, DNA encoding a polypeptide is inserted into a pET vector in an orientation designed to allow expression. Since the gene encoding such a polypeptide is under the control of the T7 regulatory signals, expression of the polypeptide is achieved by inducing the expression of T7RNA polymerase in the host cell. This is typically achieved using host strains that express T7 RNA polymerase in response to IPTG induction. Once produced, recombinant polypeptide is then isolated according to standard methods known in the art, for example, those described herein.

Another bacterial expression system for polypeptide production is the pGEX expression system (Pharmacia). This system employs a GST gene fusion system that is designed for high-level expression of genes or gene fragments as fusion proteins with rapid purification and recovery of functional gene products. The protein of interest is fused to the carboxyl terminus of the glutathione S-transferase protein from *Schistosoma japonicum* and is readily purified from bacterial lysates by affinity chromatography using Glutathione Sepharose 4B. Fusion proteins can be recovered under mild conditions by elution with glutathione. Cleavage of the glutathione S-transferase domain from the fusion protein is facilitated by the presence of recognition sites for site-specific proteases upstream of this domain. For example, proteins expressed in pGEX-2T plasmids may be cleaved with thrombin; those expressed in pGEX-3X may be cleaved with factor Xa.

Alternatively, recombinant polypeptides of the invention are expressed in *Pichia pastoris*, a methylotrophic yeast. *Pichia* is capable of metabolizing methanol as the sole carbon source. The first step in the metabolism of methanol is the oxidation of methanol to formaldehyde by the enzyme, alcohol oxidase. Expression of this enzyme, which is coded for by the AOX1 gene is induced by methanol. The AOX1 promoter can be used for inducible polypeptide expression or the GAP promoter for constitutive expression of a gene of interest.

Once the recombinant polypeptide of the invention is expressed, it is isolated, for example, using affinity chromatography. In one example, an antibody (e.g., produced as described herein) raised against a polypeptide of the invention may be attached to a column and used to isolate the recombinant polypeptide. In some embodiments, to facilitate purification of the recombinant polypeptide, the polypeptide comprises an epitope tag fused to antibody mimetic or monobody. The polypeptide is then isolated using an antibody against the epitope tag. Lysis and fractionation of polypeptide-harboring cells prior to affinity chromatography may be performed by standard methods (see, e.g., Ausubel et al., supra). Alternatively, the polypeptide is isolated using a sequence tag, such as a hexahistidine tag, that binds to nickel column. Once isolated, the recombinant protein can, if desired, be further purified, e.g., by high performance liquid chromatography (see, e.g., Fisher, Laboratory Techniques In Biochemistry and Molecular Biology, eds., Work and Burdon, Elsevier, 1980). Polypeptides of the invention, particularly short peptide fragments, can also be produced by chemical synthesis (e.g., by the methods described in Solid Phase Peptide Synthesis, 2nd ed., 1984 The Pierce Chemical Co., Rockford, Ill.). These general techniques of polypeptide expression and purification can also be used to produce and isolate useful peptide fragments or analogs (described herein).

In addition, or in the alternative, the polypeptides or fusion polypeptides of the invention may be produced using chemical methods to synthesize the desired amino acid sequence, in whole or in part. For example, polypeptides can be synthesized by solid phase techniques, cleaved from the resin, and purified by preparative high performance liquid chromatography (e.g., Creighton (1983) Proteins: Structures And Molecular Principles, WH Freeman and Co, New York N.Y.). The composition of the synthetic polypeptides may be confirmed by amino acid analysis or sequencing (e.g., the Edman degradation procedure). Additionally, the amino acid sequence of a fusion polypeptide of the invention, or any part thereof, may be altered during direct synthesis and/or combined using chemical methods with a sequence from other subunits, or any part thereof, to produce a variant polypeptide.

Assays for Activity of Fusion Polypeptide

Any of the kinase activity and/or kinetics or binding assays known in the art or described herein may be used to measure the binding or effect on Aurora A kinase of the fusion polypeptides of the invention. For example, the inhibitory or activating effect of a fusion polypeptide comprising a monobody of the invention fused to a supercharged polypeptide (e.g., a supercharged GFP) may be measured by contacting the fusion polypeptide with Aurora A kinase in the presence of a substrate of Aurora A kinase (e.g., ATP, kemptide), and measuring a rate of phosphorylation of the substrate. The measured rate may be compared with a reference rate. The reference rate may be, for example, the rate of phosphorylation of the substrate by Aurora A kinase contacted with a monobody not fused to any other polypeptide. The reference rate may also be the rate of phosphorylation of the substrate by Aurora A kinase not contacted with any agent.

The rates are then compared to determine whether the fusion polypeptide comprising the monobody has similar activity to the monobody by itself (e.g., increases or decreases Aurora A's kinase activity to the same degree, or to a lesser or greater degree). In some embodiments, the fusion polypeptide comprising a monobody fused to a supercharged polypeptide (e.g., a supercharged GFP) has activity that is identical or similar to the monobody not fused to another polypeptide. For example, a fusion polypeptide comprising a monobody fused to a supercharged polypeptide decreases or increases Aurora A's kinase activity (e.g., rate of phosphorylation of a substrate) to a degree within about 5%, about 10%, or about 20% of the decrease or increase of Aurora A's kinase activity by the monobody by itself. In some embodiments, the fusion polypeptide comprising an inhibitory monobody fused to a supercharged polypeptide inhibits Aurora A's kinase activity to a lesser degree than inhibition of Aurora A kinase activity by the monobody by itself (i.e., not fused to another polypeptide).

Binding affinity of a fusion polypeptide to Aurora A kinase may also be measured according to methods known in the art or described herein. The affinity of binding of the fusion polypeptide comprising a monobody to Aurora A kinase may be compared to a reference affinity (e.g., the affinity of binding of the monobody by itself (not fused to another polypeptide) to Aurora A kinase). In some embodiments, the affinity of binding of the fusion polypeptide comprising a monobody fused to a supercharged polypeptide is within about 5%, about 10% or about 20% of the affinity of binding of the monobody by itself (i.e., not fused to another polypeptide) to Aurora A kinase.

Methods of Treatment

The present invention provides methods using polypeptides comprising antibody mimetics, monobodies, or fragments thereof, for treatment of cancer. As described herein, Aurora A kinase is overexpressed in many cancer types and is believed to contribute to cancer formation and growth. Antibody mimetics or monobodies of the invention are able to (1) inhibit activity of Aurora A, and (2) disrupt Aurora A localization to the spindles. As described herein, inhibition of Aurora A's kinase activity and disruption of localization of Aurora A to the spindles in a cell (in particular, a cancer cell) triggers cell death.

Thus, the present invention provides methods of inhibiting proliferation and/or reducing survival of a cancer cell and methods of treating a cancer or symptoms thereof, which comprise administering a therapeutically effective amount of a pharmaceutical composition comprising an antibody mimetic, monobody, of fragment thereof (or a polynucleotide encoding the antibody mimetic, monobody, of fragment thereof), herein to a subject (e.g., a mammal such as a human). One embodiment is a method of treating a subject suffering from or susceptible to a cancer or disorder or symptom thereof, particularly a cancer associated with overexpressed Aurora A kinase or deregulated Aurora A kinase activity. The method includes the step of administering to the mammal a therapeutic amount of the antibody mimetic, monobody, or polynucleotide herein sufficient to treat the disease or disorder or symptom thereof, under conditions such that the disease or disorder is treated.

The methods herein include administering to the subject (including a subject identified as in need of such treatment) an effective amount of an antibody mimetic, monobody, or polynucleotide described herein, or a composition described herein to produce such effect. Identifying a subject in need of such treatment can be in the judgment of a subject or a health care professional and can be subjective (e.g. opinion) or objective (e.g. measurable by a test or diagnostic method).

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

The therapeutic methods of the invention (which include prophylactic treatment) in general comprise administration of a therapeutically effective amount of the agents herein, such as an antibody mimetic, monobody, of fragment thereof (or a polynucleotide encoding the antibody mimetic, monobody, of fragment thereof) herein to a subject (e.g., animal, human) in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, activity or expression of Aurora A kinase, family history, and the like). The therapeutic agents herein may be also used in the treatment of any other disorders in which Aurora A kinase may be implicated.

In one embodiment, the invention provides a method of monitoring treatment progress. The method includes the step of determining a level of activity of a kinase (e.g., any target delineated herein modulated by an antibody mimetic or monobody herein, such as Aurora A kinase) or diagnostic measurement (e.g., screen, assay) in a subject suffering from or susceptible to a disorder or symptoms thereof associated with Aurora A kinase, in which the subject has been administered a therapeutic amount of an antibody mimetic, monobody, or polynucleotide herein sufficient to treat the disease or symptoms thereof. An activity of Aurora A may include, for example, Aurora A's kinase activity, localization to the spindles, or functions during mitotic progress. The activity level of Aurora A determined in the method can be compared to known activity levels of Aurora A in either healthy normal controls or in other afflicted patients to establish the subject's disease status. In preferred embodiments, a second activity level of Aurora A in the subject is determined at a time point later than the determination of the first level, and the two levels are compared to monitor the course of disease or the efficacy of the therapy. In certain preferred embodiments, a pre-treatment level of Aurora A activity in the subject is determined prior to beginning treatment according to this invention; this pre-treatment level of Aurora A activity can then be compared to the level of activity of Aurora A in the subject after the treatment commences, to determine the efficacy of the treatment.

Methods of Delivery

Antibody mimetics or monobodies of the invention, which are useful for specifically modulating or inhibiting Aurora A kinase in a cell, may be delivered to a cell (particularly a cancer cell) in any manner such that the antibody mimetic or monobody is in functional form in the cell. The antibody mimetic or monobody may be delivered to cells as polypeptides. Alternatively, a polynucleotide encoding an amino acid sequence of the antibody mimetic or monobody may be delivered to cells for heterologous expression of the antibody mimetic or monobody in the cells. Thus, the present invention features monobodies or polypeptides delivered to a cell by contacting the cell with a composition comprising the monobody or polypeptide or by heterologously expressing the monobody or polypeptide in the cell.

Intracellular Delivery of Polypeptides

Polypeptides of the invention, such as antibody mimetics or monobodies, may be delivered intracellularly to cells. The polypeptide must be delivered to the cells of a subject in a form in which they can be taken up so that therapeutically effective levels of the antibody mimetic or monobody, or fragment thereof, is in functional form in the cells.

Methods of intracellular delivery of polypeptides are known to one of skill in the art.

Exemplary methods of intracellular delivery of polypeptides include, without limitation, incorporation of the polypeptide into a liposome. Liposomes are phospholipid vesicles with sizes varying from 50 to 1000 nm, which can be loaded with polypeptides or other agents. Liposomal intracellular delivery of polypeptides into cells typically relies on endocytosis of the liposome-encapsulated polypeptide into the cell. Examples of suitable liposomes for intracellular delivery of polypeptides may be pH-sensitive liposomes. Such liposomes are made of pH-sensitive components; after being endocytosed in intact form, the liposome fuses with the endovascular membrane under lowered pH inside the endosome and destabilizes it, thereby releasing the contents (including the polypeptides encapsulated in the liposome) into the cytoplasm. The liposomes may also be further modified to enhance their stability or lifetime during circulation (e.g., by PEGylated liposomes). Liposomes may also be modified to specifically target antigens (e.g., "immunoliposomes" or liposomes embedded with antibodies an antigen). Antibody-bearing liposomes may have the advantages of targetability and facilitated uptake via receptor-mediated endocytosis.

Other methods of intracellular delivery of polypeptides include, without limitation, use of cell penetrating peptides (CPPs). A cell penetrating peptide or "CPP" is a protein or peptide that can translocate through cellular membranes. A polypeptide for delivery into a cell is fused with a CPP, thereby enabling or enhancing delivery of the polypeptide fusion into the cell. Cell penetrating peptides include, for example, a trans-activating transcriptional activator (TAT) from HIV-1, Antenapedie (Antp, a transcription factor in *Drosophila*), and VP22 (a herpes virus protein).

Another exemplary method for intracellular delivery of polypeptides of the invention is the use of supercharged proteins. Supercharged proteins or supercharged polypeptides are a class of engineered or naturally existing polypeptides having an unusually high positive or negative net theoretical charge. Membranes of cells are typically negatively charged.

Superpositively charged polypeptides are able to penetrate cells (particularly mammalian cells), and associating cargo with superpositively charged polypeptides (e.g., polypeptides or polynucleotides) can enable functional delivery of these macromolecules into cells, in vitro or in vivo. Methods of generating supercharged polypeptides and using supercharged polypeptides for intracellular polypeptide delivery are described in further detail in, for example, Zuris et al. Nat. Biotechnol. (2015) 33:73-80 and Liu et al. Methods Enzymol. 2012, 503: 293-319.

The present invention features a monobody fused to a supercharged fragment sufficient to mediate intracellular delivery of the polypeptide. Supercharged polypeptides (or fusion polypeptides) may also be used in combination with charged liposomes to enable efficient delivery of polypeptides in a cell. In some embodiments, the polypeptides (antibody mimetics or monobodies) of the invention are delivered intracellularly by fusion of the polypeptide with a supercharged polypeptide (e.g., supercharged green fluorescent protein (GFP)). The supercharged polypeptide may be supernegatively charged. In some other embodiments, the polypeptide fusions (e.g. antibody mimetic or monobody fused to a supercharged polypeptide) are incorporated into a liposome. In particular embodiments, the liposome is a cationic liposome. The cationic liposomes bearing supercharged antibody mimetic or monody fusion are contacted with cells and efficiently delivered into the cells in functional form Polynucleotide Therapy Another therapeutic approach for treating a cancer or a disease associated with AuroraA is polynucleotide therapy using a polynucleotide encoding an antibody mimetic or monobody of the invention, or an antigen binding fragment thereof. Thus, provided herein are isolated polynucleotides encoding an antibody mimetic or monobody of the invention, or an antigen binding fragment thereof. Expression of such polynucleotides or nucleic acid molecules in a cancer cell is expected to reduce survival of the cell and/or increase cell death. Such nucleic acid molecules can be delivered to cells of a subject having a cancer. The nucleic acid molecules must be delivered to the cells of a subject in a form in which they can be taken up so that therapeutically effective levels of the antibody mimetic or monobody, or fragment thereof, can be produced.

Transducing viral (e.g., retroviral, adenoviral, and adeno-associated viral) vectors can be used for somatic cell gene therapy, especially because of their high efficiency of infection and stable integration and expression (see, e.g., Cayouette et al., Human Gene Therapy 8:423-430, 1997; Kido et al., Current Eye Research 15:833-844, 1996; Bloomer et al., Journal of Virology 71:6641-6649, 1997; Naldini et al., Science 272:263-267, 1996; and Miyoshi et al., Proc. Natl. Acad. Sci. U.S.A. 94:10319, 1997). For example, a polynucleotide encoding an antibody mimetic or monobody, or a fragment thereof, can be cloned into a retroviral vector and expression can be driven from its endogenous promoter, from the retroviral long terminal repeat, or from a promoter specific for a target cell type of interest. Other viral vectors that can be used include, for example, a vaccinia virus, a bovine papillomavirus, or a herpes virus, such as Epstein-Barr Virus (also see, for example, the vectors of Miller, Human Gene Therapy 15-14, 1990; Friedman, Science 244:1275-1281, 1989; Eglitis et al., BioTechniques 6:608-614, 1988; Tolstoshev et al., Current Opinion in Biotechnology 1:55-61, 1990; Sharp, The Lancet 337:1277-1278, 1991; Cornetta et al., Nucleic Acid Research and Molecular Biology 36:311-322, 1987; Anderson, Science 226:401-409, 1984; Moen, Blood Cells 17:407-416, 1991; Miller et al., Biotechnology 7:980-990, 1989; Le Gal La Salle et al., Science 259:988-990, 1993; and Johnson, Chest 107:77S-83S, 1995).

Retroviral vectors are particularly well developed and have been used in clinical settings (Rosenberg et al., N. Engl. J. Med 323:370, 1990; Anderson et al., U.S. Pat. No. 5,399,346), In some embodiments, a viral vector is used to administer a polynucleotide encoding an antibody mimetic or monobody (or fragment thereof) systemically.

Non-viral approaches can also be employed for the introduction of therapeutic to a cell of a patient requiring inhibition of a cancer or induction of cell death in a cancer. For example, a nucleic acid molecule can be introduced into a cell by administering the nucleic acid in the presence of lipofection (Feigner et al., Proc. Natl. Acad. Sci. U.S.A. 84:7413, 1987; Ono et al., Neuroscience Letters 17:259, 1990; Brigham et al., Am. J. Med. Sci. 298:278, 1989; Staubinger et al., Methods in Enzymology 101:512, 1983), asialoorosomucoid-polylysine conjugation (Wu et al., Journal of Biological Chemistry 263:14621, 1988; Wu et al., Journal of Biological Chemistry 264:16985, 1989), or by micro-injection under surgical conditions (Wolff et al., Science 247:1465, 1990). Preferably the nucleic acids are administered in combination with a liposome and protamine.

Gene transfer can also be achieved using non-viral means involving transfection in vitro. Such methods include the use of calcium phosphate, DEAE dextran, electroporation, and protoplast fusion. Liposomes can also be potentially beneficial for delivery of DNA into a cell. Transplantation of normal genes into the affected tissues of a patient can also be accomplished by transferring a normal nucleic acid into a cultivatable cell type ex vivo (e.g., an autologous or heterologous primary cell or progeny thereof), after which the cell (or its descendants) are injected into a targeted tissue.

cDNA expression for use in polynucleotide therapy methods can be directed from any suitable promoter (e.g., the human cytomegalovirus (CMV), simian virus 40 (SV40), or metallothionein promoters), and regulated by any appropriate mammalian regulatory element. For example, if desired, enhancers known to preferentially direct gene expression in specific cell types can be used to direct the expression of a nucleic acid. The enhancers used can include, without limitation, those that are characterized as tissue- or cell-specific enhancers. Alternatively, if a genomic clone is used as a therapeutic construct, regulation can be mediated by the cognate regulatory sequences or, if desired, by regulatory sequences derived from a heterologous source, including any of the promoters or regulatory elements described above.

Pharmaceutical Compositions

The present invention features compositions useful for treating a cancer in a subject. In some embodiments, the composition comprises an antibody mimetic, monobody, or fragment thereof, that specifically binds to an allosteric site (PIF pocket) of Aurora A kinase. In some other embodiments, the composition comprises a polynucleotide encoding an amino acid sequence of the antibody mimetic, monobody, or fragment thereof. In particular embodiments, the composition further comprises a liposome.

The administration of a composition comprising an antibody mimetic, monobody, or polynucleotide herein for the treatment of a cancer may be by any suitable means that results in a concentration of the therapeutic that, combined with other components, is effective in ameliorating, reducing, or stabilizing a cancer in a subject. The composition may be administered systemically, for example, formulated in a pharmaceutically-acceptable buffer such as physiological saline. Preferable routes of administration include, for example, subcutaneous, intravenous, intraperitoneally, intramuscular, or intradermal injections that provide continuous, sustained levels of the agent in the patient. The amount of the therapeutic agent to be administered varies depending upon the manner of administration, the age and body weight of the patient, and with the clinical symptoms of the cancer. Generally, amounts will be in the range of those used for other agents used in the treatment of cancer or other diseases associated with Aurora A kinase, although in certain instances lower amounts will be needed because of the increased specificity of the agent. A composition is administered at a dosage that inhibits Aurora A activity or that decreases cancer cell proliferation as determined by a method known to one skilled in the art.

The antibody mimetic, monobody, or polynucleotide may be contained in any appropriate amount in any suitable carrier substance, and is generally present in an amount of 1-95% by weight of the total weight of the composition. The composition may be provided in a dosage form that is suitable for parenteral (e.g., subcutaneously, intravenously, intramuscularly, or intraperitoneally) administration route. The pharmaceutical compositions may be formulated according to conventional pharmaceutical practice (see, e.g., Remington: The Science and Practice of Pharmacy (20th ed.), ed. AR. Gennaro, Lippincott Williams & Wilkins, 2000 and Encyclopedia of Pharmaceutical Technology, eds. J. Swarbrick and J. C. Boylan, 1988-1999, Marcel Dekker, New York).

Pharmaceutical compositions according to the invention may be formulated to release the active agent substantially immediately upon administration or at any predetermined time or time period after administration. The latter types of compositions are generally known as controlled release formulations, which include (i) formulations that create a substantially constant concentration of the drug within the body over an extended period of time; (ii) formulations that after a predetermined lag time create a substantially constant concentration of the drug within the body over an extended period of time; (iii) formulations that sustain action during a predetermined time period by maintaining a relatively, constant, effective level in the body with concomitant minimization of undesirable side effects associated with fluctuations in the plasma level of the active substance (sawtooth kinetic pattern); (iv) formulations that localize action by, e.g., spatial placement of a controlled release composition adjacent to or in contact with a tumor; (v) formulations that allow for convenient dosing, such that doses are administered, for example, once every one or two weeks; and (vi) formulations that target a cancer using carriers or chemical derivatives to deliver the therapeutic agent to a particular cell type (e.g., cancer cell). For some applications, controlled release formulations obviate the need for frequent dosing during the day to sustain the plasma level at a therapeutic level.

Any of a number of strategies can be pursued in order to obtain controlled release in which the rate of release outweighs the rate of metabolism of the agent in question. In one example, controlled release is obtained by appropriate selection of various formulation parameters and ingredients, including, e.g., various types of controlled release compositions and coatings. Thus, the therapeutic is formulated with appropriate excipients into a pharmaceutical composition that, upon administration, releases the therapeutic in a controlled manner. Examples include single or multiple unit tablet or capsule compositions, oil solutions, suspensions, emulsions, microcapsules, microspheres, molecular complexes, nanoparticles, patches, and liposomes.

The pharmaceutical composition may be administered parenterally by injection, infusion or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, supra.

Compositions for parenteral use may be provided in unit dosage forms (e.g., in single-dose ampoules), or in vials containing several doses and in which a suitable preservative may be added (see below). The composition may be in the form of a solution, a suspension, an emulsion, an infusion device, or a delivery device for implantation, or it may be presented as a dry powder to be reconstituted with water or another suitable vehicle before use. Apart from the active agent that reduces or ameliorates a cancer, the composition may include suitable parenterally acceptable carriers and/or excipients. The active therapeutic agent(s) (e.g., an antibody mimic, monobody, or polynucleotide described herein) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing agents.

In some embodiments, the composition comprising the active therapeutic (i.e., a monobody, antibody mimetic, or polynucleotide herein) is formulated for intravenous delivery. As indicated above, the pharmaceutical compositions according to the invention may be in the form suitable for sterile injection. To prepare such a composition, the suitable therapeutic(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). In cases where one of the agents is only sparingly or slightly soluble in water, a dissolution enhancing or solubilizing agent can be added, or the solvent may include 10-60% w/w of propylene glycol or the like.

Combination Therapies

Optionally, an anti-cancer therapeutic of the invention (e.g., an antibody mimetic, monobody, or polynucleotide described herein) may be administered in combination with any other standard anti-cancer therapy; such methods are known to the skilled artisan and described in Remington's Pharmaceutical Sciences by E. W. Martin.

Screening Assays Using Monobodies

Antibody mimetics or monobodies of the present invention are useful tools for investigating kinase activation mechanisms (particularly, activation of Aurora A kinase) in vitro and in vivo. Accordingly, the invention provides a method of modulating activity of an Aurora A kinase, the method comprising contacting the Aurora A kinase with an antibody mimetic or monobody of the invention. In some embodiments, the antibody mimetic or monobody contacts Aurora A kinase in vitro. In other embodiments, the antibody mimetic or monobody contacts Aurora A kinase in a cell. It is expected that use of a monobody to disrupt an extensive protein-protein interaction area will be useful for advancing research and investigation of mechanisms of kinase (particularly, Aurora A kinase) regulation and activities in cancer. The dual effect of disruption of allosteric activation and localization, and the specific effect of the monobodies on Aurora A's function in the spindles while keeping its function in the centrosome intact offers a unique intrinsic control of Aurora A's activities that may be useful in certain experiments, particularly live-cell imaging experiments using the monobodies. To facilitate detection of the antibody mimetics or monobodies of the invention (particularly in live-cell imaging experiments), fusion polypeptides comprising an antibody mimetic or monobody fused to a detectable tag are provided herein.

Kits

The invention provides kits for the treatment or prevention of cancer, particularly cancers associated with overexpression of Aurora A kinase. In one embodiment, the kit includes a therapeutic or prophylactic composition containing an effective amount of an antibody mimetic, monobody, or fragment thereof (or a polynucleotide encoding such) in unit dosage form. In some embodiments, the kit comprises a sterile container which contains a therapeutic or prophylactic composition; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

If desired a composition comprising a therapeutic agent (e.g., antibody mimetic, monobody, or polynucleotide) of the invention is provided together with instructions for administering the agent to a subject having or at risk of developing cancer. The instructions will generally include information about the use of the composition for the treatment or prevention of cancer. In other embodiments, the instructions include at least one of the following: description of the therapeutic agent; dosage schedule and administration for treatment or prevention of ischemia or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Figure 1B:
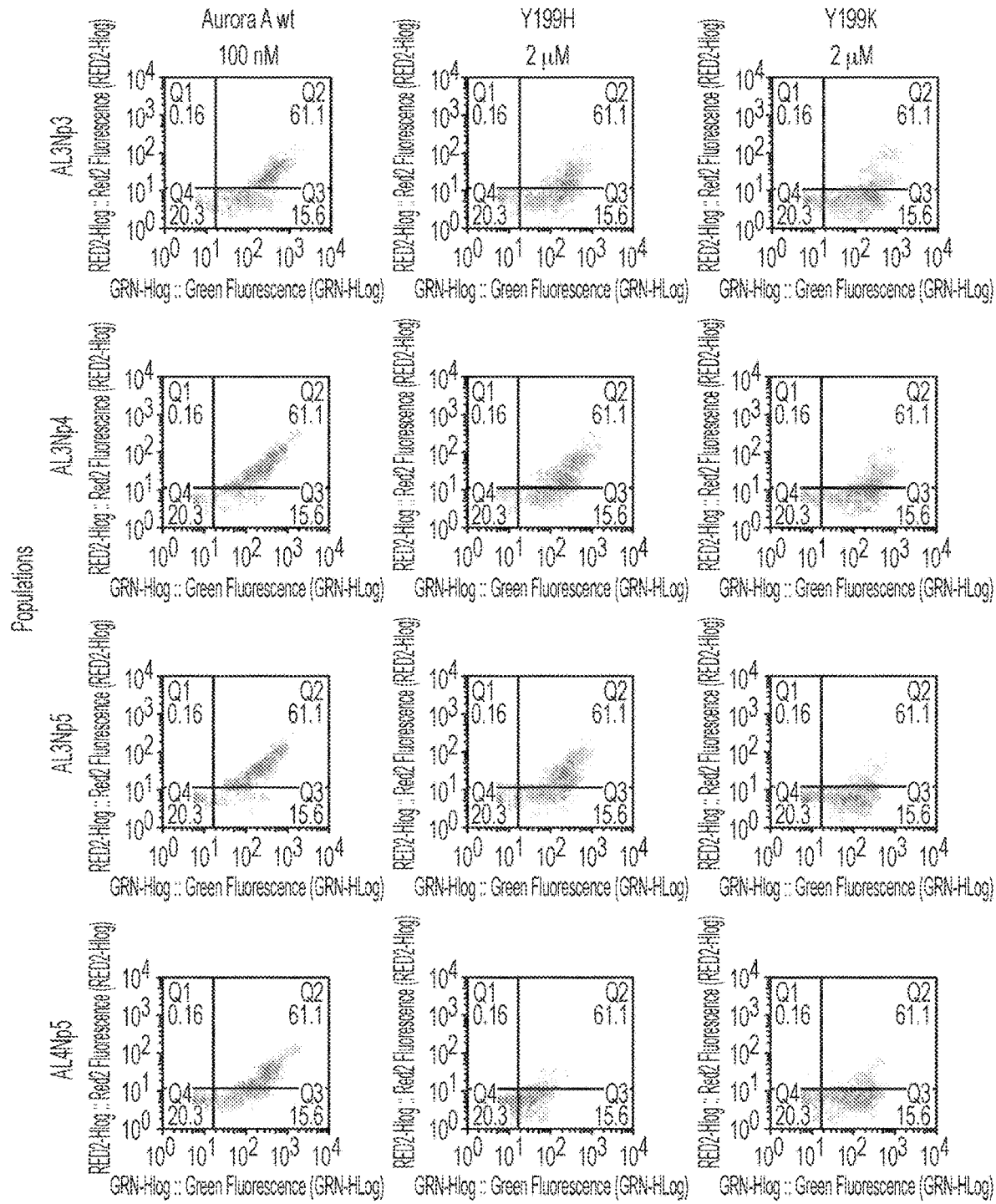
Figure 1B:
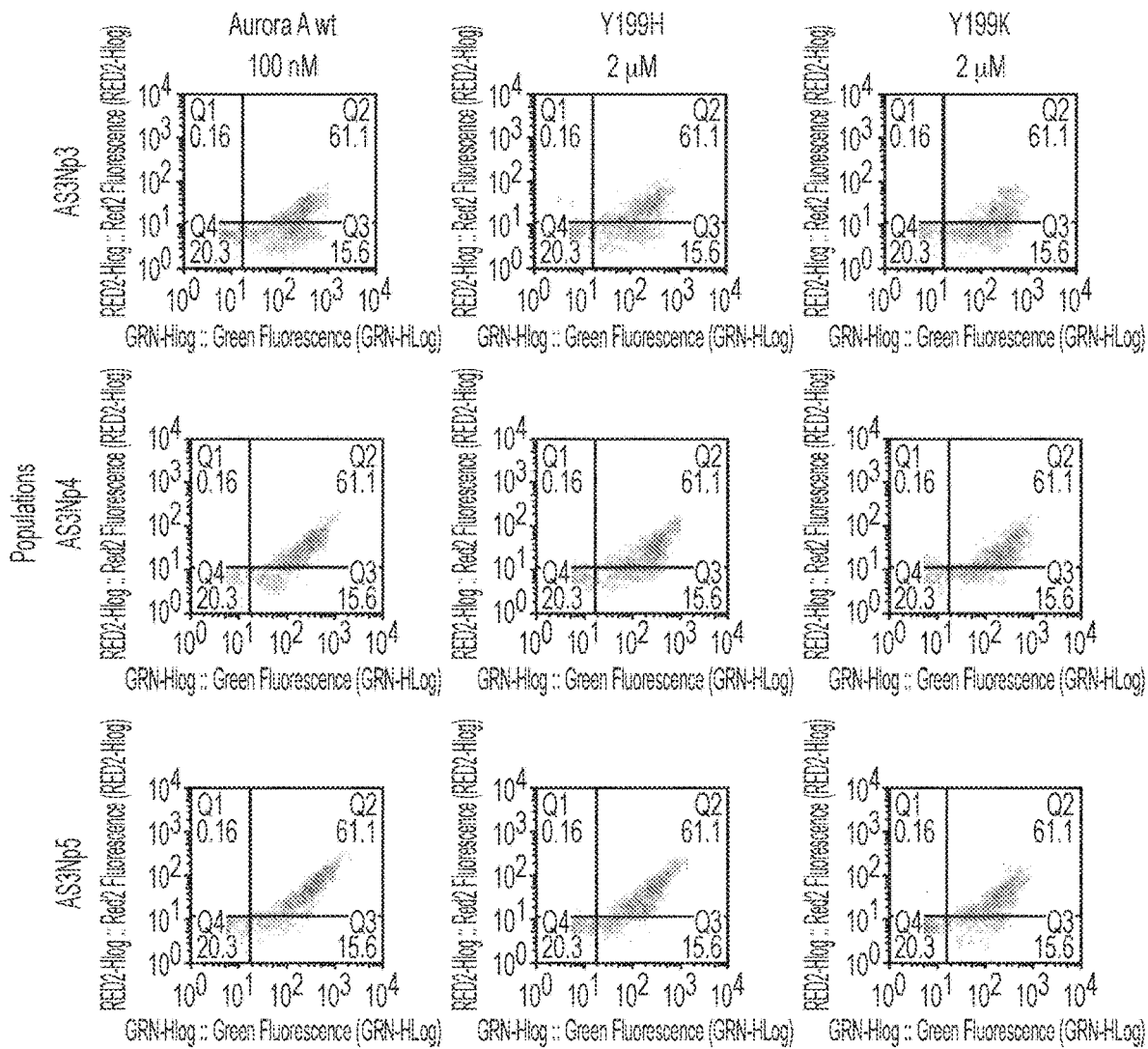
Figure 1C:
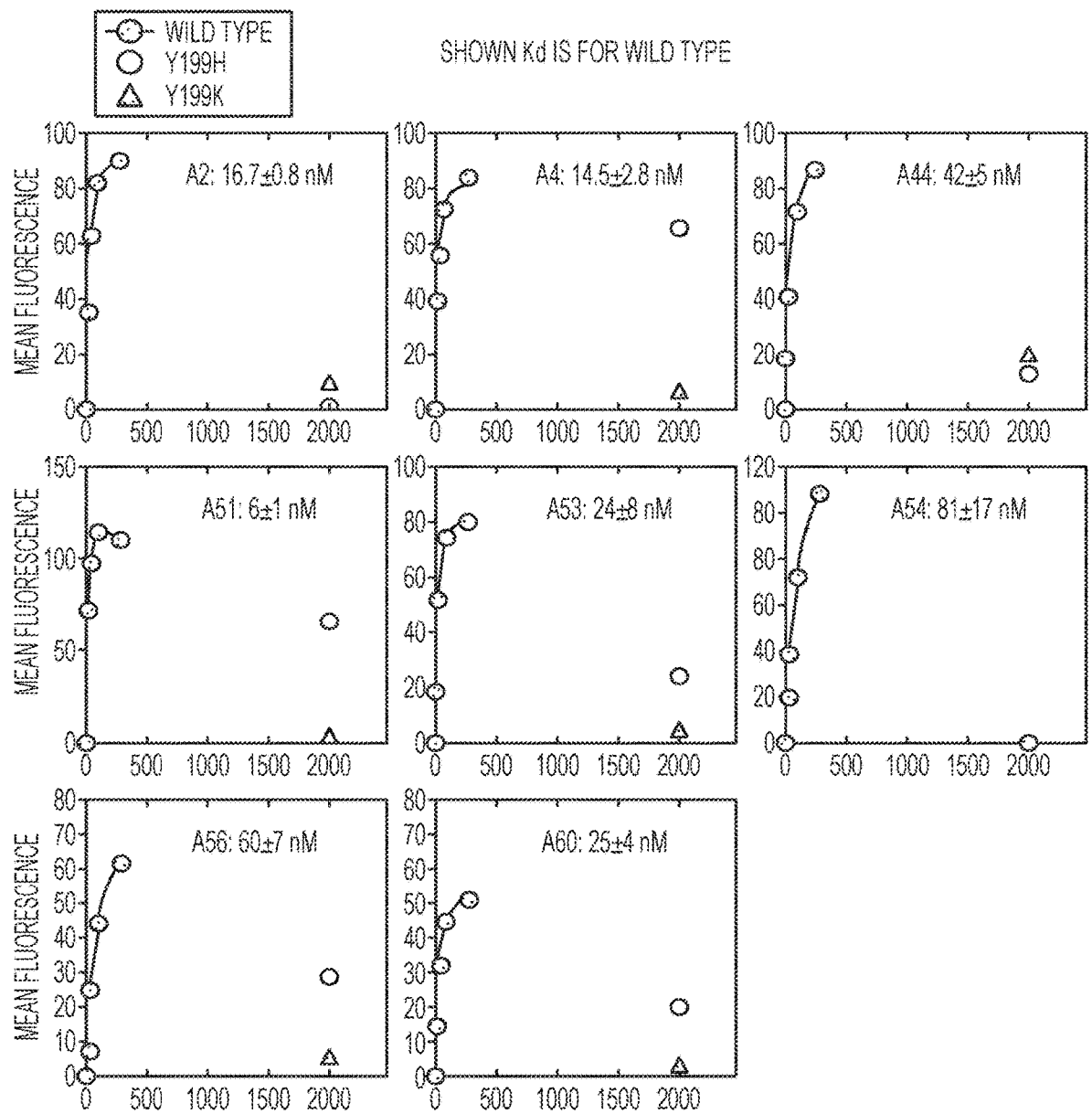

Example 1: Generation of Monobodies Specifically Binding to the PIF Pocket of Aurora A Kinase A high-throughput yeast-display library screening of more than a million monobody clones to identify activating and inhibitory monobodies towards Aurora A kinase was performed. Using phage display and Aurora A constructs, monobody libraries were screened for monobodies that bound tightly to the PIF pocket of human Aurora A kinase (FIGS. 1A-1B). The selection scheme relied on (1) a round of positive selection that selected for monobodies binding more strongly to Aurora A than Aurora A-TPX2 chimera (FIG. 1A) and (2) further refinement of selection by using Y199H and Y199K Aurora A hotspot mutants in negative selection rounds of current monobody pools (FIG. 1B). From the screen, a number of monobodies specifically binding to and having a high affinity for the PIF pocket of AuroraA were identified (FIG. 1C). These monobodies were selected for further biochemical characterization.

Example 2: Biochemical Characterization of Monobodies Specifically Binding to the PIF Pocket of Aurora A Kinase Monobodies Mb2, Mb44, Mb51, Mb56, Mb54, and Mb60 were selected for further biochemical characterization of the Aurora A-monobody interaction. Specifically, the affinity to Aurora A kinase and the ability of these monobodies to activate or inhibit the kinase activity of Aurora A kinase were measured.

Isothermal titration calorimetry (ITC) experiments using the monobodies were performed to determine the thermodynamics of the Aurora A-monobody interaction.

Results showed that the monobodies bound to Aurora A kinase with affinities ranging in the nanomolar (nM) to low micromolar (μM) range (FIGS. 2A-2F). The monobodies bound to Aurora A with higher affinity than TPX2's affinity to Aurora A (affinity of TPX2 for AuroraA was measured to be 5 μM).

Figure 3:
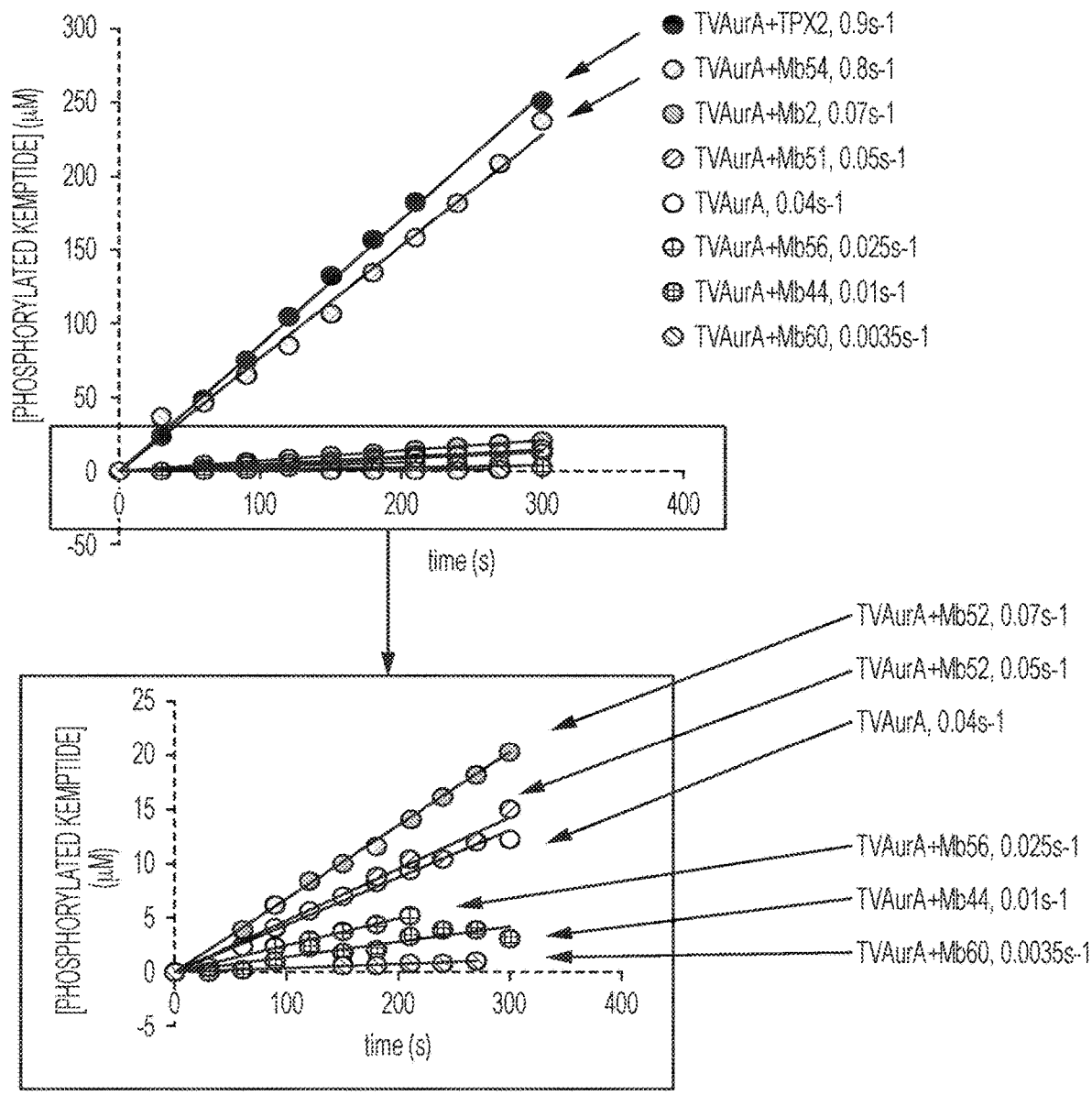
FIG. 3 is a set of plots showing that monobodies in the study described herein (Mb2, Mb44, Mb51, Mb56, Mb54, and Mb60) can activate or inhibit Aurora A kinase activity. The top plot shows measurements of phosphorylation of kemptide (a peptide substrate for Aurora A kinase) when incubated with Aurora A kinase and TPX2, Mb2, Mb44, Mb51, Mb56, Mb54, and Mb60. The bottom plot shows a portion of the top plot, with the vertical axis re-scaled. The measurements indicate that the monobodies Mb2, Mb44, Mb51, Mb56, Mb54, and Mb60 modulate Aurora A kinase activity by activating or inhibiting Aurora A kinase activity, with various degrees of activation or inhibition.

Next, a quantitative High Performance Liquid Chromatography (HPLC)-based assay was established and used to determine the kinetics of Aurora A activation by the monobodies. Assay results showed that the monobodies had a differential effect on the kinase activity of Aurora A (FIG. 3). As shown in FIG. 3, at least one monobody (Mb54) showed activation of kinase activity of Aurora A Several showed strong inhibition of Aurora A's kinase activity (e.g., Mb60).

Figure 4A:
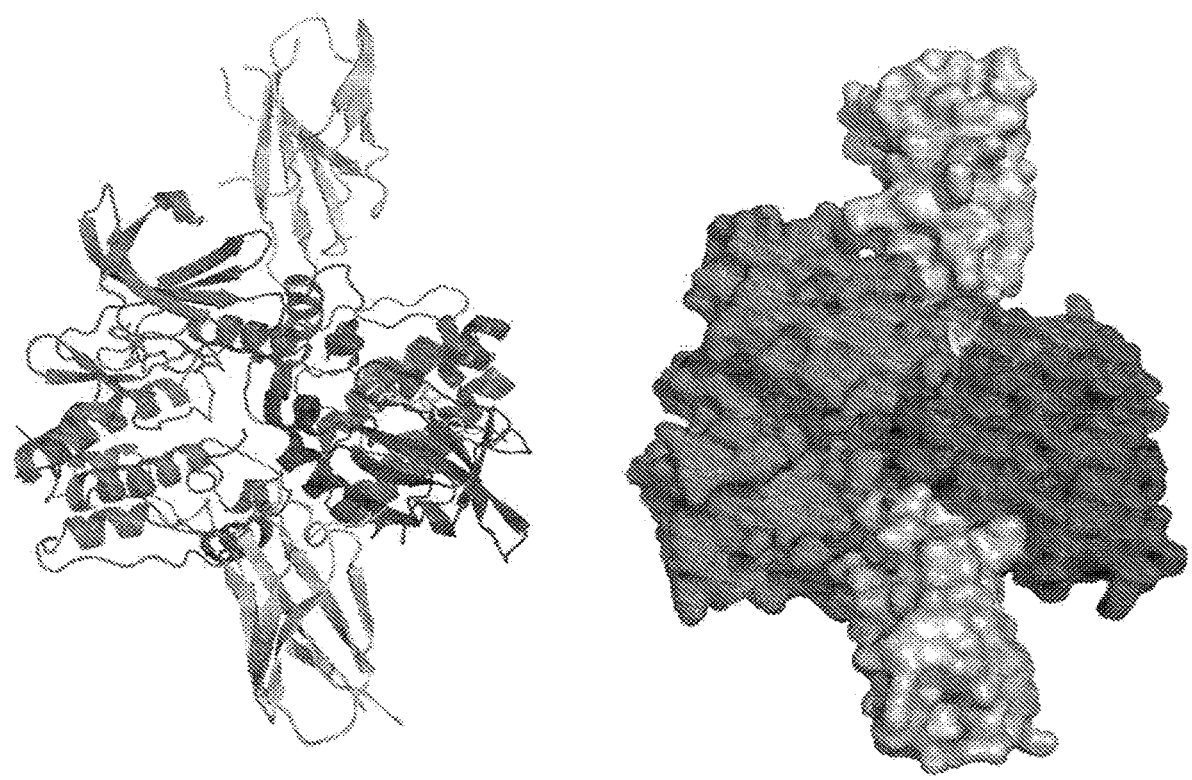
FIGS. 4A-4E are images depicting the structural mechanism of inhibition or activation of Aurora A kinase by monobodies in the study described herein.
Figure 4B:
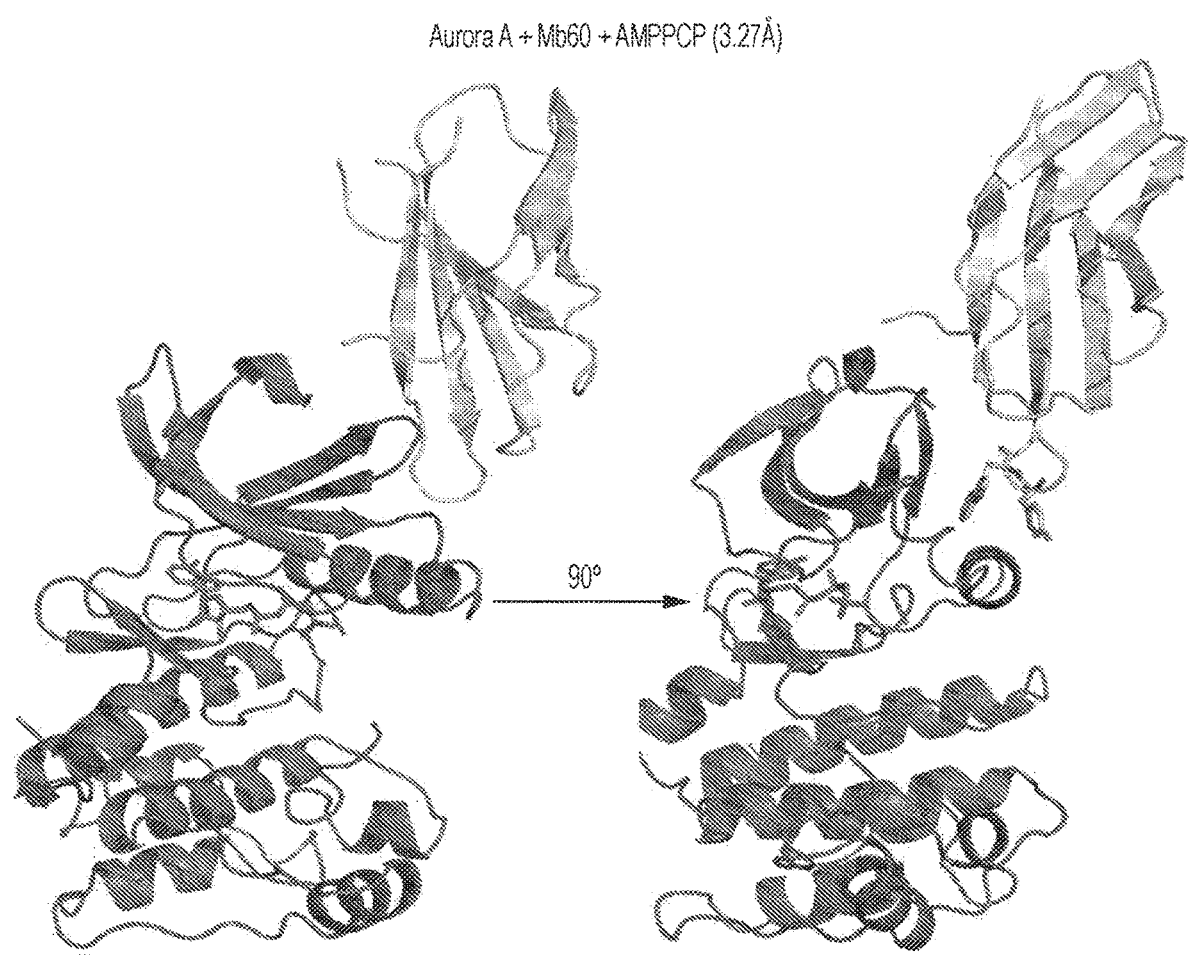
Figure 4C:
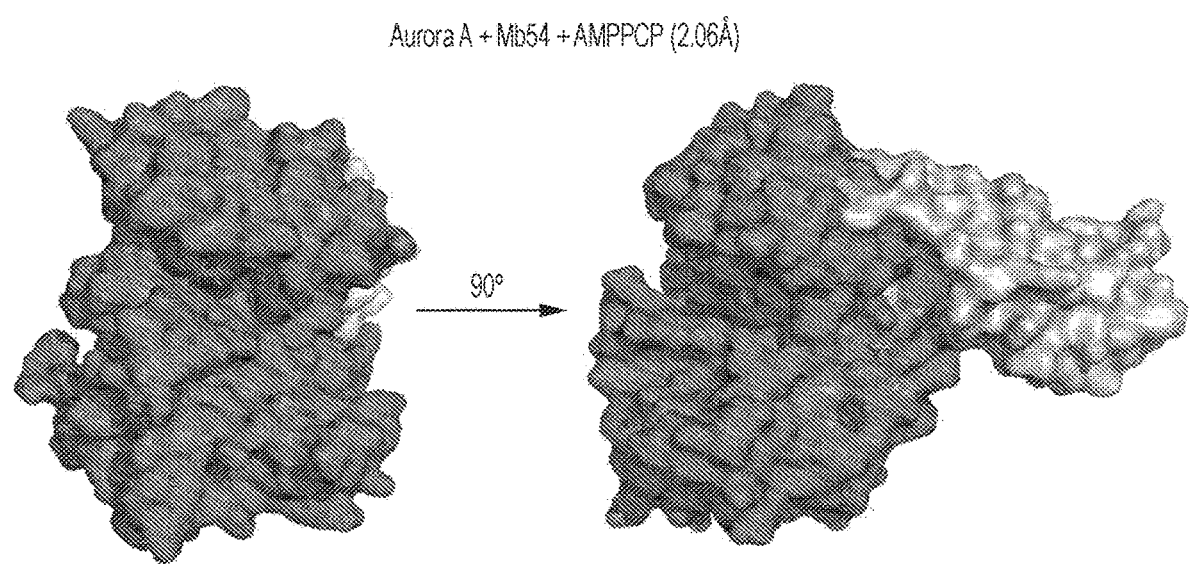
Figure 4D:
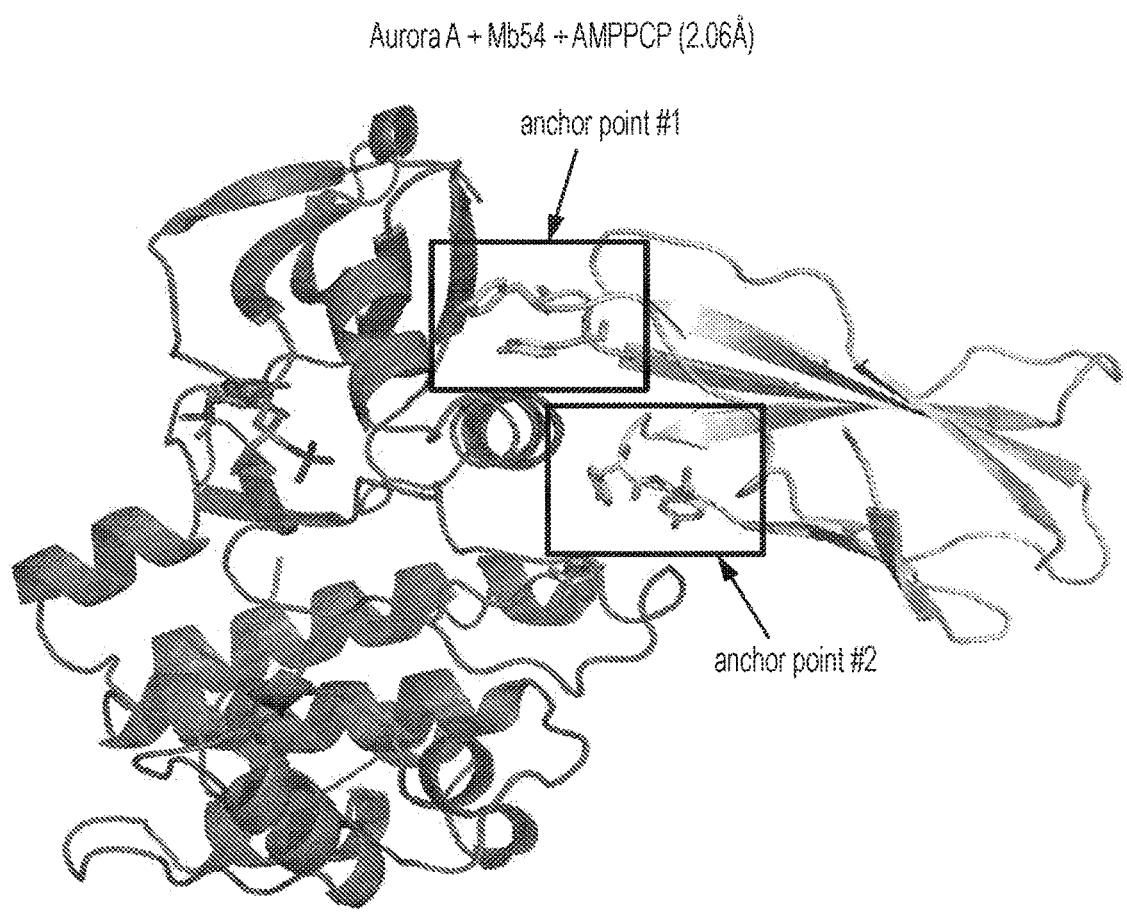
Figure 4E:
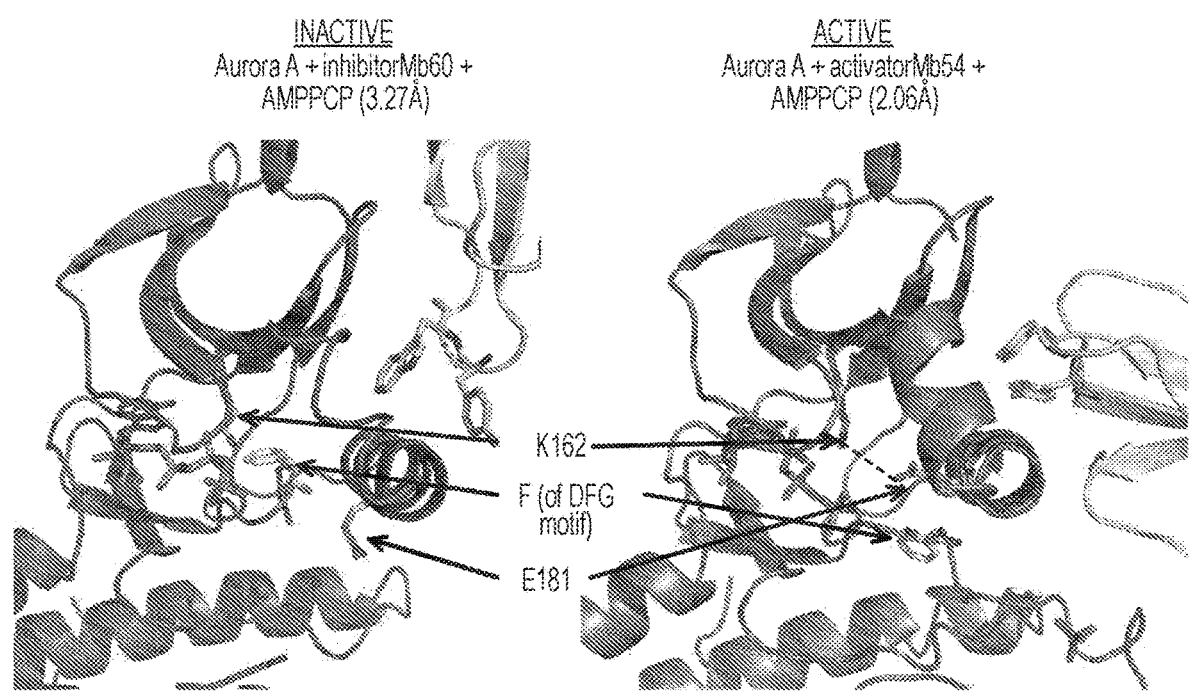

Example 3: High-Resolution X-Ray Crystallography Structures of Aurora A in the Presence of Activating and Inhibitory Monobodies Bound to the PIF Pocket and ATP-Competitive Drug Bound to the ATP Pocket High-resolution X-ray crystallography structures of Aurora A in the presence of an activating (Mb54) bound to the PIF pocket, an inhibitory monobody (Mb60) bound to the PIF pocket, and ATP-competitive drugs bound to the ATP-binding pocket were solved. The high-resolution x-ray structures of complexes with activating and inhibiting monobodies with Aurora A revealed the mechanism of activation and inhibition of the kinase activity of Aurora A FIGS. 4A-4E depict the mechanism of inhibition of Aurora A's kinase activity by inhibitory monobody Mb60 and activation of Aurora A's kinase activity by activating monobody Mb54. The inhibitory WY-motif on Mb60 "locks" the aC-helix of Aurora A in an inactive conformation (FIGS. 4A-4B). The activator Mb54 activates Aurora A kinase activity via anchor points that "push" on the aC-helix of Aurora A (FIG. 4C). The activating anchor points of Mb54 (FIG. 4D) push on the aC-helix and coordinate AuroraA's activation loop to keep the kinase in an active conformation. The monobodies shift equilibria between active and inactive Aurora A kinase (FIG. 4E).

Example 4: Intracellular Delivery of Inhibitory Monobodies by Cationic Liposome Mediated Delivery of Monobodies Fused to Supercharged Green Fluorescent Protein (GFP)

Figure 5:
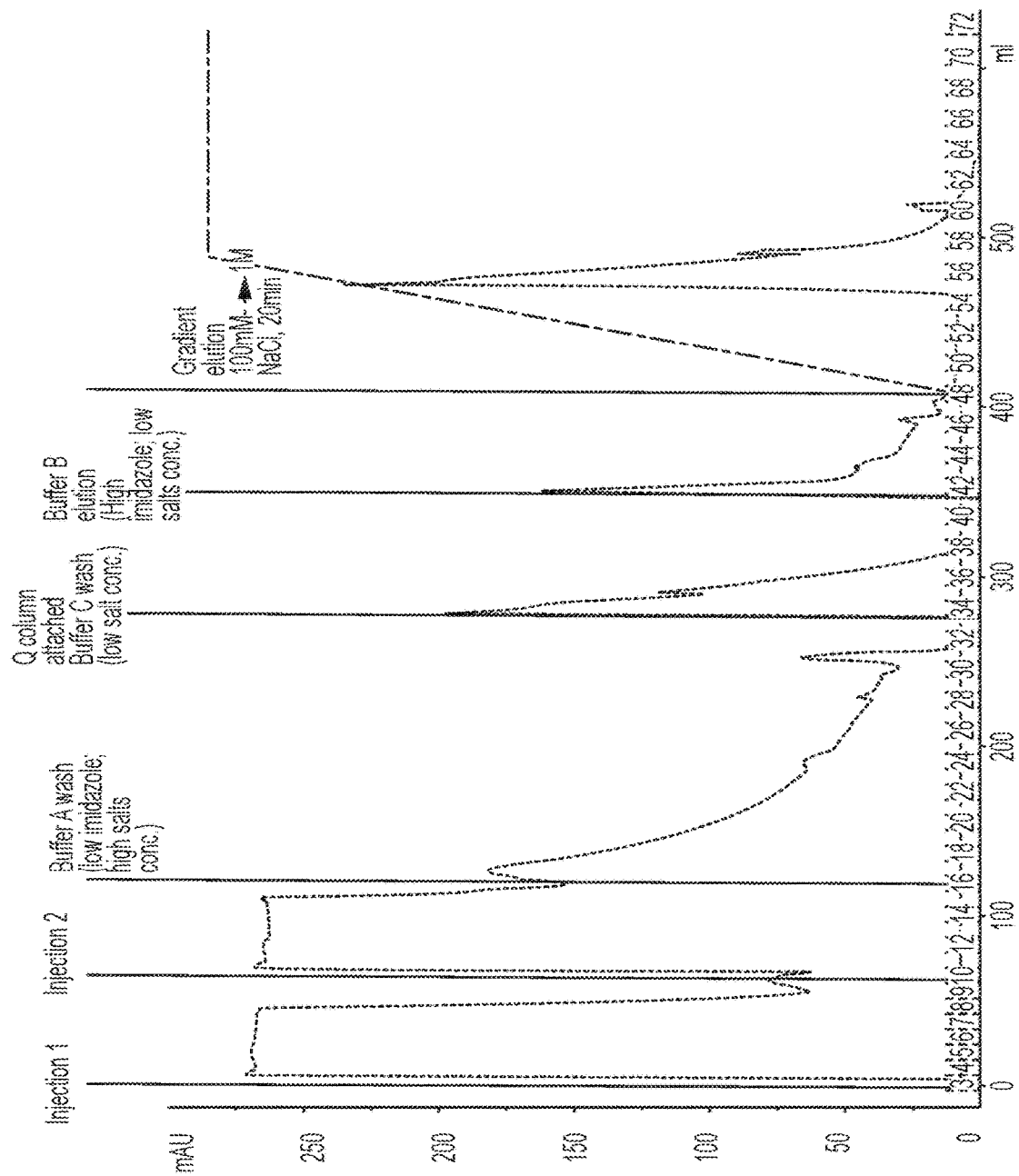
FIG. 5 shows purification of monobody Mb60 fused to supercharged GFP by gradient elution chromatography.
Figure 5:
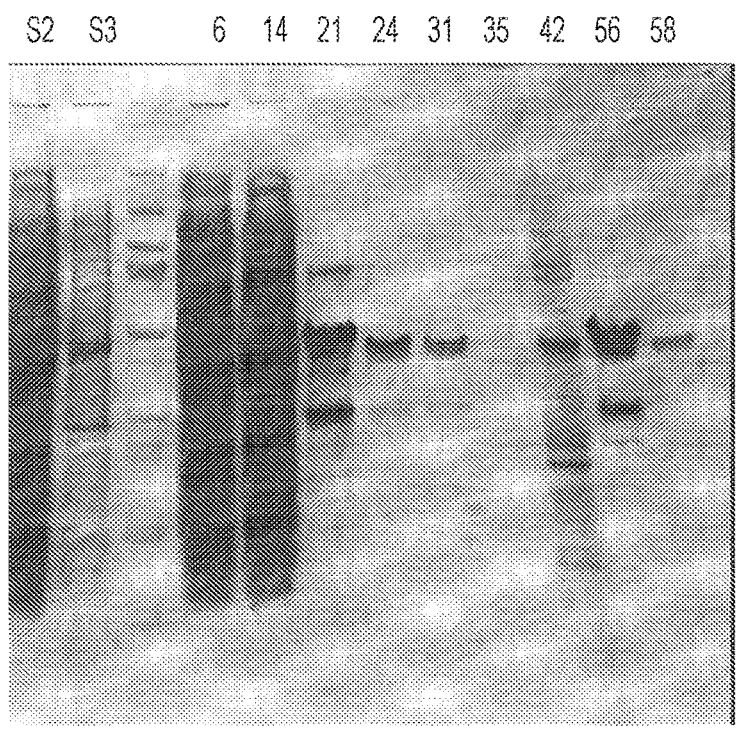
Figure 6A:
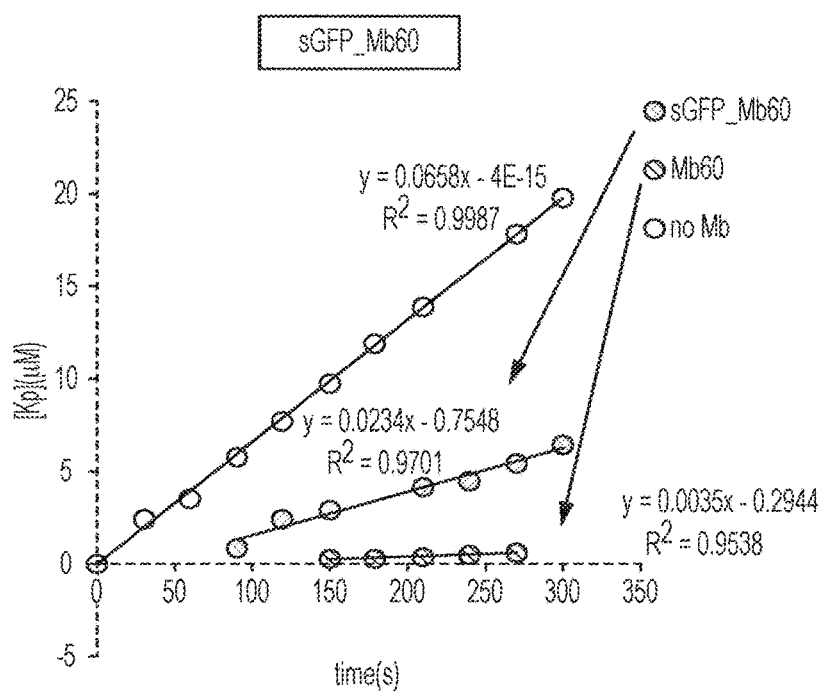
FIGS. 6A-6C are plots showing characterization of binding to Aurora A kinase and effect on Aurora A kinase activity of monobody Mb60 and monobody Mb60 fused to supercharged GFP (sGFP-Mb60).
Figure 6B:
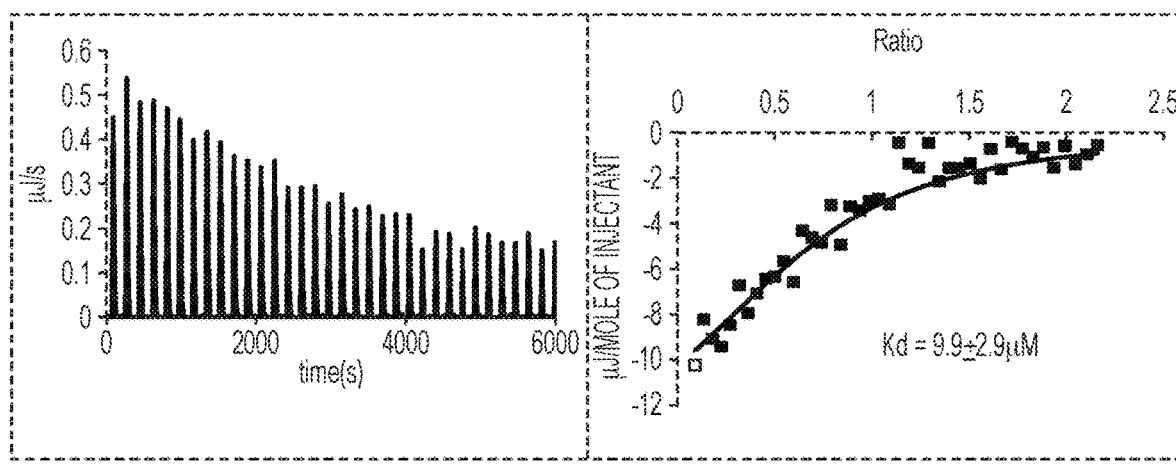
Figure 6C:
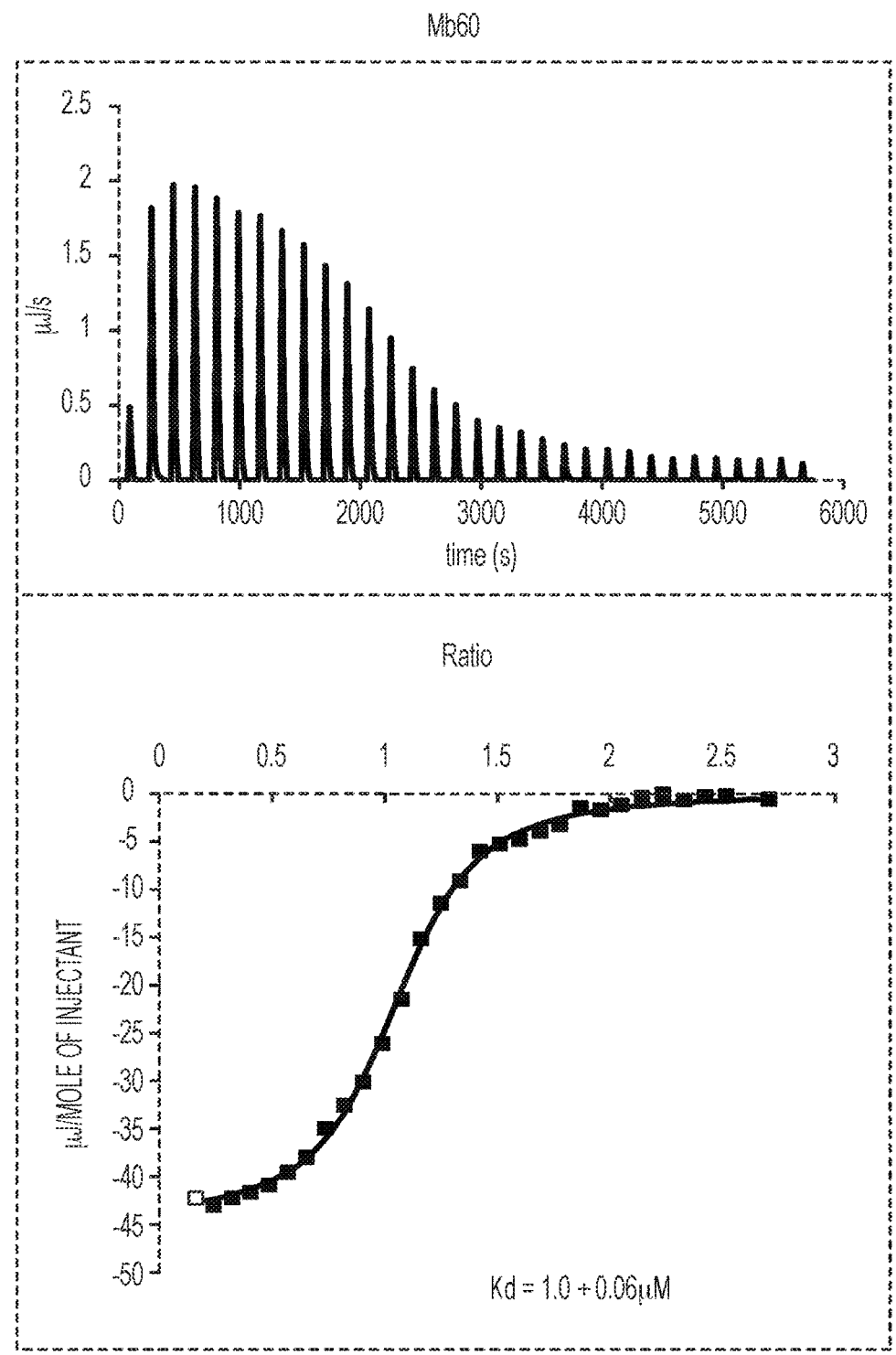

The Aurora A-monobody interaction was further characterized in mammalian cells. To perform this characterization, monobodies were fused to a supercharged green fluorescentprotein (GFP) and the monobody-supercharged GFP fusion polypeptides were delivered to HEK293 and HeLa cells using cationic liposomes according to the method described in Zuris et al. Nat. Biotechnol. (2015) 3373-80. Monobody Mb60 was fused to supercharged GFP and purified (FIG. 5). Next, biochemical characterization of the Mb60-supercharged GFP fusion ("sGFP-Mb60") was performed. FIGS. 6A-6C show the affinity and the effect on Aurora A's kinase activity of sGFP-Mb60 compared to Mb60. As shown in FIG. 6A, sGFP-Mb60 inhibited kinase activity of Aurora A Mb60 showed stronger inhibition of kinase activity than sGFP-Mb60. FIGS. 6B-6C show the thermodynamics of binding of sGFP-Mb60 and Mb60 to Aurora A kinase. As indicated by the dissociation constant values (Kt) in the plots in FIGS. 6B-6C, Mb60 bound to Aurora A kinase with about 1.0 µM affinity (FIG. 6C), whereas sGFP-Mb60 bound Aurora A kinase at a lower affinity of about 9.9 µM (FIG. 6B).

Figure 7A:
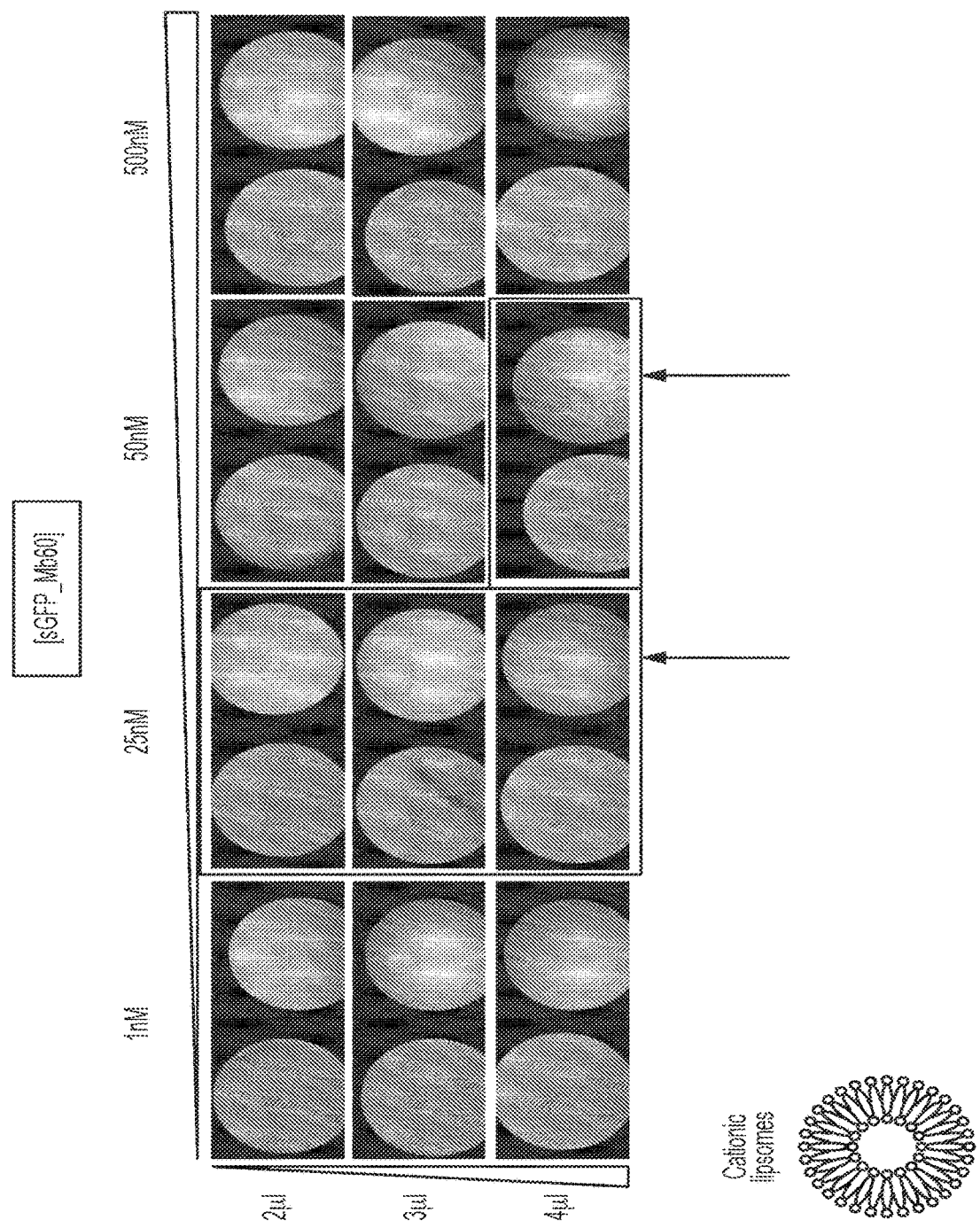
FIGS. 7A-7C are micrographs showing live cell images during optimization of delivery of monobody Mb60 fused to supercharged GFP (sGFP-Mb60) into cells using cationic liposomes.
Figure 7B:
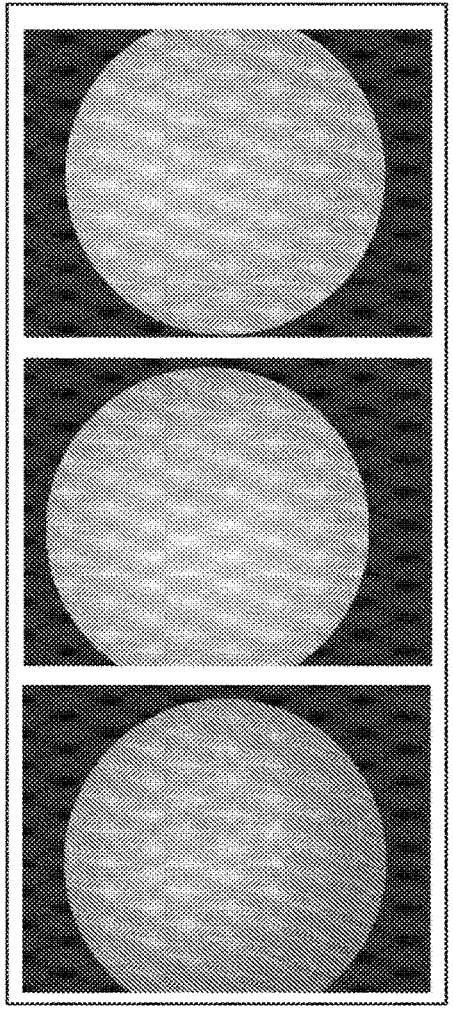
Figure 7B:
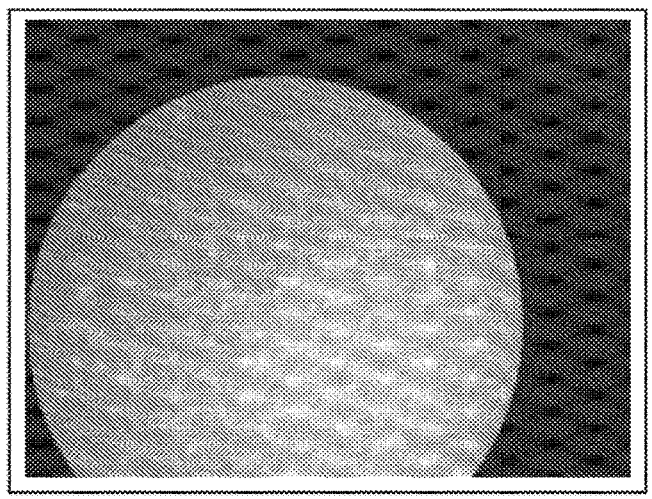
Figure 7C:
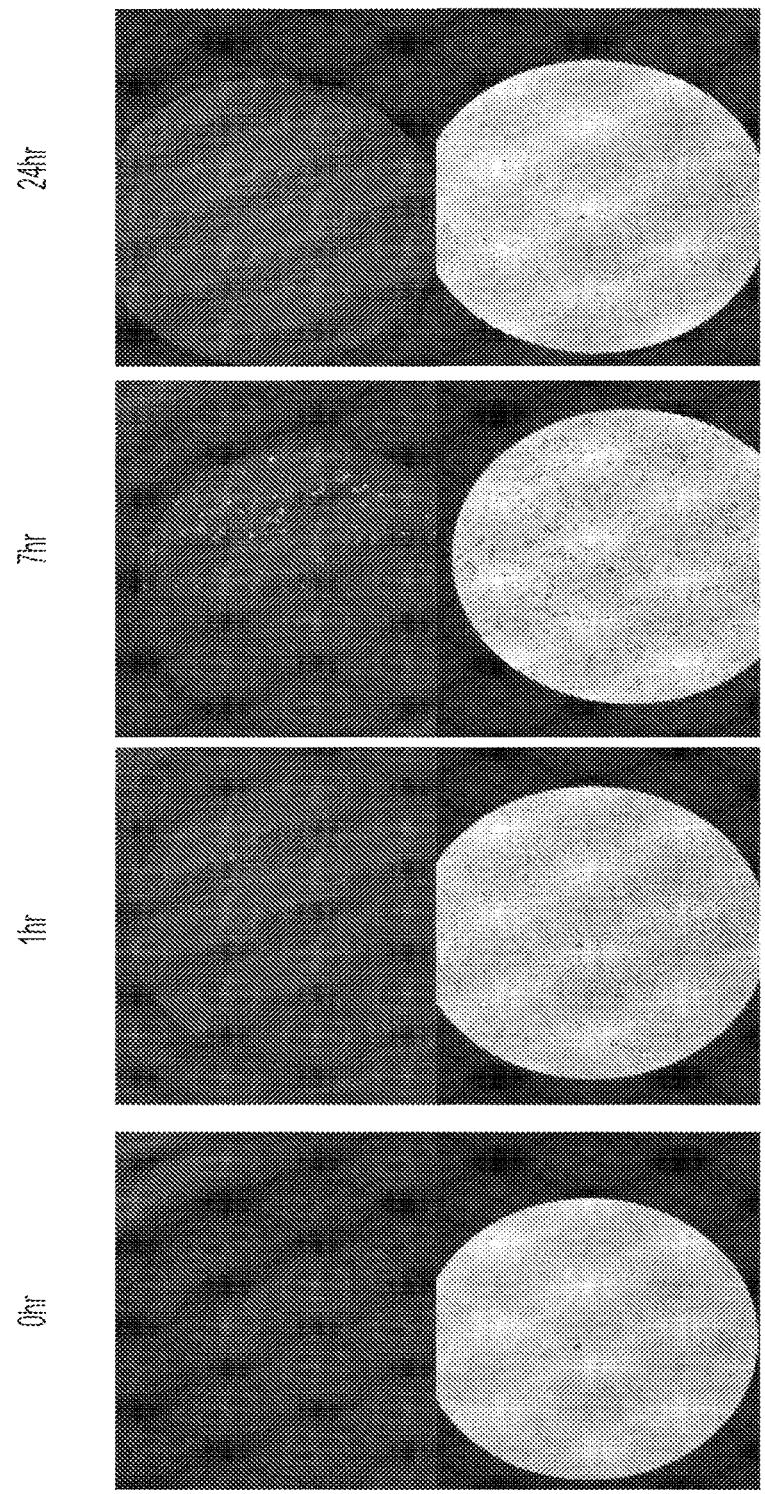

Efficiency of delivery of sGFP-Mb60 into mammalian cells (HEK and HeLa cells) was then optimized. To optimize delivery, various concentrations (1 nM, 25 nM, 50 nM, and 500 nM) of sGFP-Mb60 were incubated with various amounts of cationic liposomes (2 µl, 3 µl, and 4 µl), and delivery of sGFP-Mb60 into cells was assayed by live cell imaging (FIG. 7A). Optimal delivery was achieved at a combination of 50 nM sGFP_Mb60 and 4 µl cationic liposomes (FIG. 7B). FIG. 7C shows delivery of sGFP-Mb60 to cells monitored at various time points (0 hr, 1 hr, 7 hr, and 24 hr).

Example 5: Co-Localization of Inhibitory Monobody with Aurora A Kinase During Various Cell Cycle Stages and Mediation of Cell Death Activity of the monobody Mb60 fused to supercharged GFP ("sGFP-Mb60") in vivo was assayed by fluorescence microscopy. Aurora A kinase is implicated in regulation of mitotic progression, particularly spindle assembly and maintenance of the mitotic spindle. During the transition to mitosis, Aurora A kinase is known to localize to the centrosomes and the spindle, with levels and activity of Aurora A kinase peaking during this point.

Figure 8A:
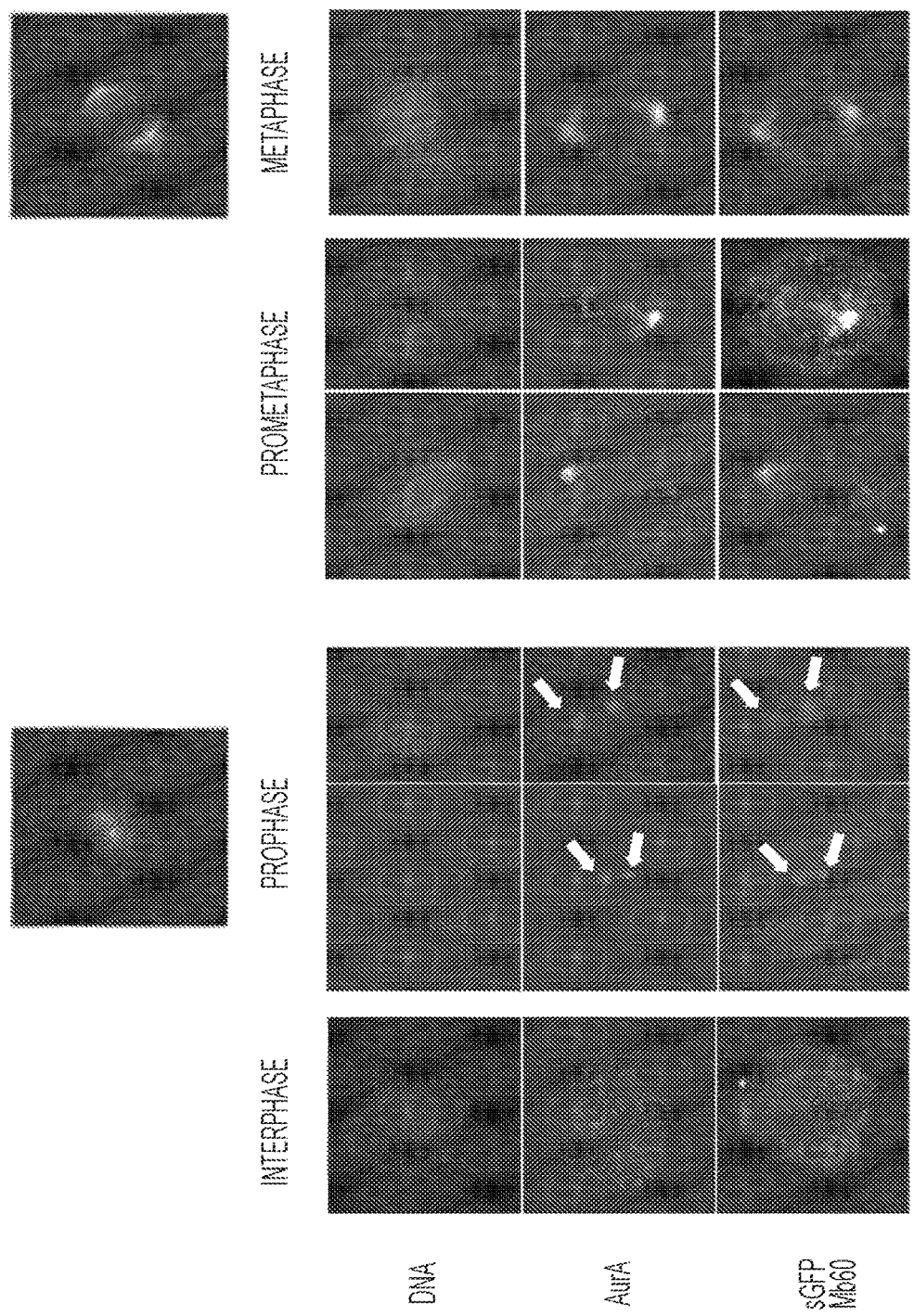
FIGS. 8A-8H are a series of micrographs showing intracellular locations of Aurora A kinase and monobody Mb60 fused to supercharged GFP (sGFP-Mb60) during various stages of the cell cycle. FIG. SA shows high magnification views of DNA, Aurora A kinase ("AurA"), and sGFP-Mb60 ("sGFP_Mb60") during interphase, prophase, prometaphase, and metaphase. The micrographs at the top of FIG. SA show visualization of Aurora A kinase in a cell during prophase (left) and metaphase (right) in a study described in Bischoff et al. (1998) EMBO J., 1; 17(11):3052-65. FIG. SA shows co-localization of sGFP-Mb60 with Aurora A kinase during prophase, prometaphase, and metaphase.
Figure 8B:
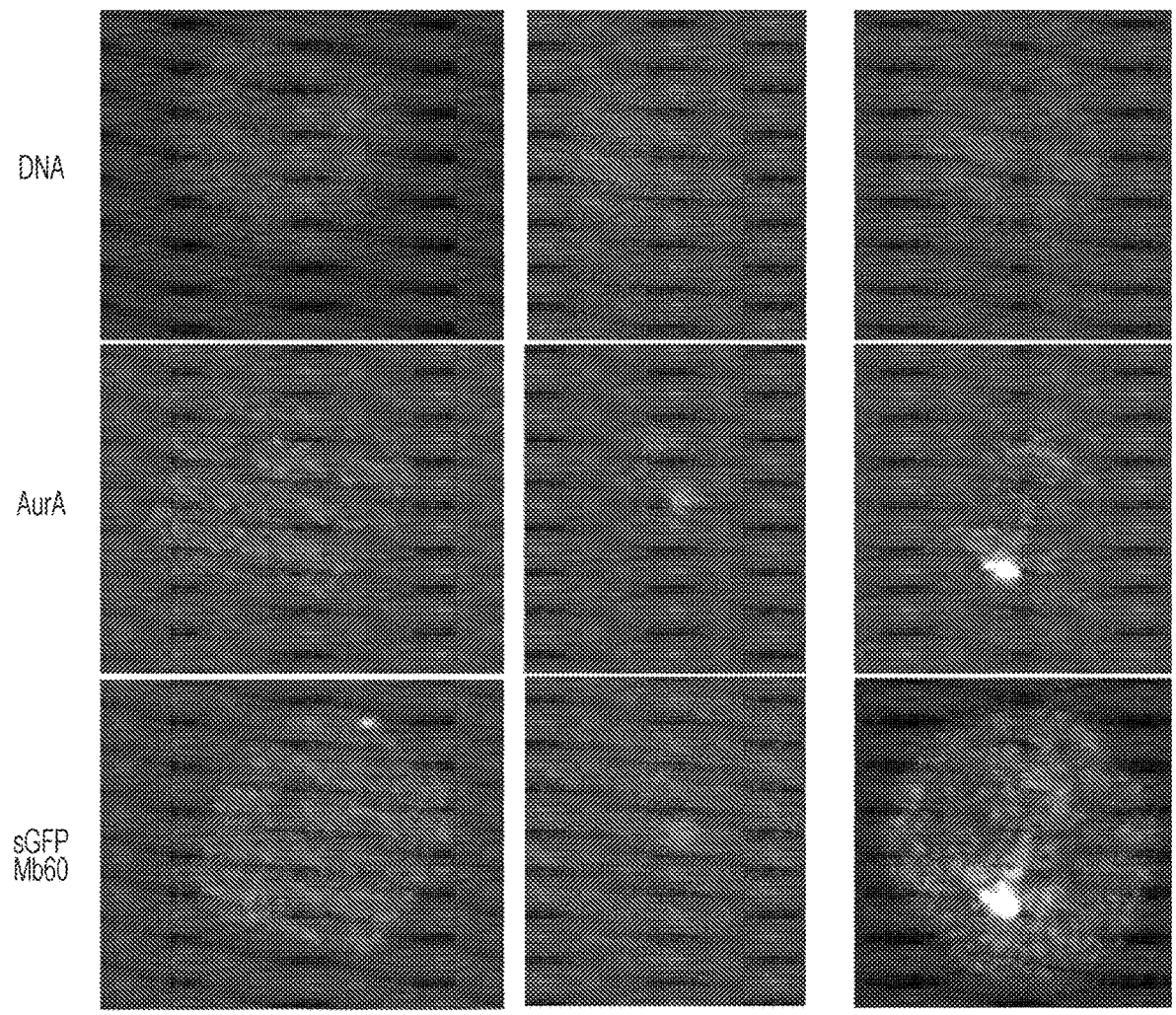
Figure 8C:
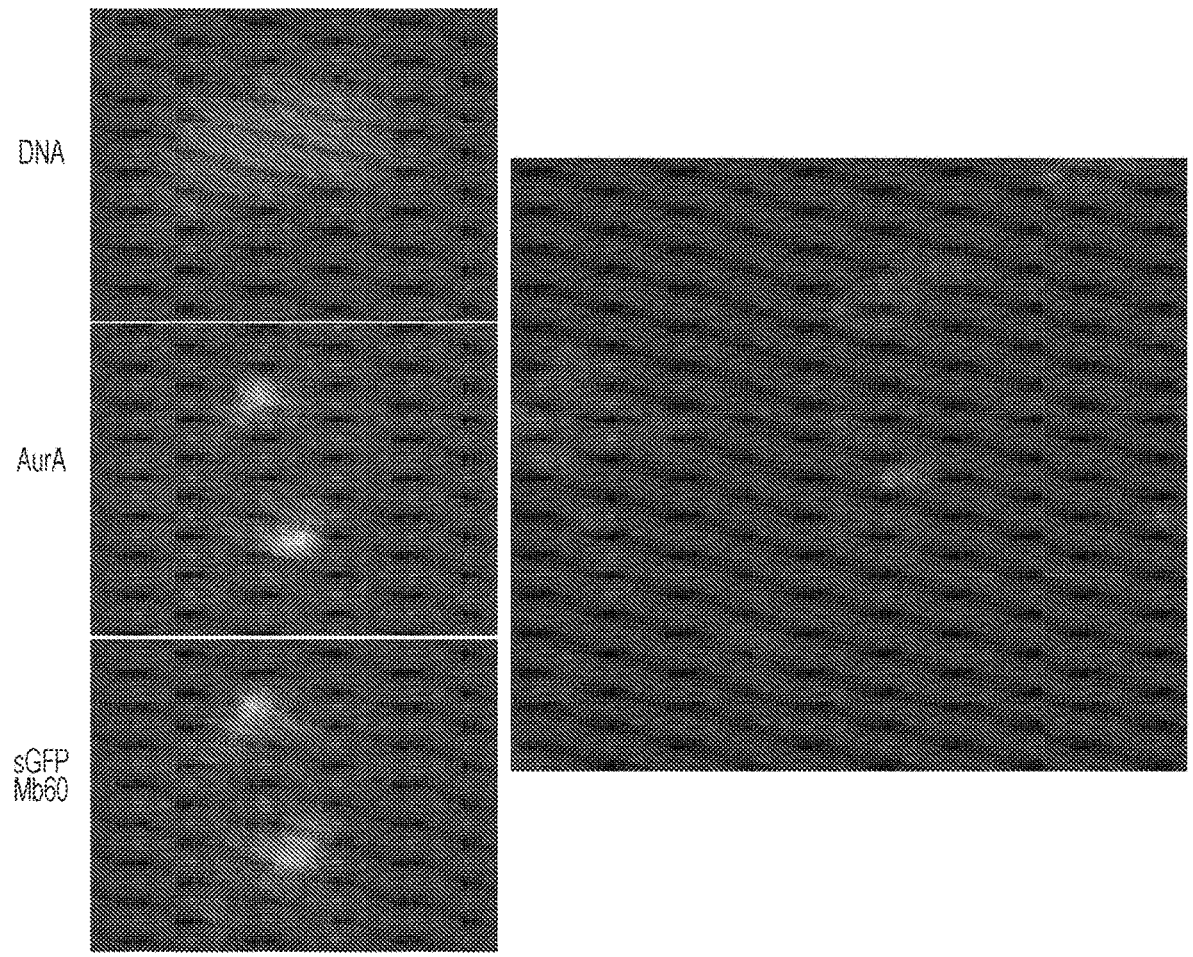
Figure 8D:
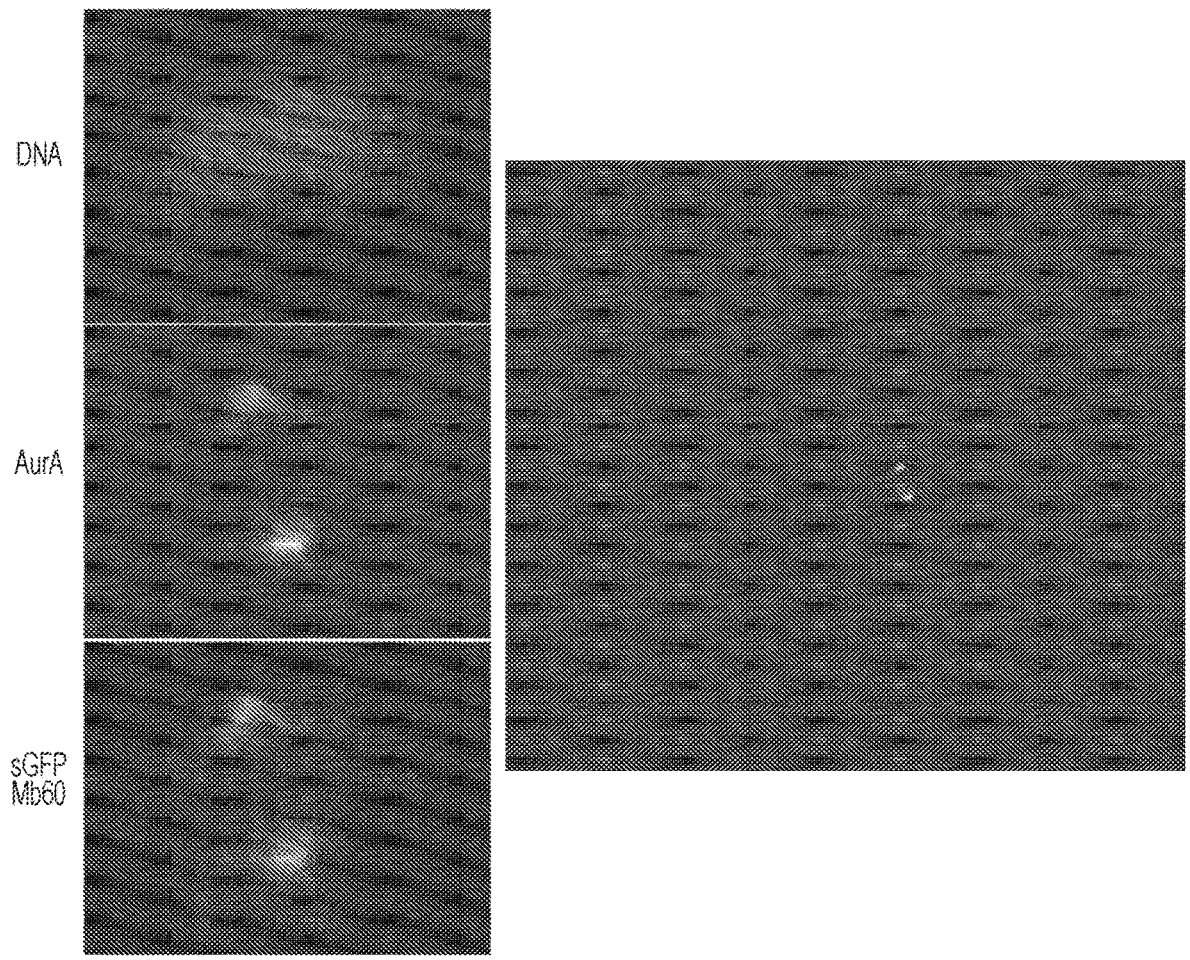
Figure 8E:
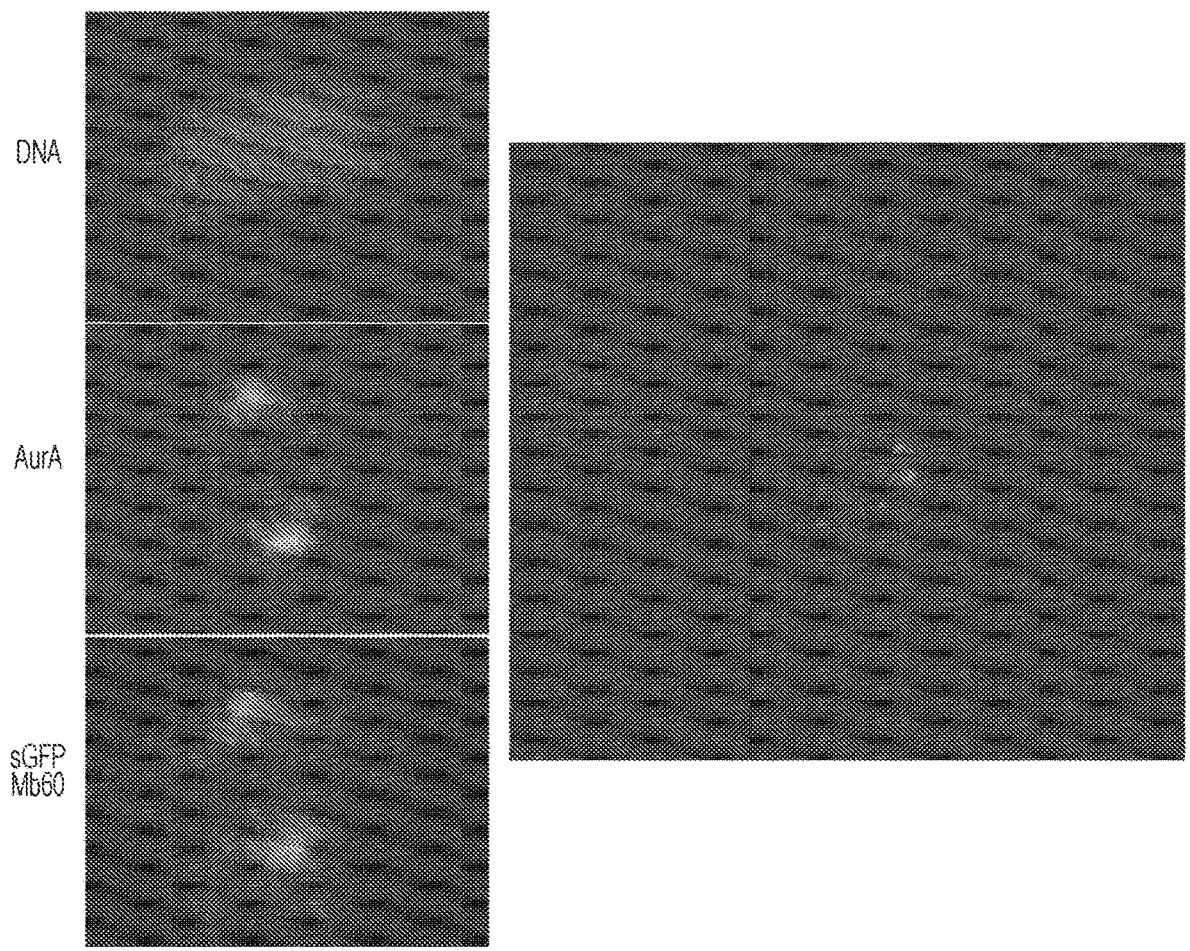
Figure 8F:
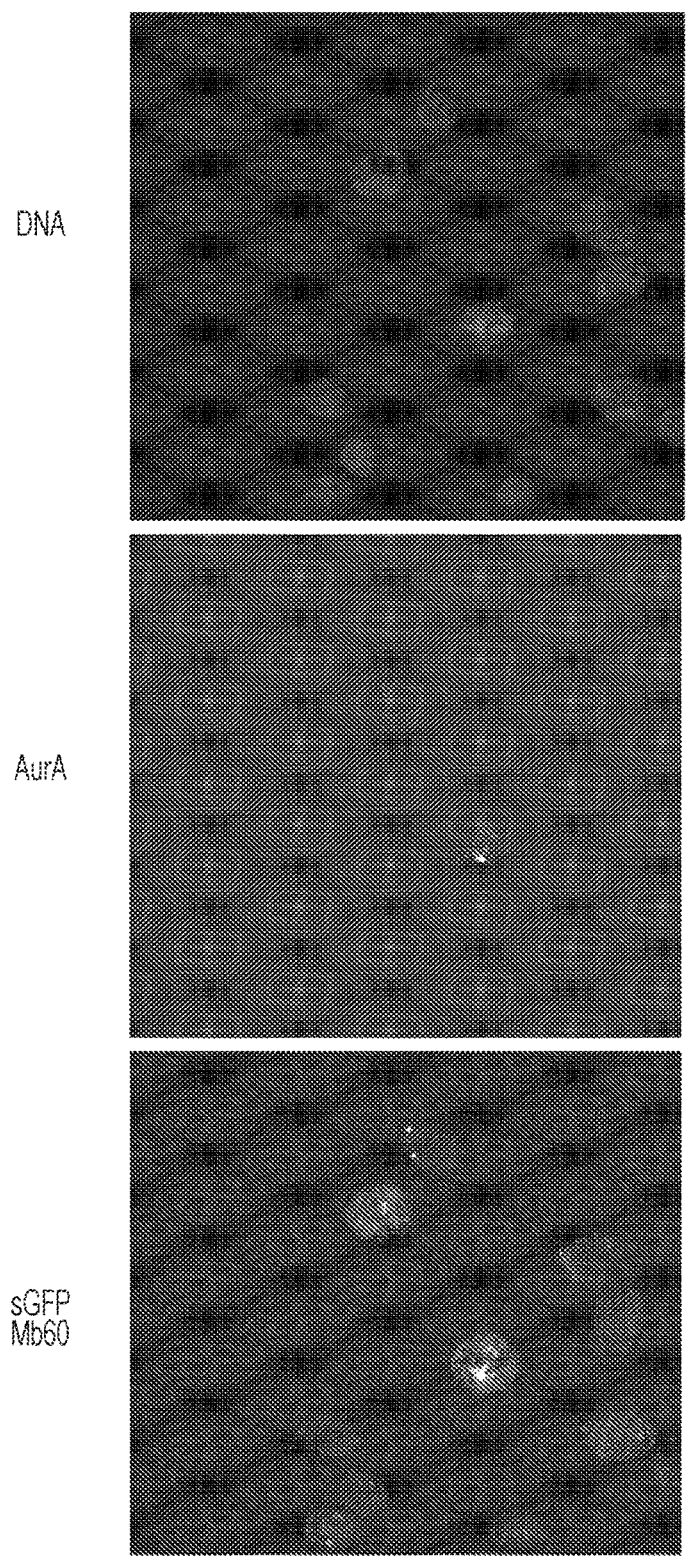
Figure 8G:
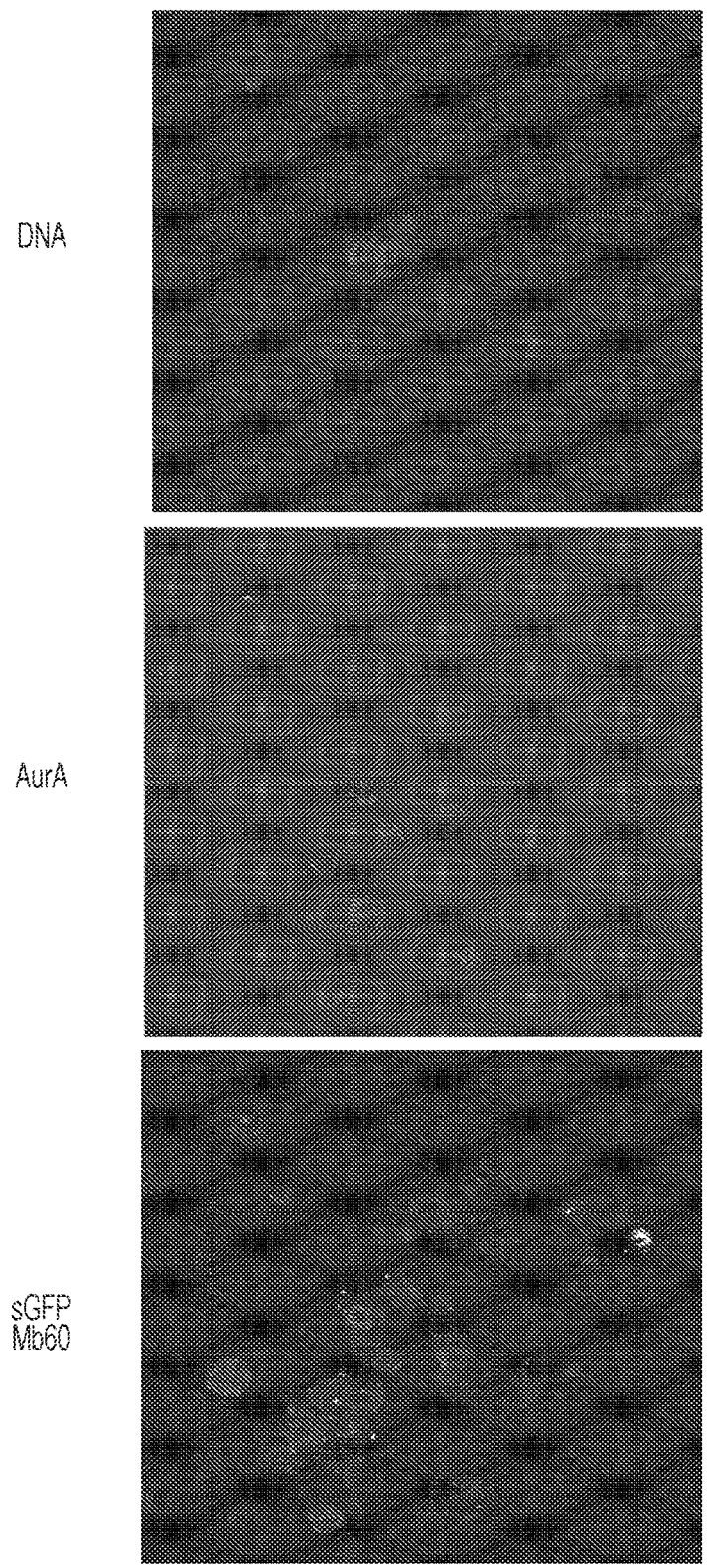
Figure 8H:
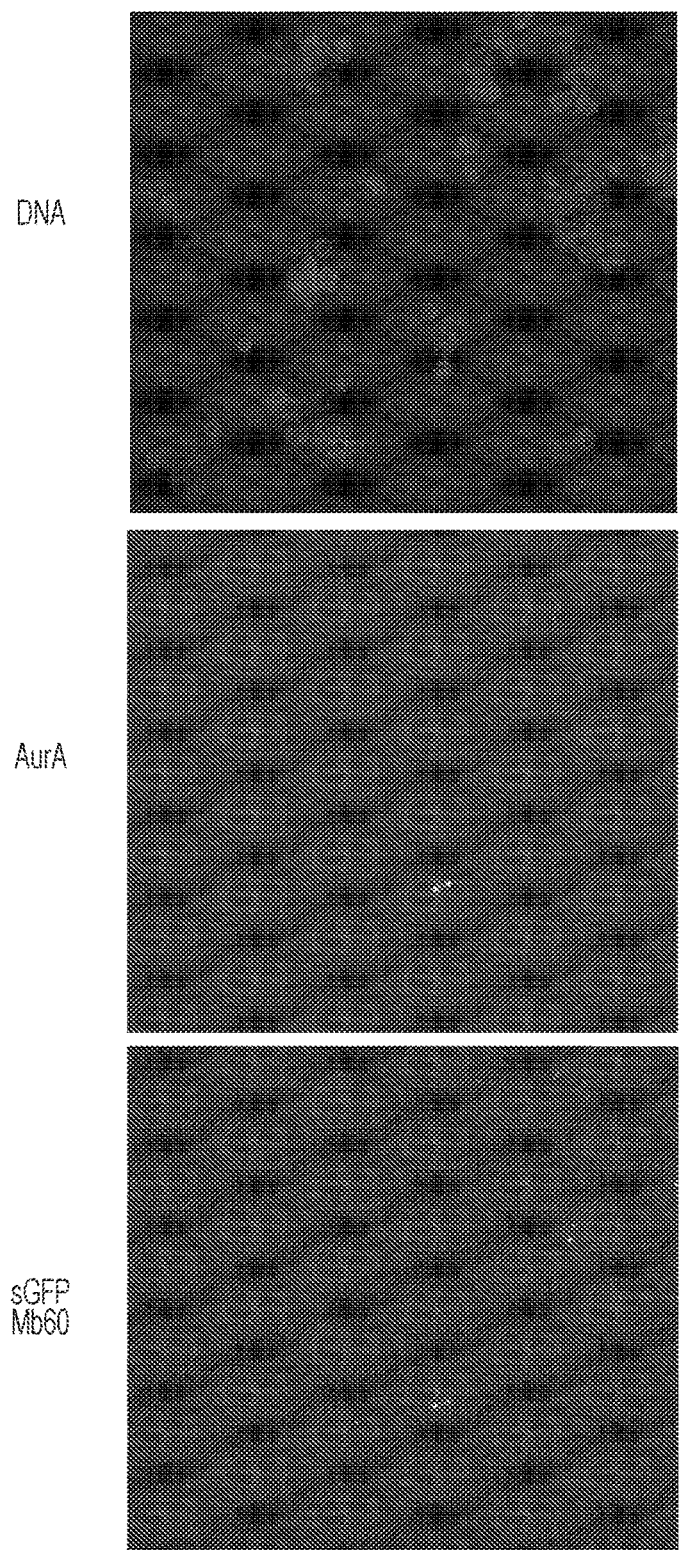
Figure 9:
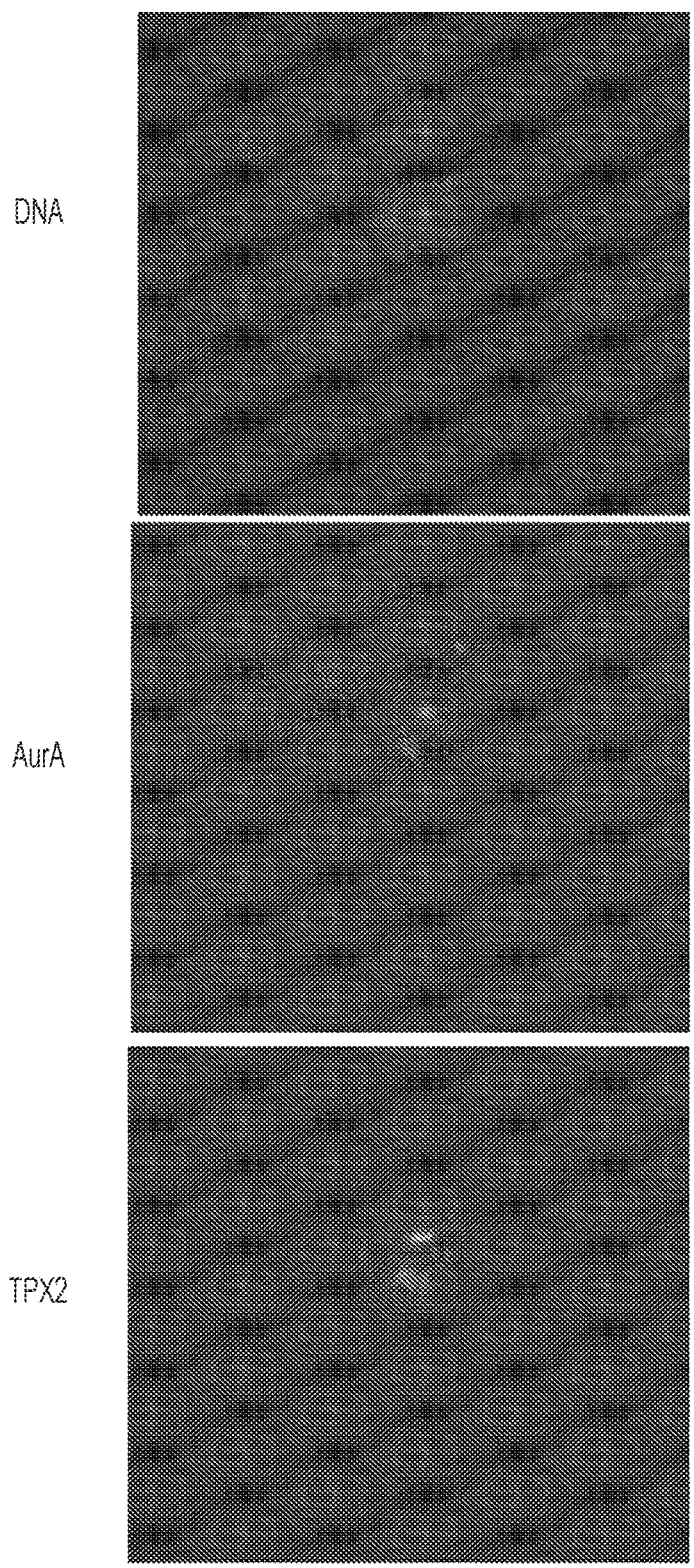
FIG. 9 is a set of micrographs showing DNA, Aurora A kinase, and TPX2 in a cell in prometaphase.

FIG. 8A shows expression and localization of sGFP-Mb60 and Aurora A kinase in vivo during various stages of the cell cycle (interphase, prophase, prometaphase, and metaphase). As shown in FIG. 8A, during prophase, prometaphase, and metaphase, expression of Aurora A kinase is elevated. FIG. 8A further shows that sGFP-Mb60 co-localized with Aurora A kinase during prophase, prometaphase, and metaphase. FIGS. 8B-8H provide the same micrographs shown in FIG. 8A, at different levels of magnification. In FIG. 9, in vivo localization of Aurora A kinase and TPX2 in during prometaphase is shown.

Figure 10:
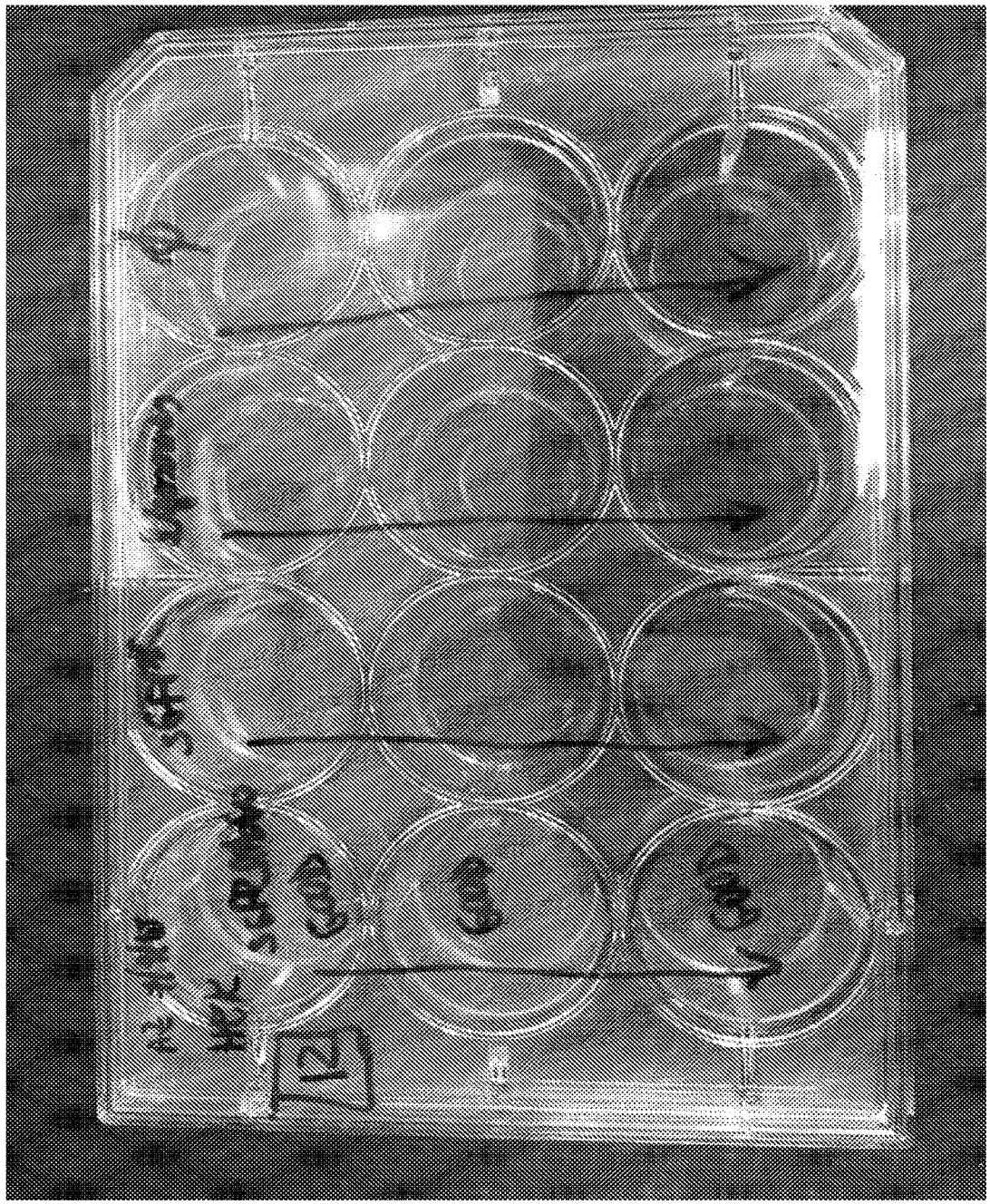
FIG. 10 is an image showing a setup of an experiment measuring cell death.

Delivery of sGFP-Mb60 into cells was found to disrupt the TPX2/Aurora A interaction in the cells. It was also observed that delivery of sGFP-Mb60 disrupted Aurora A's function in the spindles, but kept its function in the centrosome intact. For example, in FIG. SA, Aurora A was observed to localize to the centrosomes during at least prophase and prometaphase. It was also observed that the cells stayed in prometaphase, and never entered anaphase. Cell death was also observed (FIG. 10). Without being bound by theory, it is believed that the inhibitory monobody sGFP-Mb60 disrupted Aurora A's regulation of spindle assembly and/or maintenance, thereby inhibiting mitotic progression in the cells and causing cell death.

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

The invention claimed is:

1. A method of identifying an antibody mimetic that specifically binds to an allosteric site of Aurora A kinase, the method comprising
   (a) contacting a candidate antibody mimetic with an Aurora A kinase having an unbound allosteric site,
   (b) contacting the candidate antibody mimetic with an Aurora A kinase having a bound allosteric site or an Aurora A kinase mutant that has a mutation within an allosteric site,
   (c) measuring binding of the candidate antibody mimetic with Aurora A kinase in step (a) and in step (b), wherein a candidate antibody mimetic having an increased binding to Aurora A kinase in step (a) relative to step (b) is identified as the antibody mimetic that specifically binds to an allosteric site of Aurora A kinase, and
   (d) preparing an expression vector comprising a polynucleotide encoding the identified antibody mimetic.

2. The method of claim 1, wherein in step (a), a combinatorial library comprising the candidate antibody mimetic is contacted with the Aurora A kinase having the unbound allosteric site to identify a first pool of candidate antibody mimetics.

3. The method of claim 2, wherein in step (b), the first pool of candidate antibody mimetics is contacted with the Aurora A kinase having the bound allosteric site or the Aurora A kinase mutant that has the mutation within the allosteric site.

4. The method of claim 1, wherein the identified antibody mimetic binds to Aurora A kinase having an unbound allosteric site and does not bind to Aurora A kinase having a bound allosteric site and/or Aurora A kinase mutant that has a mutation within an allosteric site.

5. The method of claim 1, wherein the method further comprises transforming a host cell with the expression vector and heterologously expressing the expression vector in the host cell to produce the identified antibody mimetic.

6. The method of claim 5, further comprising purifying the expressed identified antibody mimetic.

7. The method of claim 6, further comprising preparing a pharmaceutical composition comprising the isolated identified antibody mimetic and a non-toxic pharmaceutically acceptable carrier or adjuvant.

8. The method of claim 1, wherein the antibody mimetic is a monobody.

9. The method of claim 1, wherein the allosteric site is a PDK1-interacting fragment (PIF) pocket.

10. The method of claim 1, wherein the Aurora A kinase having a bound allosteric site is Aurora A kinase bound with targeting protein for Xklp2 (TPX2).

* * * * *

SEQUENCE LISTING

```
<160> NUMBER OF SEQ ID NOS: 10

<210> SEQ ID NO 1
<211> LENGTH: 95
<212> TYPE: PRT
<213> ORGANISM: Artificial Sequence
<220> FEATURE:
<223> OTHER INFORMATION: antibody mimetic AuroraA 2 (Mb2)
```

```
<400> SEQUENCE: 1

Ser Val Ser Ser Val Pro Thr Lys Leu Glu Val Val Ala Ala Thr Pro
1               5                   10                  15

Thr Ser Leu Leu Ile Ser Trp Asp Ala Phe Gly His Gln Tyr Glu Pro
            20                  25                  30

Val Tyr Tyr Tyr Arg Ile Thr Tyr Gly Glu Thr Gly Gly Asn Ser Pro
        35                  40                  45

Val Gln Glu Phe Thr Val Pro Gly Tyr Tyr Ser Thr Ala Thr Ile Ser
    50                  55                  60

Gly Leu Lys Pro Gly Val Asp Tyr Thr Ile Thr Val Tyr Ala Trp Tyr
65                  70                  75                  80

Val Asp Gly Ser Tyr Ser Ser Pro Ile Ser Ile Asn Tyr Arg Thr
                85                  90                  95

<210> SEQ ID NO 2
<211> LENGTH: 92
<212> TYPE: PRT
<213> ORGANISM: Artificial Sequence
<220> FEATURE:
<223> OTHER INFORMATION: antibody mimetic AuroraA 44 (Mb44)

<400> SEQUENCE: 2

Ser Val Ser Ser Val Pro Thr Lys Leu Glu Val Val Ala Ala Thr Pro
1               5                   10                  15

Thr Ser Leu Leu Ile Ser Trp Asp Ala Pro Ala Val Thr Val Asp Phe
            20                  25                  30

Tyr Val Ile Thr Tyr Gly Glu Thr Gly Gly Tyr Ser Pro Trp Gln
        35                  40                  45

Glu Phe Glu Val Pro Gly Ser Lys Ser Thr Ala Thr Ile Ser Gly Leu
    50                  55                  60

Lys Pro Gly Val Asp Tyr Thr Ile Thr Val Tyr Ala Asp Tyr Gly Gln
65                  70                  75                  80

Tyr Phe Tyr Ser Pro Ile Ser Ile Asn Tyr Arg Thr
                85                  90

<210> SEQ ID NO 3
<211> LENGTH: 95
<212> TYPE: PRT
<213> ORGANISM: Artificial Sequence
<220> FEATURE:
<223> OTHER INFORMATION: antibody mimetic AuroraA 51 (Mb51)

<400> SEQUENCE: 3

Ser Val Ser Ser Val Pro Thr Lys Leu Glu Val Val Ala Ala Thr Pro
1               5                   10                  15

Thr Ser Leu Leu Ile Ser Trp Asp Ala Lys Pro Met Ser Tyr Glu Pro
            20                  25                  30

Val Tyr Tyr Tyr Arg Ile Thr Tyr Gly Glu Thr Gly Gly Asn Ser Pro
        35                  40                  45

Val Gln Glu Phe Thr Val Pro Gly Tyr Tyr Ser Thr Ala Thr Ile Ser
    50                  55                  60

Gly Leu Lys Pro Gly Val Asp Tyr Thr Ile Thr Val Tyr Ala Asp Ser
65                  70                  75                  80

Met Ser Ser Tyr Tyr Tyr Ser Pro Ile Ser Ile Asn Tyr Arg Thr
                85                  90                  95

<210> SEQ ID NO 4
```

```
<211> LENGTH: 95
<212> TYPE: PRT
<213> ORGANISM: Artificial Sequence
<220> FEATURE:
<223> OTHER INFORMATION: antibody mimetic AuroraA 54 (Mb54)

<400> SEQUENCE: 4

Ser Val Ser Ser Val Pro Thr Lys Leu Glu Val Ala Ala Thr Pro
1               5                   10                  15

Thr Ser Leu Leu Ile Ser Trp Asp Ala Gln Thr Tyr Gln Met Tyr Asp
            20                  25                  30

Tyr Val Ser Tyr Tyr Arg Ile Thr Tyr Gly Glu Thr Gly Gly Asn Ser
        35                  40                  45

Pro Val Gln Glu Phe Thr Val Pro Gly Tyr Tyr Ser Thr Ala Thr Ile
    50                  55                  60

Ser Gly Leu Lys Pro Gly Val Asp Tyr Thr Ile Thr Val Tyr Ala Glu
65                  70                  75                  80

Gly Tyr Tyr Ser Ser Tyr Ser Pro Ile Ser Ile Asn Tyr Arg Thr
                85                  90                  95

<210> SEQ ID NO 5
<211> LENGTH: 95
<212> TYPE: PRT
<213> ORGANISM: Artificial Sequence
<220> FEATURE:
<223> OTHER INFORMATION: antibody mimetic AuroraA 56 (Mb56)

<400> SEQUENCE: 5

Ser Val Ser Ser Val Pro Thr Lys Leu Glu Val Ala Ala Thr Pro
1               5                   10                  15

Thr Ser Leu Leu Ile Ser Trp Asp Ala Met Ser Asp Trp Tyr Tyr Trp
            20                  25                  30

Val Asp Tyr Tyr Arg Ile Thr Tyr Gly Glu Thr Gly Gly Asn Ser Pro
        35                  40                  45

Val Gln Glu Phe Thr Val Pro Gly Ser Tyr Ser Thr Ala Thr Ile Ser
    50                  55                  60

Gly Leu Lys Pro Gly Val Asp Tyr Thr Ile Thr Val Tyr Ala Ser Asp
65                  70                  75                  80

Asp Val Trp Gly Asp Tyr Ser Pro Ile Ser Ile Asn Tyr Arg Thr
                85                  90                  95

<210> SEQ ID NO 6
<211> LENGTH: 92
<212> TYPE: PRT
<213> ORGANISM: Artificial Sequence
<220> FEATURE:
<223> OTHER INFORMATION: antibody mimetic AuroraA 60 (Mb60)

<400> SEQUENCE: 6

Ser Val Ser Ser Val Pro Thr Lys Leu Glu Val Ala Ala Thr Pro
1               5                   10                  15

Thr Ser Leu Leu Ile Ser Trp Asp Ala Pro Ala Val Thr Val Val His
            20                  25                  30

Tyr Val Ile Thr Tyr Gly Glu Thr Gly Gly Asn Ser Pro Val Gln Glu
        35                  40                  45

Phe Thr Val Pro Gly Ser Lys Ser Thr Ala Thr Ile Ser Gly Leu Lys
    50                  55                  60

Pro Gly Val Asp Tyr Thr Ile Thr Val Tyr Ala Ile Asp Phe Tyr Trp
65                  70                  75                  80
```

```
Gly Ser Tyr Ser Pro Ile Ser Ile Asn Tyr Arg Thr
                85                  90
```

<210> SEQ ID NO 7
<211> LENGTH: 403
<212> TYPE: PRT
<213> ORGANISM: Homo sapiens

<400> SEQUENCE: 7

```
Met Asp Arg Ser Lys Glu Asn Cys Ile Ser Gly Pro Val Lys Ala Thr
1               5                   10                  15

Ala Pro Val Gly Gly Pro Lys Arg Val Leu Val Thr Gln Gln Phe Pro
            20                  25                  30

Cys Gln Asn Pro Leu Pro Val Asn Ser Gly Gln Ala Gln Arg Val Leu
        35                  40                  45

Cys Pro Ser Asn Ser Ser Gln Arg Ile Pro Leu Gln Ala Gln Lys Leu
    50                  55                  60

Val Ser Ser His Lys Pro Val Gln Asn Gln Lys Gln Lys Gln Leu Gln
65                  70                  75                  80

Ala Thr Ser Val Pro His Pro Val Ser Arg Pro Leu Asn Asn Thr Gln
                85                  90                  95

Lys Ser Lys Gln Pro Leu Pro Ser Ala Pro Glu Asn Asn Pro Glu Glu
            100                 105                 110

Glu Leu Ala Ser Lys Gln Lys Asn Glu Glu Ser Lys Lys Arg Gln Trp
        115                 120                 125

Ala Leu Glu Asp Phe Glu Ile Gly Arg Pro Leu Gly Lys Gly Lys Phe
    130                 135                 140

Gly Asn Val Tyr Leu Ala Arg Glu Lys Gln Ser Lys Phe Ile Leu Ala
145                 150                 155                 160

Leu Lys Val Leu Phe Lys Ala Gln Leu Glu Lys Ala Gly Val Glu His
                165                 170                 175

Gln Leu Arg Arg Glu Val Glu Ile Gln Ser His Leu Arg His Pro Asn
            180                 185                 190

Ile Leu Arg Leu Tyr Gly Tyr Phe His Asp Ala Thr Arg Val Tyr Leu
        195                 200                 205

Ile Leu Glu Tyr Ala Pro Leu Gly Thr Val Tyr Arg Glu Leu Gln Lys
    210                 215                 220

Leu Ser Lys Phe Asp Glu Gln Arg Thr Ala Thr Tyr Ile Thr Glu Leu
225                 230                 235                 240

Ala Asn Ala Leu Ser Tyr Cys His Ser Lys Arg Val Ile His Arg Asp
                245                 250                 255

Ile Lys Pro Glu Asn Leu Leu Leu Gly Ser Ala Gly Glu Leu Lys Ile
            260                 265                 270

Ala Asp Phe Gly Trp Ser Val His Ala Pro Ser Ser Arg Arg Thr Thr
        275                 280                 285

Leu Cys Gly Thr Leu Asp Tyr Leu Pro Pro Glu Met Ile Glu Gly Arg
    290                 295                 300

Met His Asp Glu Lys Val Asp Leu Trp Ser Leu Gly Val Leu Cys Tyr
305                 310                 315                 320

Glu Phe Leu Val Gly Lys Pro Pro Phe Glu Ala Asn Thr Tyr Gln Glu
                325                 330                 335

Thr Tyr Lys Arg Ile Ser Arg Val Glu Phe Thr Phe Pro Asp Phe Val
            340                 345                 350

Thr Glu Gly Ala Arg Asp Leu Ile Ser Arg Leu Leu Lys His Asn Pro
        355                 360                 365
```

Ser Gln Arg Pro Met Leu Arg Glu Val Leu Glu His Pro Trp Ile Thr
    370                 375                 380

Ala Asn Ser Ser Lys Pro Ser Asn Cys Gln Asn Lys Glu Ser Ala Ser
385                 390                 395                 400

Lys Gln Ser

<210> SEQ ID NO 8
<211> LENGTH: 2121
<212> TYPE: DNA
<213> ORGANISM: Homo sapiens

<400> SEQUENCE: 8

| | | | | | |
|---|---|---|---|---|---|
| acaaggcagc | ctcgctcgag | cgcaggccaa | tcggctttct | agctagaggg | tttaactcct | 60 |
| atttaaaaag | aagaaccttt | gaattctaac | ggctgagctc | ttggaagact | tgggtccttg | 120 |
| ggtcgcaggc | atcatggacc | gatctaaaga | aaactgcatt | tcaggacctg | ttaaggctac | 180 |
| agctccagtt | ggaggtccaa | aacgtgttct | cgtgactcag | caatttcctt | gtcagaatcc | 240 |
| attacctgta | aatagtggcc | aggctcagcg | ggtcttgtgt | ccttcaaatt | cttcccagcg | 300 |
| cattcctttg | caagcacaaa | agcttgtctc | cagtcacaag | ccggttcaga | atcagaagca | 360 |
| gaagcaattg | caggcaacca | gtgtacctca | tcctgtctcc | aggccactga | ataacaccca | 420 |
| aaagagcaag | cagcccctgc | catcggcacc | tgaaaataat | cctgaggagg | aactggcatc | 480 |
| aaaacagaaa | aatgaagaat | caaaaagag | gcagtgggct | ttggaagact | tgaaattgg | 540 |
| tcgccctctg | ggtaaaggaa | agtttggtaa | tgtttatttg | gcaagagaaa | agcaaagcaa | 600 |
| gtttattctg | gctcttaaag | tgttatttaa | agctcagctg | gagaaagccg | gagtggagca | 660 |
| tcagctcaga | gagaagtag | aaatacagtc | ccaccttcgg | catcctaata | ttcttagact | 720 |
| gtatggttat | ttccatgatg | ctaccagagt | ctacctaatt | ctggaatatg | caccacttgg | 780 |
| aacagtttat | agagaacttc | agaaactttc | aaagtttgat | gagcagagaa | ctgctactta | 840 |
| tataacagaa | ttggcaaatg | ccctgtctta | ctgtcattcg | aagagagtta | tcatagaga | 900 |
| cattaagcca | gagaacttac | ttcttggatc | agctggagag | cttaaaattg | cagattttgg | 960 |
| gtggtcagta | catgctccat | cttccaggag | gaccactctc | tgtggcaccc | tggactacct | 1020 |
| gcccctgaa | atgattgaag | gtcggatgca | tgatgagaag | gtggatctct | ggagccttgg | 1080 |
| agttctttgc | tatgaatttt | tagttgggaa | gcctccttt | gaggcaaaca | ataccaaga | 1140 |
| gacctacaaa | agaatatcac | gggttgaatt | cacattccct | gactttgtaa | cagagggagc | 1200 |
| cagggacctc | atttcaagac | tgttgaagca | taatcccagc | cagaggccaa | tgctcagaga | 1260 |
| agtacttgaa | caccctgga | tcacagcaaa | ttcatcaaaa | ccatcaaatt | gccaaaacaa | 1320 |
| agaatcagct | agcaaacagt | cttaggaatc | gtgcaggggg | agaaatcctt | gagccagggc | 1380 |
| tgccatataa | cctgacagga | acatgctact | gaagtttatt | ttaccattga | ctgctgccct | 1440 |
| caatctagaa | cgctacacaa | gaaatatttg | ttttactcag | caggtgtgcc | ttaacctccc | 1500 |
| tattcagaaa | gctccacatc | aataaacatg | acactctgaa | gtgaaagtag | ccacgagaat | 1560 |
| tgtgctactt | atactggttc | ataatctgga | ggcaaggttc | gactgcagcc | gccccgtcag | 1620 |
| cctgtgctag | gcatggtgtc | ttcacaggag | gcaaatccag | agcctggctg | tggggaaagt | 1680 |
| gaccactctg | ccctgacccc | gatcagttaa | ggagctgtgc | aataaccttc | ctagtacctg | 1740 |
| agtgagtgtg | taacttattg | ggttggcgaa | gcctggtaaa | gctgttggaa | tgagtatgtg | 1800 |
| attcttttta | agtatgaaaa | taagatata | tgtacagact | tgtatttttt | ctctggtggc | 1860 |

-continued

```
attcctttag gaatgctgtg tgtctgtccg gcaccccggt aggcctgatt gggtttctag    1920
tcctccttaa ccacttatct cccatatgag agtgtgaaaa ataggaacac gtgctctacc    1980
tccatttagg gatttgcttg ggatacagaa gaggccatgt gtctcagagc tgttaagggc    2040
ttattttttt aaaacattgg agtcatagca tgtgtgtaaa ctttaaatat gcaaataaat    2100
aagtatctat gtctaaaaaa a                                              2121

<210> SEQ ID NO 9
<211> LENGTH: 783
<212> TYPE: PRT
<213> ORGANISM: Homo sapiens

<400> SEQUENCE: 9

Met Ser Gln Val Lys Ser Ser Tyr Ser Tyr Asp Ala Pro Ser Asp Phe
1               5                   10                  15

Ile Asn Phe Ser Ser Leu Asp Asp Glu Gly Asp Thr Gln Asn Ile Asp
            20                  25                  30

Ser Trp Phe Glu Glu Lys Ala Asn Leu Glu Asn Lys Leu Leu Gly Lys
        35                  40                  45

Asn Gly Thr Gly Gly Leu Phe Gln Gly Lys Thr Pro Leu Arg Lys Ala
    50                  55                  60

Asn Leu Gln Gln Ala Ile Val Thr Pro Leu Lys Pro Val Asp Asn Thr
65                  70                  75                  80

Tyr Tyr Lys Glu Ala Glu Lys Glu Asn Leu Val Glu Gln Ser Ile Pro
                85                  90                  95

Ser Asn Ala Cys Ser Ser Leu Glu Val Glu Ala Ala Ile Ser Arg Lys
            100                 105                 110

Thr Pro Ala Gln Pro Gln Arg Arg Ser Leu Arg Leu Ser Ala Gln Lys
        115                 120                 125

Asp Leu Glu Gln Lys Glu Lys His Val Lys Met Lys Ala Lys Arg
130                 135                 140

Cys Ala Thr Pro Val Ile Ile Asp Glu Ile Leu Pro Ser Lys Lys Met
145                 150                 155                 160

Lys Val Ser Asn Asn Lys Lys Pro Glu Glu Gly Ser Ala His
                165                 170                 175

Gln Asp Thr Ala Glu Lys Asn Ala Ser Ser Pro Glu Lys Ala Lys Gly
            180                 185                 190

Arg His Thr Val Pro Cys Met Pro Pro Ala Lys Gln Lys Phe Leu Lys
        195                 200                 205

Ser Thr Glu Glu Gln Glu Leu Glu Lys Ser Met Lys Met Gln Gln Glu
    210                 215                 220

Val Val Glu Met Arg Lys Lys Asn Glu Glu Phe Lys Lys Leu Ala Leu
225                 230                 235                 240

Ala Gly Ile Gly Gln Pro Val Lys Lys Ser Val Ser Gln Val Thr Lys
                245                 250                 255

Ser Val Asp Phe His Phe Arg Thr Asp Glu Arg Ile Lys Gln His Pro
            260                 265                 270

Lys Asn Gln Glu Glu Tyr Lys Glu Val Asn Phe Thr Ser Glu Leu Arg
        275                 280                 285

Lys His Pro Ser Ser Pro Ala Arg Val Thr Lys Gly Cys Thr Ile Val
    290                 295                 300

Lys Pro Phe Asn Leu Ser Gln Gly Lys Lys Arg Thr Phe Asp Glu Thr
305                 310                 315                 320

Val Ser Thr Tyr Val Pro Leu Ala Gln Gln Val Glu Asp Phe His Lys
```

```
              325                 330                 335
Arg Thr Pro Asn Arg Tyr His Leu Arg Ser Lys Lys Asp Asp Ile Lys
            340                 345                 350
Thr Gly Ser Cys Ser Val Thr Gln Ala Gly Val Gln Trp Arg Asp His
        355                 360                 365
Gly Ser Leu Gln Cys Pro Thr Pro Gly Leu Lys Gln Ser Ser Cys Leu
    370                 375                 380
Ser Leu Pro Asn Leu Leu Pro Ser Lys Ser Val Thr Lys Ile Cys
385                 390                 395                 400
Arg Asp Pro Gln Thr Pro Val Leu Gln Thr Lys His Arg Ala Arg Ala
                405                 410                 415
Val Thr Cys Lys Ser Thr Ala Glu Leu Glu Ala Glu Leu Glu Lys
            420                 425                 430
Leu Gln Gln Tyr Lys Phe Lys Ala Arg Glu Leu Asp Pro Arg Ile Leu
        435                 440                 445
Glu Gly Gly Pro Ile Leu Pro Lys Lys Pro Val Lys Pro Pro Thr
    450                 455                 460
Glu Pro Ile Gly Phe Asp Leu Glu Ile Glu Lys Arg Ile Gln Glu Arg
465                 470                 475                 480
Glu Ser Lys Lys Lys Thr Glu Asp Glu His Phe Glu Phe His Ser Arg
                485                 490                 495
Pro Cys Pro Thr Lys Ile Leu Glu Asp Val Val Gly Val Pro Glu Lys
            500                 505                 510
Lys Val Leu Pro Ile Thr Val Pro Lys Ser Pro Ala Phe Ala Leu Lys
        515                 520                 525
Asn Arg Ile Arg Met Pro Thr Lys Glu Asp Glu Glu Asp Glu Pro
    530                 535                 540
Val Val Ile Lys Ala Gln Pro Val Pro His Tyr Gly Val Pro Phe Lys
545                 550                 555                 560
Pro Gln Ile Pro Glu Ala Arg Thr Val Glu Ile Cys Pro Phe Ser Phe
                565                 570                 575
Asp Ser Arg Asp Lys Glu Arg Gln Leu Gln Lys Glu Lys Ile Lys
            580                 585                 590
Glu Leu Gln Lys Gly Glu Val Pro Lys Phe Lys Ala Leu Pro Leu Pro
        595                 600                 605
His Phe Asp Thr Ile Asn Leu Pro Glu Lys Lys Val Lys Asn Val Thr
    610                 615                 620
Gln Ile Glu Pro Phe Cys Leu Glu Thr Asp Arg Arg Gly Ala Leu Lys
625                 630                 635                 640
Ala Gln Thr Trp Lys His Gln Leu Glu Glu Leu Arg Gln Gln Lys
                645                 650                 655
Glu Ala Ala Cys Phe Lys Ala Arg Pro Asn Thr Val Ile Ser Gln Glu
            660                 665                 670
Pro Phe Val Pro Lys Lys Glu Lys Lys Ser Val Ala Glu Gly Leu Ser
        675                 680                 685
Gly Ser Leu Val Gln Glu Pro Phe Gln Leu Ala Thr Glu Lys Arg Ala
    690                 695                 700
Lys Glu Arg Gln Glu Leu Glu Lys Arg Met Ala Glu Val Glu Ala Gln
705                 710                 715                 720
Lys Ala Gln Gln Leu Glu Glu Ala Arg Leu Gln Glu Glu Gln Lys
                725                 730                 735
Lys Glu Glu Leu Ala Arg Leu Arg Arg Glu Leu Val His Lys Ala Asn
            740                 745                 750
```

Pro Ile Arg Lys Tyr Gln Gly Leu Glu Ile Lys Ser Ser Asp Gln Pro
       755                 760                 765

Leu Thr Val Pro Val Ser Pro Lys Phe Ser Thr Arg Phe His Cys
    770                 775                 780

<210> SEQ ID NO 10
<211> LENGTH: 3685
<212> TYPE: DNA
<213> ORGANISM: Homo sapiens

<400> SEQUENCE: 10

| | | | | | |
|---|---|---|---|---|---|
| agtggactca | cgcaggcgca | ggagactaca | cttcccagga | actccgggcc | gcgttgttcg | 60 |
| ctggtacctc | cttctgactt | ccggtattgc | tgcggtctgt | agggccaatc | gggagcctgg | 120 |
| aattgctttc | ccggcgctct | gattggtgca | ttcgactagg | ctgcctgggt | tcaaaatttc | 180 |
| aacgatactg | aatgagtccc | gcggcgggtt | ggctcgcgct | tcgttgtcag | atctgaggcg | 240 |
| aggctaggtg | agccgtggga | agaaaagagg | gagcagctag | ggcgcgggtc | tccctcctcc | 300 |
| cggagtttgg | aacggctgaa | gttcaccttc | agcccctag | cgccgttcgc | gccgctaggc | 360 |
| ctggcttctg | aggcggttgc | ggtgctcggt | cgccgcctag | gcggggcagg | gtgcgagcag | 420 |
| gggcttcggg | ccacgcttct | cttggcgaca | ggattttgct | gtgaagtccg | tccgggaaac | 480 |
| ggaggaaaaa | aagagttgcg | ggaggctgtc | ggctaataac | ggttcttgat | acatatttgc | 540 |
| cagacttcaa | gatttcagaa | aagggtgaa | agagaagatt | gcaactttga | gtcagacctg | 600 |
| taggcctgat | agactgatta | aaccacagaa | ggtgacctgc | tgagaaaagt | ggtacaaata | 660 |
| ctgggaaaaa | cctgctcttc | tgcgttaagt | gggagacaat | gtcacaagtt | aaaagctctt | 720 |
| attcctatga | tgcccctcg | gatttcatca | attttcatc | cttggatgat | gaaggagata | 780 |
| ctcaaaacat | agattcatgg | tttgaggaga | aggccaattt | ggagaataag | ttactgggga | 840 |
| agaatggaac | tggagggctt | tttcagggca | aaactccttt | gagaaaggct | aatcttcagc | 900 |
| aagctattgt | cacacctttg | aaaccagttg | acaacactta | ctacaaagag | gcagaaaaag | 960 |
| aaaatcttgt | ggaacaatcc | attccgtcaa | atgcttgttc | ttccctggaa | gttgaggcag | 1020 |
| ccatatcaag | aaaaactcca | gcccagcctc | agagaagatc | tcttaggctt | tctgctcaga | 1080 |
| aggatttgga | acagaaagaa | aagcatcatg | taaaaatgaa | agccaagaga | tgtgccactc | 1140 |
| ctgtaatcat | cgatgaaatt | ctaccctcta | gaaaatgaa | agtttctaac | aacaaaaaga | 1200 |
| agccagagga | agaaggcagt | gctcatcaag | atactgctga | aaagaatgca | tcttccccag | 1260 |
| agaaagccaa | gggtagacat | actgtgcctt | gtatgccacc | tgcaaagcag | aagtttctaa | 1320 |
| aaagtactga | ggagcaagag | ctggagaaga | gtatgaaaat | gcagcaagag | gtggtggaga | 1380 |
| tgcggaaaaa | gaatgaagaa | ttcaagaaac | ttgctctggc | tggaataggg | caacctgtga | 1440 |
| agaaatcagt | gagccaggtc | accaaatcag | ttgacttcca | cttccgcaca | gatgagcgaa | 1500 |
| tcaaacaaca | tcctaagaac | caggaggaat | ataaggaagt | gaactttaca | tctgaactac | 1560 |
| gaaagcatcc | ttcatctcct | gcccgagtga | ctaagggatg | taccattgtt | aagcctttca | 1620 |
| acctgtccca | aggaaagaaa | agaacatttg | atgaaacagt | ttctacatat | gtgccccttg | 1680 |
| cacagcaagt | tgaagacttc | cataaacgaa | cccctaacag | atatcatttg | aggagcaaga | 1740 |
| aggatgatat | taacctgtta | ccctccaaat | cttctgtgac | caagatttgc | agagacccac | 1800 |
| agactcctgt | actgcaaacc | aaacaccgtg | cacgggctgt | gacctgcaaa | agtacagcag | 1860 |
| agctggaggc | tgaggagctc | gagaaattgc | aacaatacaa | attcaaagca | cgtgaacttg | 1920 |

```
atcccagaat acttgaaggt gggcccatct tgcccaagaa accacctgtg aaaccaccca    1980
ccgagcctat tggctttgat ttggaaattg agaaaagaat ccaggagcga gaatcaaaga    2040
agaaaacaga ggatgaacac tttgaatttc attccagacc ttgccctact aagattttgg    2100
aagatgttgt gggtgttcct gaaaagaagg tacttccaat caccgtcccc aagtcaccag    2160
cctttgcatt gaagaacaga attcgaatgc ccaccaaaga agatgaggaa gaggacgaac    2220
cggtagtgat aaaagctcaa cctgtgccac attatgtgggt gccttttaag ccccaaatcc    2280
cagaggcaag aactgtggaa atatgccctt tctcgtttga ttctcgagac aaagaacgtc    2340
agttacagaa ggagaagaaa ataaaagaac tgcagaaagg ggaggtgccc aagttcaagg    2400
cacttccctt gcctcatttt gacaccatta acctgccaga gaagaaggta aagaatgtga    2460
cccagattga acctttctgc ttggagactg acagaagagg tgctctgaag gcacagactt    2520
ggaagcacca gctggaagaa gaactgagac agcagaaaga agcagcttgt ttcaaggctc    2580
gtccaaacac cgtcatctct caggagcct  ttgttcccaa gaaagagaag aaatcagttg    2640
ctgagggcct ttctggttct ctagttcagg aaccttttca gctggctact gagaagagag    2700
ccaaagagcg gcaggagctg gagaagagaa tggctgaggt agaagcccag aaagcccagc    2760
agttggagga ggccagacta caggaggaag agcagaaaaa agaggagctg gccaggctac    2820
ggagagaact ggtgcataag gcaaatccaa tacgcaagta ccagggtctg gagataaagt    2880
caagtgacca gcctctgact gtgcctgtat ctcccaaatt ctccactcga ttccactgct    2940
aaactcagct gtgagctgcg gataccgccc ggcaatggga cctgctctta acctcaaacc    3000
taggaccgtc ttgctttgtc attgggcatg gagagaaccc attctccag acttttacct      3060 acccgtgcct gagaaagcat acttgacaac tgtggactcc agttttgttg agaattgttt    3120
tcttacatta ctaaggctaa taatgagatg taactcatga atgtctcgat tagactccat    3180
gtagttactt cctttaaacc atcagccggc cttttatatg ggtcttcact ctgactagaa    3240
tttagtctct gtgtcagcac agtgtaatct ctattgctat tgccccttac gactctcacc    3300
ctctccccac ttttttttaaa aatttaacc agaaaataaa gatagttaaa tcctaagata    3360
gagattaagt catggtttaa atgaggaaca atcagtaaat cagattctgt cctcttctct    3420
gcataccgtg aatttatagt taaggatccc tttgctgtga gggtagaaaa cctcaccaac    3480
tgcaccagtg aggaagaaga ctgcgtggat tcatggggag cctcacagca gccacgcagc    3540
aggctctggg tggggctgcc gttaaggcac gttctttcct tactggtgct gataacaaca    3600
gggaaccgtg cagtgtgcat tttaagacct ggcctggaat aaatacgttt tgtctttccc    3660
tcaaaaaaaa aaaaaaaaaa aaaaa                                          3685
```